United States Patent
Chaiken et al.

(10) Patent No.: US 10,251,931 B2
(45) Date of Patent: Apr. 9, 2019

(54) CYCLIC PEPTIDES AND METHODS USING SAME

(71) Applicant: DREXEL UNIVERSITY, Philadelphia, PA (US)

(72) Inventors: Irwin M. Chaiken, Gladwyne, PA (US); Adel Ahmed Rashad Ahmed, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 15/533,075

(22) PCT Filed: Dec. 9, 2015

(86) PCT No.: PCT/US2015/064708
§ 371 (c)(1),
(2) Date: Jun. 5, 2017

(87) PCT Pub. No.: WO2016/094518
PCT Pub. Date: Jun. 16, 2016

(65) Prior Publication Data
US 2017/0360879 A1   Dec. 21, 2017

Related U.S. Application Data

(60) Provisional application No. 62/089,294, filed on Dec. 9, 2014.

(51) Int. Cl.
| | |
|---|---|
| *A61K 38/12* | (2006.01) |
| *A61K 9/127* | (2006.01) |
| *C07K 7/56* | (2006.01) |
| *C07K 7/60* | (2006.01) |
| *A61K 38/00* | (2006.01) |

(52) U.S. Cl.
CPC .............. *A61K 38/12* (2013.01); *A61K 9/127* (2013.01); *C07K 7/56* (2013.01); *C07K 7/60* (2013.01); *A61K 38/00* (2013.01)

(58) Field of Classification Search
None
See application file for complete search history.

(56) References Cited

U.S. PATENT DOCUMENTS

2014/0050793 A1   2/2014   Chaiken et al.

OTHER PUBLICATIONS

International Search Report and Written Opinion for PCT International Application No. PCT/US2015/064708 dated May 2, 2016.
Aneja, et al., "Peptide Triazole Inactivators of HIV-1 Utilize a Conserved Two-Cavity Binding Site at the Junction of the Inner and Outer Domains of Env gp120", J. Med Chem. 58(9), 2015, 3843-3858.
Bastian, et al., "Interactions of peptide triazole thiols with Env gp120 induce irreversible breakdown and inactivation of HIV-1 virions", Retrovirology 10, 2013, 153.
Emileh, et al., "Covalent conjugation of a peptide triazole to HIV-1 gp120 enables intramolecular binding site occupancy", Biochemistry. 53(21), 2014, 3403-3414.
Rashad, et al., "Macrocyclic Envelope Glycoprotein Antagonists that Irreversibly Inactivate HIV-1 before Host Cell Encounter", J Med Chem. 58(18), 2015, 7603-7608.

*Primary Examiner* — Thomas S Heard
(74) *Attorney, Agent, or Firm* — Saul Ewing Arnstein & Lehr LLP; Kathryn Doyle; Domingos J. Silva

(57) ABSTRACT

The present invention includes novel cyclic peptides, and methods of using the same. The present invention further includes novel cyclic peptides conjugated with a gold nanoparticle, and methods of using the same.

12 Claims, 26 Drawing Sheets

Specification includes a Sequence Listing.

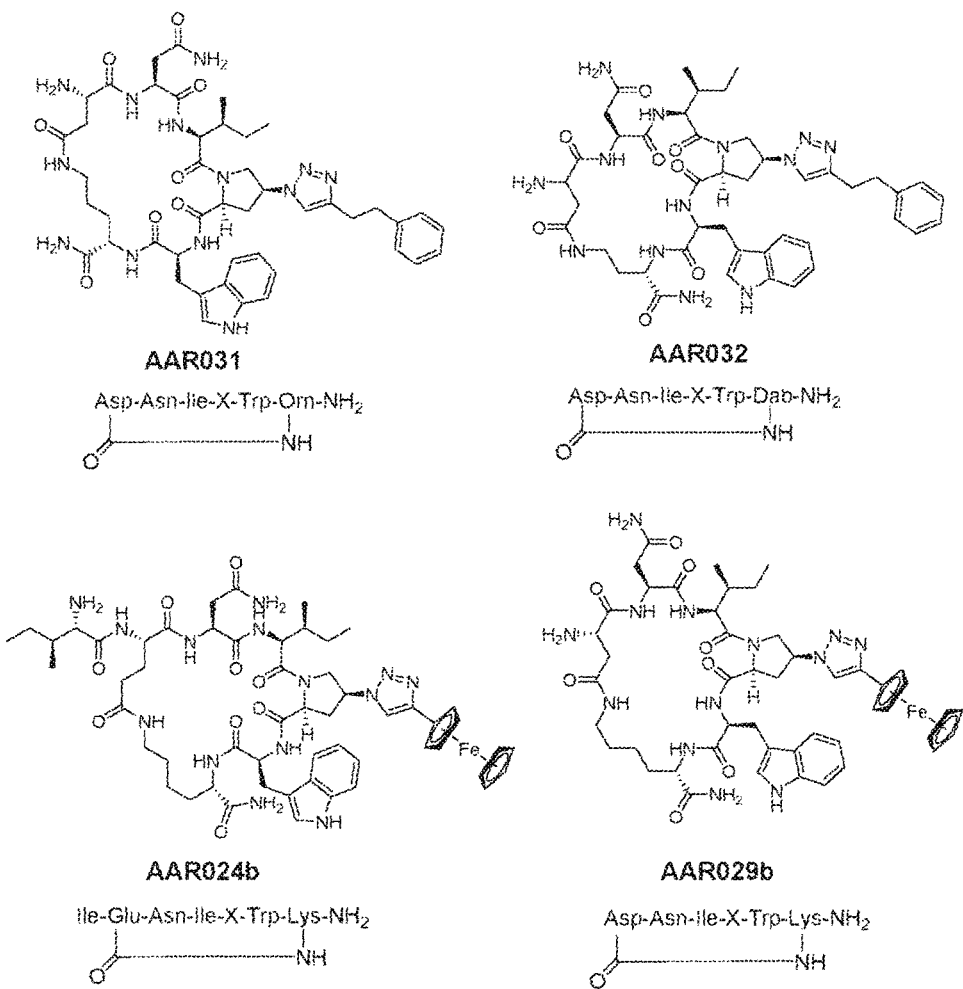

Fig. 2c
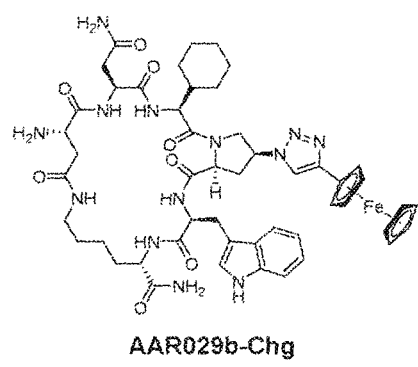
AAR029b-Chg
Asp-Asn-CyHexGly-X-Trp-Lys-NH₂
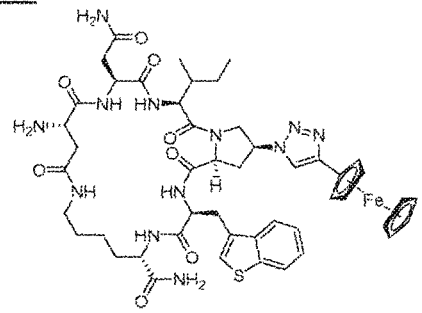
AAR029E
Asp-Asn-Ile-X-BenzothienylAla-Lys-NH₂
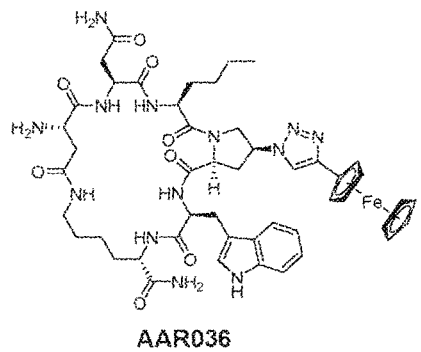
AAR036
Asp-Asn-Nle-X-Trp-Lys-NH₂
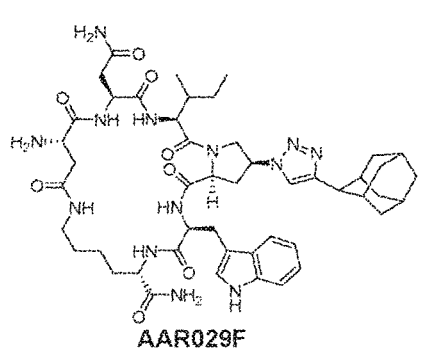
AAR029F
Asp-Asn-Ile-X-Trp-Lys-NH₂

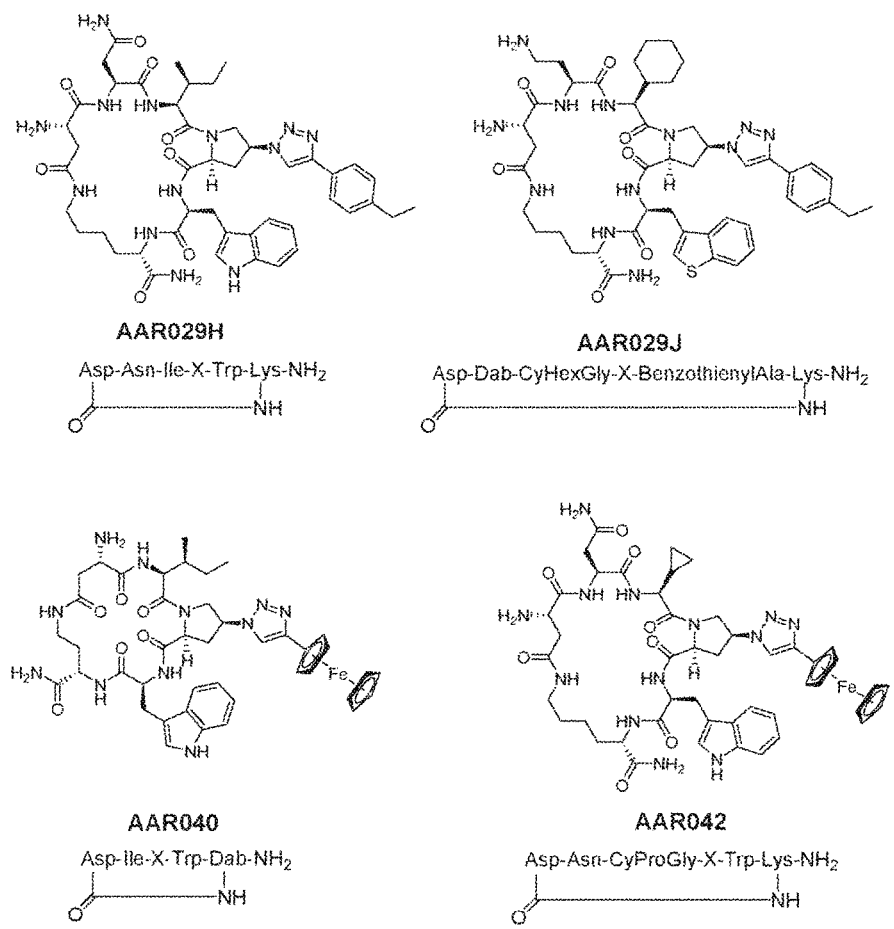

Fig. 4a
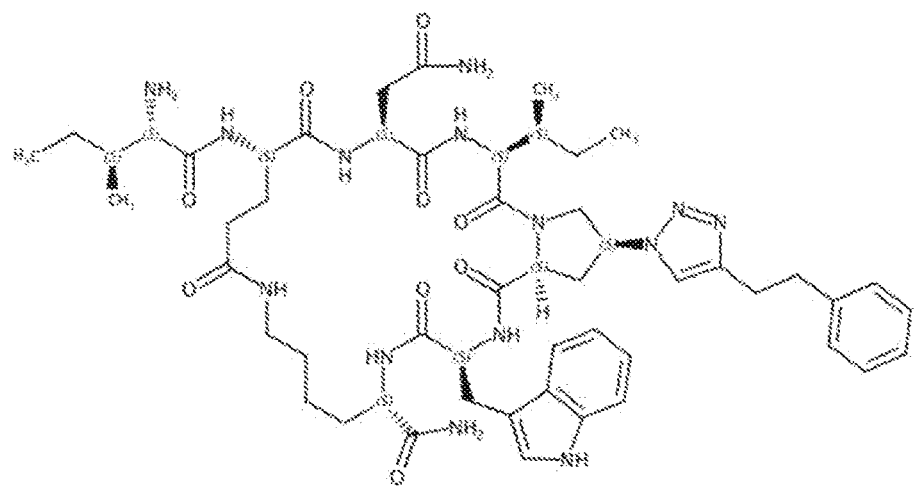
AAR024
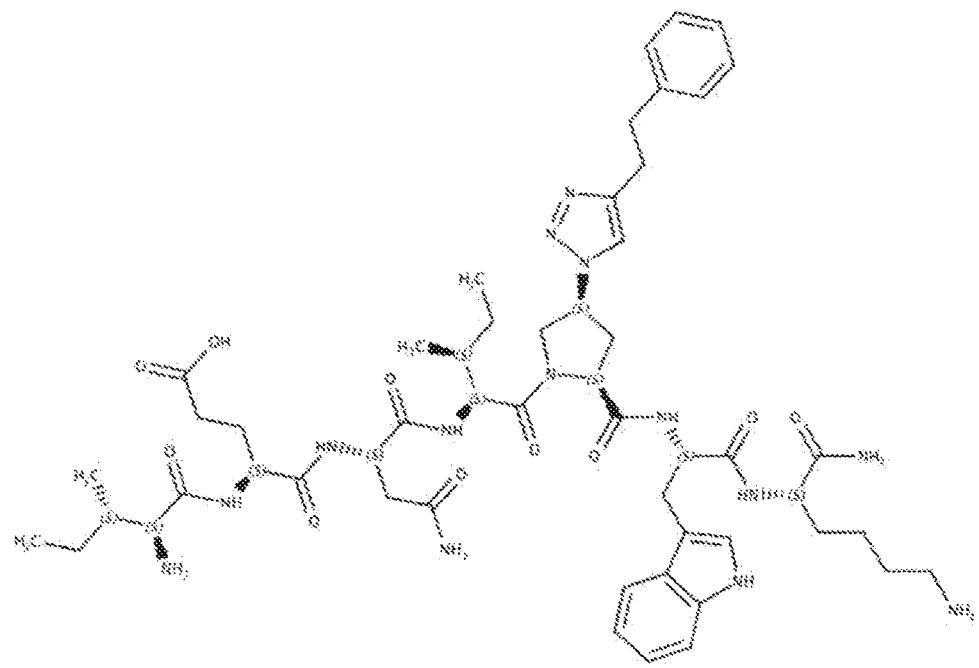
AAR024A

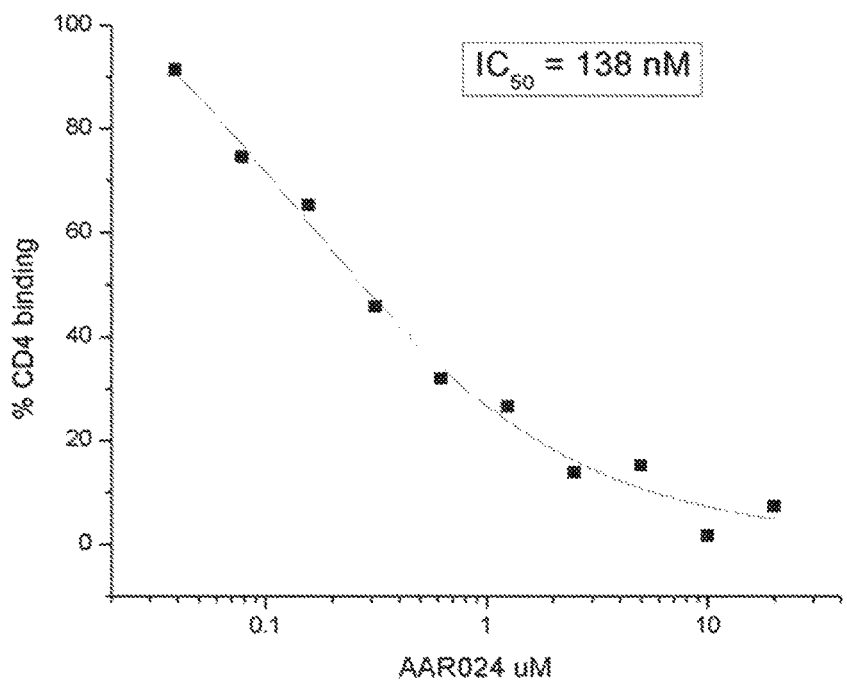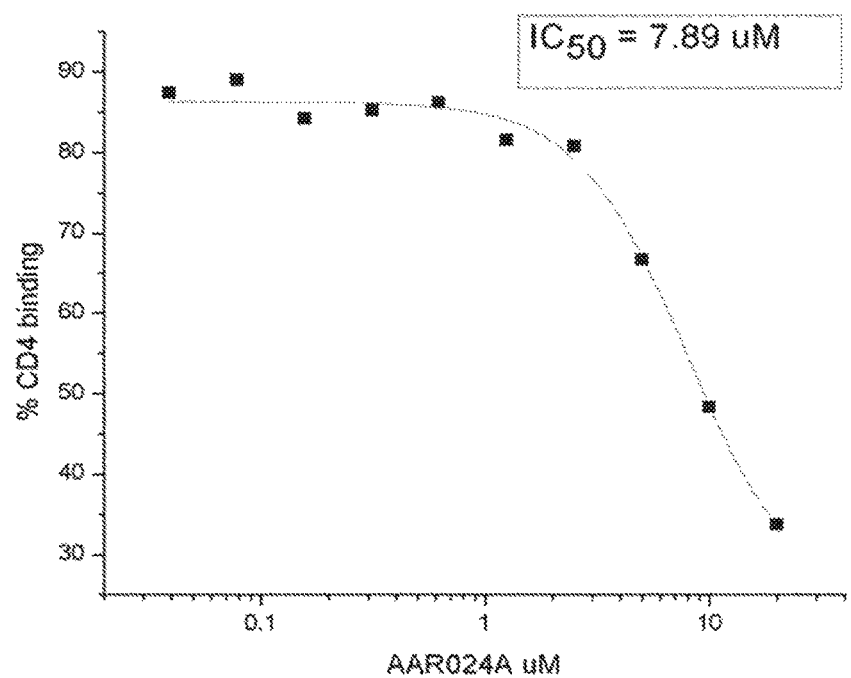
Fig. 4b

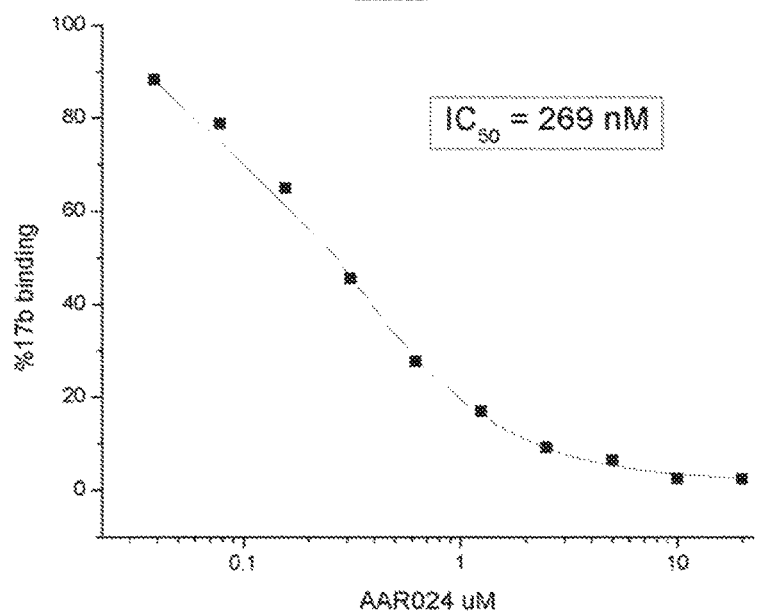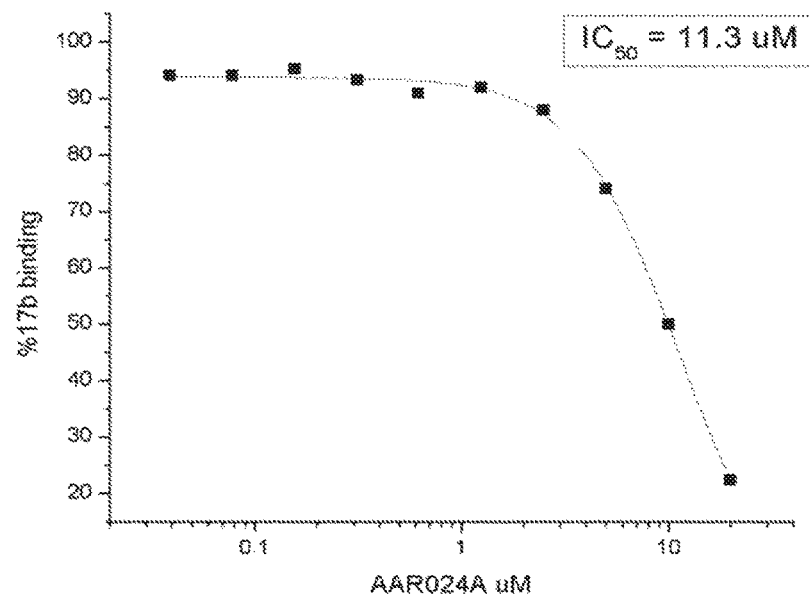

AAR026

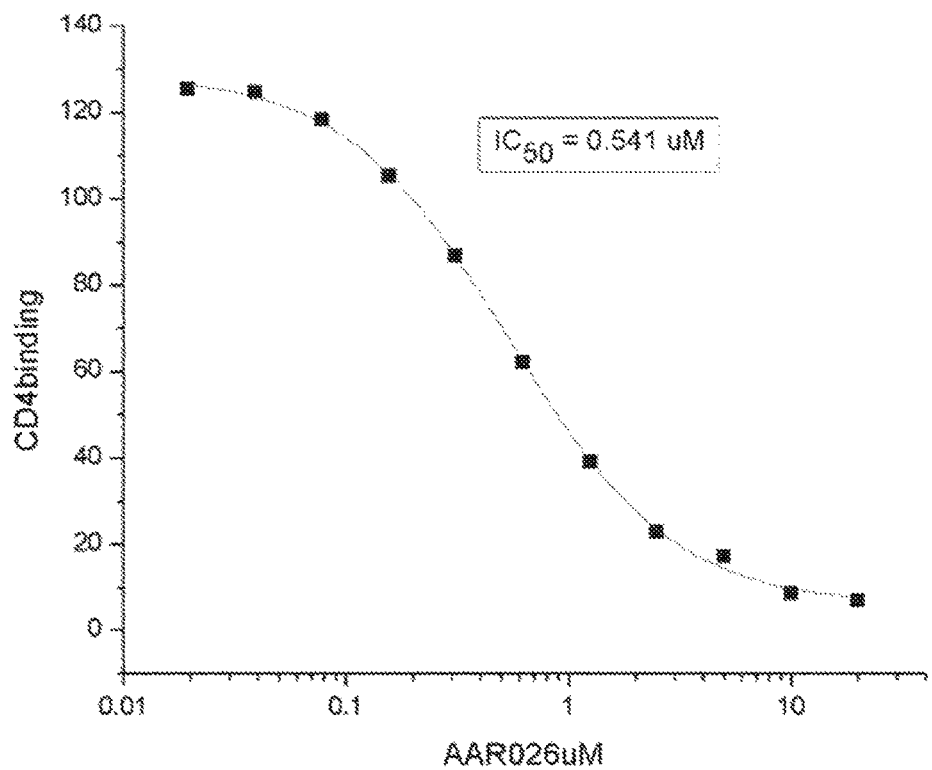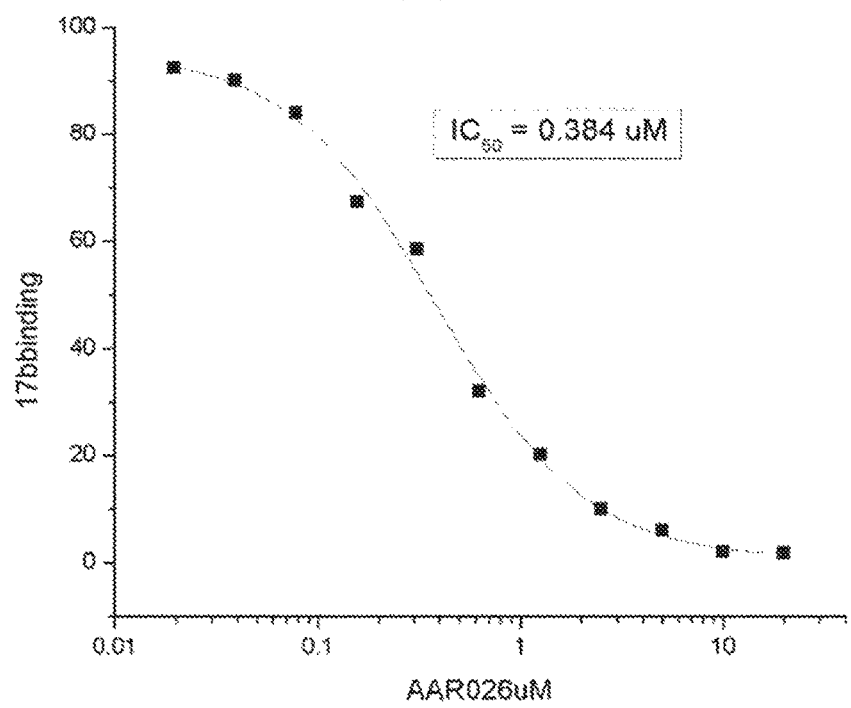
Fig. 5b

AAR029

Fig. 6b
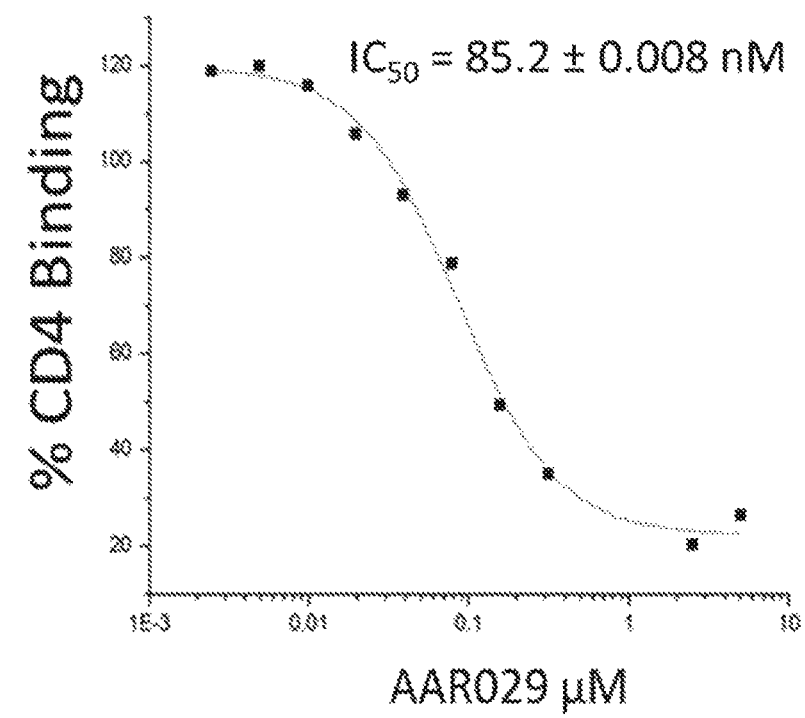
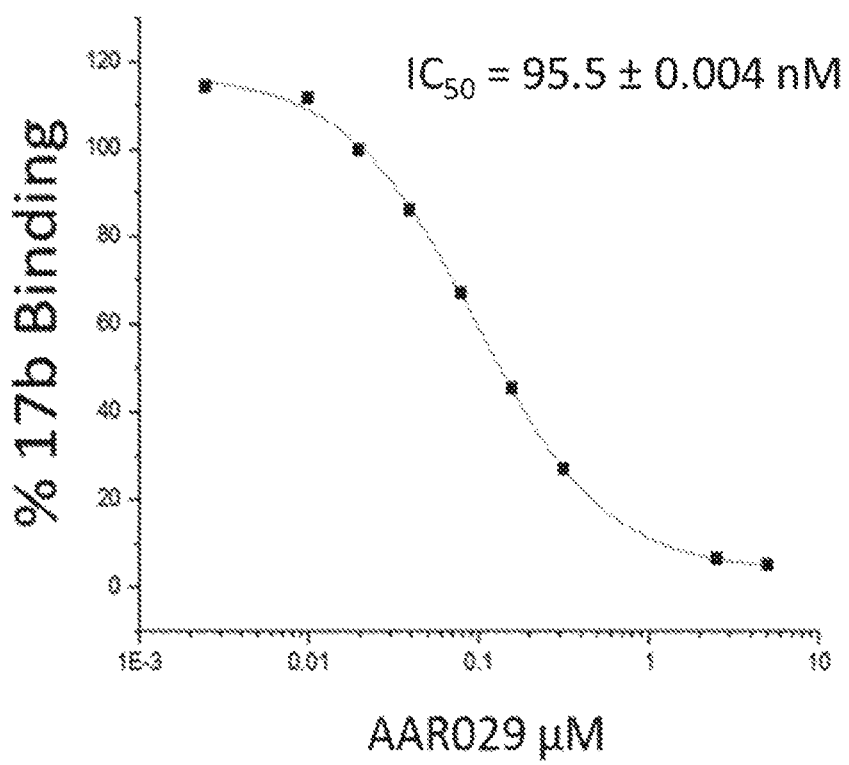

Fig. 10

| Compound | SPR competition IC50 (nM) | | HIV-1 infection inhibition IC50 (nM) | |
|---|---|---|---|---|
| | sCD4 inhibition | 17b inhibition | Bal.01 | JR-FL |
| AAR024 | 138 | 269 | | |
| AAR024A | 7890 | 11300 | | |
| AAR024b | 40 | 37.6 | 650±70 | 603±98 |
| AAR026 | 541 | 384 | | |
| AAR028 | A | A | | |
| AAR029 | 85 | 96 | 2018±95 | 2330±538 |
| AAR029b | 32 | 35 | 210±12 | 190±34 |
| AAR029b-Chg | - | - | ~90 | |
| AAR029E | ~20 | ~20 | 26 | |
| AAR029F | ~200 | ~200 | ~1300 | |
| AAR029H | ~318 | ~245 | ~1900 | |
| AAR029J | Inactive | Inactive | | |
| AAR030 | A | A | | |
| AAR031 | 5700 | 3900 | | |
| AAR032 | 500 | 400 | | |
| AAR036 | ~2000 | ~2000 | | |
| AAR039 | ~770 | ~770 | | |
| AAR040 | ~5000 | ~2000 | | |
| AAR042 | ~2000 | ~2000 | | |

A = measurable activity, estimated to be > 20,000 nM

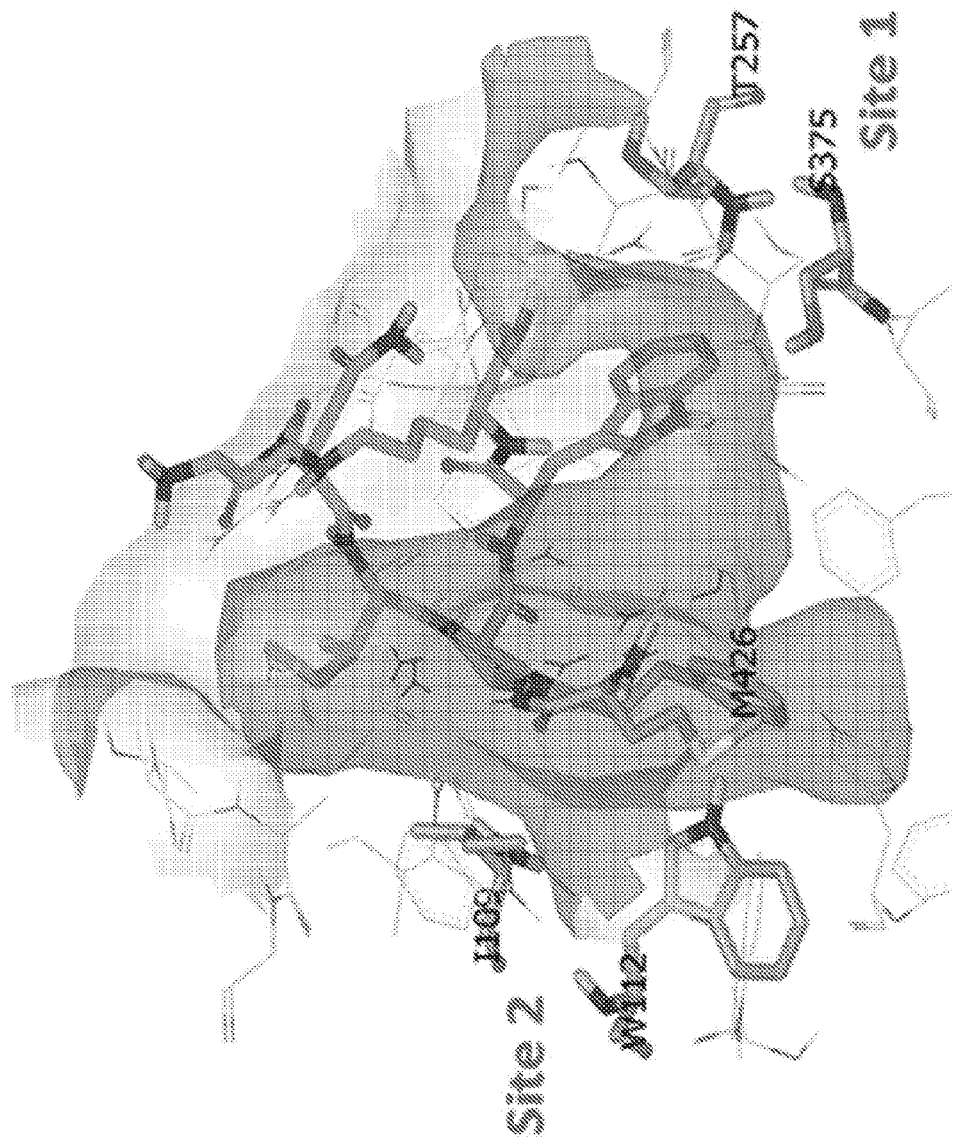

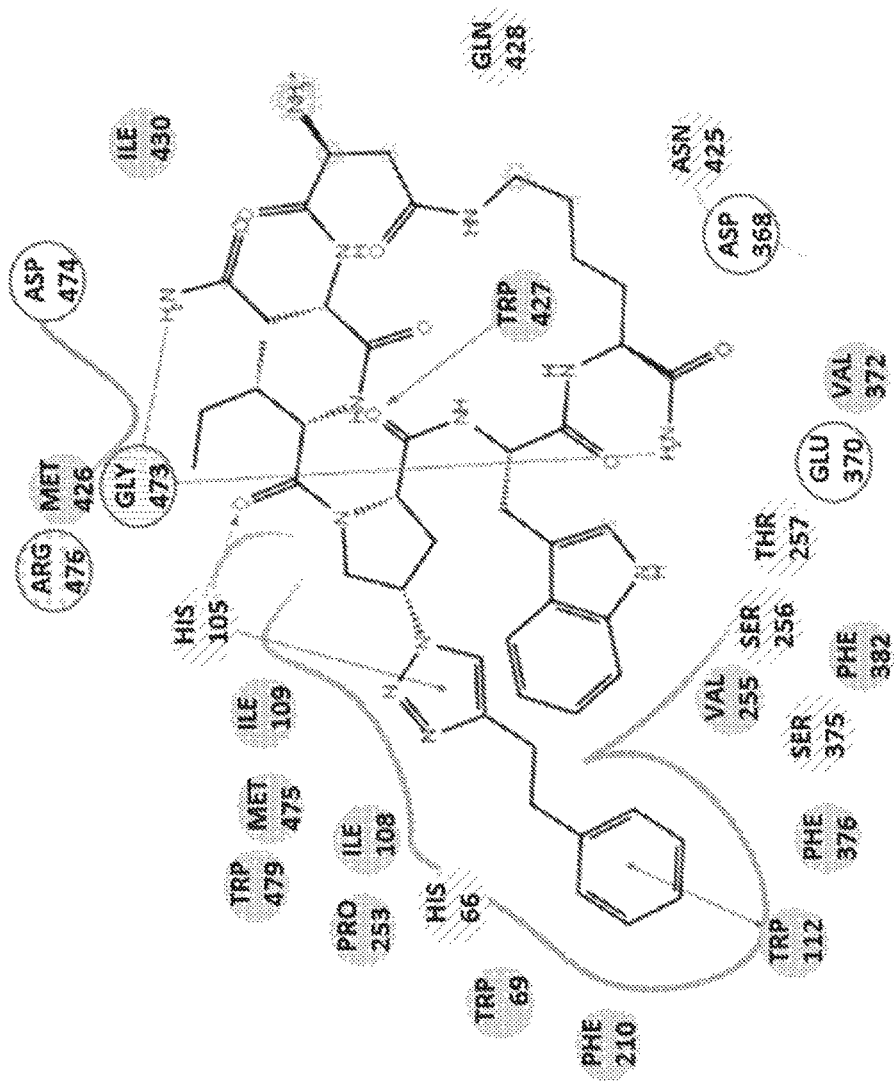

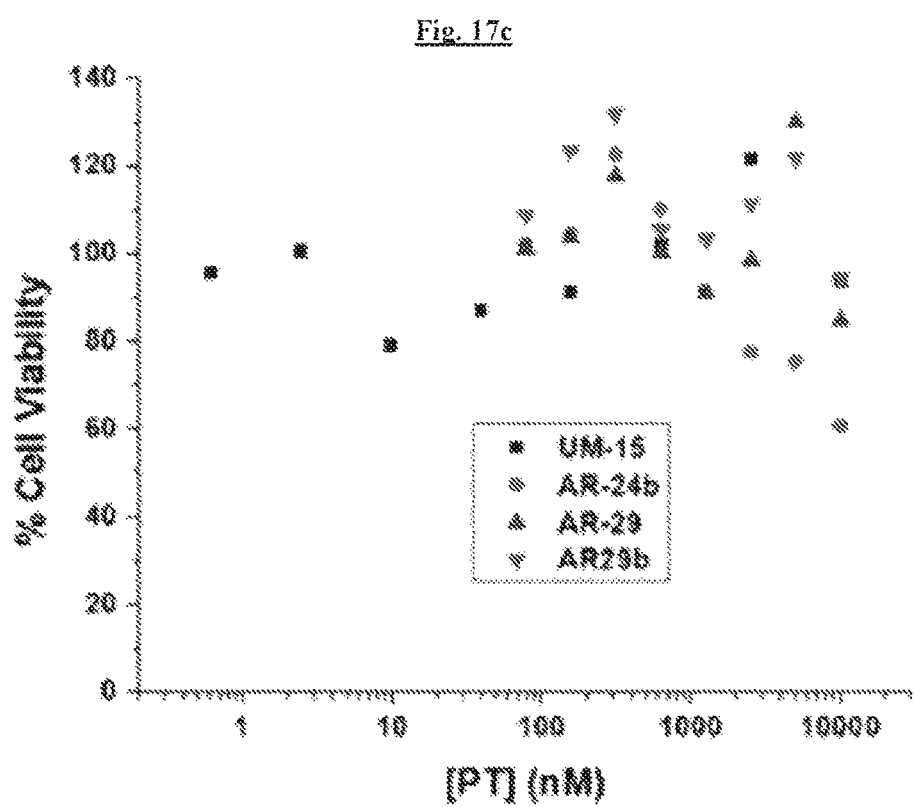

CYCLIC PEPTIDES AND METHODS USING SAME

CROSS-REFERENCE TO RELATED APPLICATIONS

The present application is a 35 U.S.C. § 371 national phase application from, and claims priority to, International Application No. PCT/US2015/064708, filed Dec. 9, 2015, and published under PCT Article 21(2) in English, which claims priority under 35 U.S.C. § 119(e) to U.S. Provisional Application No. 62/089,294, filed Dec. 9, 2014, all of which applications are incorporated herein by reference in their entireties.

STATEMENT REGARDING FEDERALLY SPONSORED RESEARCH OR DEVELOPMENT

This invention was made with government support under GM056550 and GM111029 awarded by National Institutes of Health. The government has certain rights in the invention.

BACKGROUND OF THE INVENTION

The human immunodeficiency virus-1 (HIV-1) is responsible for a global epidemic, with over 33 million infected people worldwide. The lifecycle of HIV-1 has been extensively studied in the hope of identifying a therapeutic intervention that blocks viral transmission or viability. As an example, the Highly Active Anti-Retroviral Therapy (HAART) is a therapeutic approach targeting one or more stages of the HIV-1 life cycle. Favorable clinical results with HAART have shown that simultaneously targeting distinct stages of the viral life cycle may reduce the viral evolutionary escape mechanism that leads to drug resistance. Further, HAART may be more effective if administered simultaneously with other drugs that interrupt the initial entry stage of the virus life cycle. Unfortunately, existing entry inhibitors suffer from weak potency and toxicity issues.

The entry of HIV-1 into the host cell is mediated by interaction of a trimeric gp120/gp41 envelope (Env) protein complex with both cellular CD4 and chemokine co-receptor CCR5 or CXCR4. Each virus Env spike consists of a trimer of two non-covalently associated glycoproteins, an inner gp41 transmembrane protein and an outer gp120 protein. The first step of viral entry is the interaction with CD4, leading to structural changes in the virus Env spike and exposing the chemokine binding domains of gp120. A structural change in the envelope spike exposes the fusion peptide sequence of gp41 and enables the collapse of gp41 into a six-helix bundle, leading to downstream membrane fusion and productive infection.

The HNG class of triazole conjugated peptides was derived from the 12-mer parental peptide 12p1 by converting the proline at residue 6 of 12p1 into an azido-proline and performing copper-catalyzed (2+3) cycloaddition reactions of the azide with substituted acetylenes. As a class, the HNG compounds have enhanced binding affinity for HIV-1 gp120, and block both CD4 and co-receptor sites with great efficacy. The HNG compounds appear to trap the gp120 protein in a non-functional state, distinct from the flexible ground state of gp120 or the CD4 induced conformation, and thus effectively halt the entry process at the initial binding stages. Using pseudotyped HIV-1 as well as isolated recombinant protein mutants, a binding footprint for the ferrocenyl triazole peptides was found to involve D474 and T257. These residues are adjacent to but not directly overlapping the CD4 binding site, and also overlap residues important for BMS-806 inhibition and a recently identified neutralizing antibody epitope. All of the 12p1 family members tested to date inhibit the binding of gp120 to both sCD4 (in a seemingly non-competitive manner) and the co-receptor surrogate mAb17b.

As an example, the ferrocenyl triazole conjugate HNG156 [SEQ ID No:1, wherein X is (2,4)-4-(4-ferrocenyl-1H-1,2, 3-triazol-1-yl)pyrrolidine-2-carboxylic acid; also known as (S)-4-((S)-2-((S)-2-((2S,4S)-1-(L-arginyl-L-isoleucyl-L-asparaginyl-L-asparaginyl-L-alloisoleucyl)-4-(4-ferrocenyl-1H-1,2,3-triazol-1-yl)pyrrolidine-2-carboxamido)-3-(1H-indol-3-yl)propanamido)-3-hydroxypropanamido)-5-(((S)-1-(((S)-1-(((S)-1-amino-4-(methylthio)-1-oxobutan-2-yl)amino)-4-(methylthio)-1-oxobutan-2-yl)amino)-1-oxopropan-2-yl)amino)-5-oxopentanoic acid] binds to monomeric gp120 with a $K_D$ of 7 nM, in contrast to the 2,600 nM $K_D$ value of 12p1. HNG156 inhibition of the co-receptor binding site appears to be allosteric and involves conformational entrapment of Env gp120 into an inactivated state. HNG156 neutralizes viral infection by subtype A, B and C isolates ($IC_{50}$ range=0.08-62.5 µM), but not viruses pseudotyped with VSV-G. HNG156 also exhibits no detectable toxicity in a tissue explants model at concentrations up to 100 µM. Enhancement of lifetime and potency of the HNG compounds could improve their potential as therapeutic and microbicide agents.

There is a need in the art to develop novel compounds that are useful for treating or preventing HIV-1 infection. There is also a need in the art to develop novel virolytic agents, which could cause virus lysis and prevent viral infection even in the absence of cells. The present invention fulfills these needs.

BRIEF SUMMARY OF THE INVENTION

Provided herein are novel cyclic peptides useful for the treatment of HIV-1 infection, and pharmaceutical compositions comprising at least one of such compounds. The present invention further provides a method of treating, reducing or preventing HIV-1 infection in a mammal in need thereof. The present invention further provides a method of reducing the risk of HIV-1 infection in a mammal at risk of HIV-1 exposure. The present invention further provides a method of promoting virolysis of a virus. The present invention further provides a method of reducing the rate of or preventing entry of a virus into a cell of a mammal. The present invention further provides a method of preparing a derivatized gold nanoparticle.

The invention includes cyclic compounds of formula (I), or a salt, solvate, enantiomer or diastereoisomer thereof:

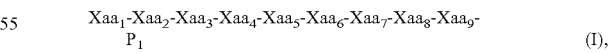

wherein $Xaa_1$-$Xaa_2$-$Xaa_3$-$Xaa_4$-$Xaa_5$-$Xaa_6$-$Xaa_7$-$Xaa_8$-$Xaa_9$ is SEQ ID No:2, and
wherein in (I):
$Xaa_1$ is selected from the group consisting of absent, Glu and Arg;
$Xaa_2$ is selected from the group consisting of absent, Gly, Phe, Lys, Asp, Glu, Ile, Arg and Cit;
$Xaa_3$ is selected from the group consisting of absent, Asn, Asp, Ile, Glu and 2-cyclohexylglycine;
$Xaa_4$ is selected from the group consisting of Asn and Asp;

Xaa₅ is a modified glycine of formula (III)

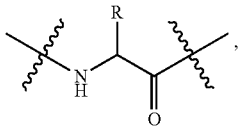

wherein in (III) R is selected from the group consisting of C₁-C₆ alkyl and C₃-C₆ cycloalkyl;

Xaa₆ is the modified proline of formula (IV)

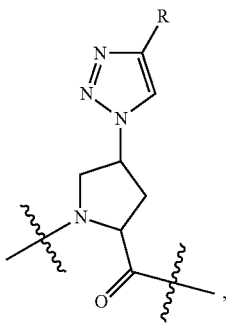

wherein in (IV) R is selected from the group consisting of naphthyl, p-methyl phenyl, p-ethyl phenyl, 2-phenylethyl, 1-adamantyl, 2-adamantyl and metallocene;

Xaa₇ is selected from the group consisting of Trp and 3-(3-benzothienyl)-L-alanine;

Xaa₈ is selected from the group consisting of Ser, Thr, 2,4-diaminobutanoic acid, Orn and Lys;

Xaa₉ is selected from the group consisting of absent, 2,4-diaminobutanoic acid, Orn, Lys, Glu, Glu-Ala, Glu-Ala-Met, Glu-Ala-Met-Met, and 2-(2-(2-aminoethoxy)ethoxy)acetic acid;

P₁ is absent, or is a group that comprises at least one thiol group and is covalently linked through an amide bond to (i) the C-terminus of Xaa₉ if Xaa₉ is not absent, or (ii) the C-terminus of Xaa₈ if Xaa₉ is absent;

the side chain amino group of one residue selected from the group consisting of 2,4-diaminobutanoic acid at Xaa₈, Orn at Xaa₈, Lys at Xaa₈, 2,4-diaminobutanoic acid at Xaa₉, Orn at Xaa₉, and Lys at Xaa₉ forms an amide bond with the side chain carboxylic acid group of one residue selected from the group consisting of Glu at Xaa₂, Asp at Xaa₂, Glu at Xaa₃, Asp at Xaa₃ and Asp at Xaa₄; and the C-terminus of Xaa₈ is optionally amidated if Xaa₉ and P₁ are absent, or the C-terminus of Xaa₉ is optionally amidated if P₁ is absent.

In certain embodiments, the cyclic compound is selected from the group consisting of:

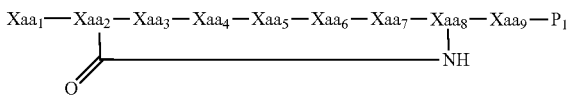
(Ia)

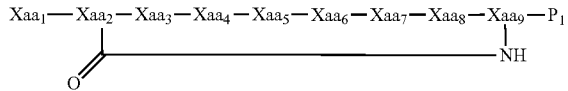
(Ib)

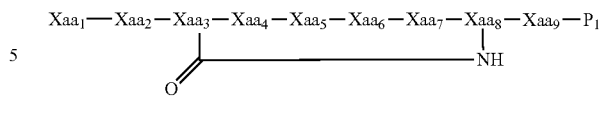
(Ic)

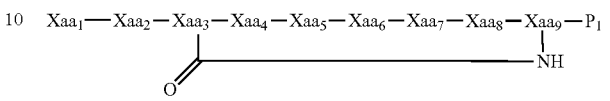
(Id)

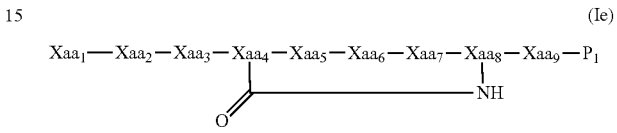
(Ie)

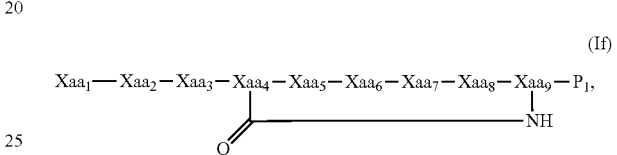
(If)

wherein in (Ia)-(If) 'NH' is derived from the side chain amino group of a residue selected from the group consisting of 2,4-diaminobutanoic acid at Xaa₈, Orn at Xaa₈, Lys at Xaa₈, 2,4-diaminobutanoic acid at Xaa₉, Orn at Xaa₉, and Lys at Xaa₉, and 'C=O' is derived from the side chain carboxylic acid group of a residue selected from the group consisting of Glu at Xaa₂, Asp at Xaa₂, Glu at Xaa₃, Asp at Xaa₃, and Asp at Xaa₄.

In certain embodiments, Xaa₅ is selected from the group consisting of Ile, Leu, norleucine (Nle), cyclopropylglycine, cyclobutylglycine, cyclopentylglycine and cyclohexylglycine.

In certain embodiments, the C-terminus of Xaa₈ is not amidated if Xaa₉ and P₁ are absent. In other embodiments, the C-terminus of Xaa₉ is not amidated if P₁ is absent.

In certain embodiments, the C-terminus of Xaa₈ is amidated if Xaa₉ and P₁ are absent. In other embodiments, the C-terminus of Xaa₉ is amidated if P₁ is absent.

In certain embodiments, the cyclic compound is the cyclic compound of formula (II):

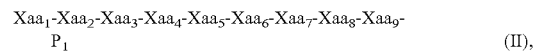
(II), wherein Xaa₁-Xaa₂-Xaa₃-Xaa₄-Xaa₅-Xaa₆-Xaa₇-Xaa₈-Xaa₉ is SEQ ID No:3, and wherein in (II):

Xaa₁ is selected from the group consisting of absent, Glu and Arg;

Xaa₂ is selected from the group consisting of absent, Gly, Phe, Lys, Asp, Glu, Ile, Arg and Cit;

Xaa₃ is selected from the group consisting of Asn, Asp, and Glu;

Xaa₄ is Asn;

Xaa₅ is Ile;

Xaa₆ is the modified proline of formula (IV)

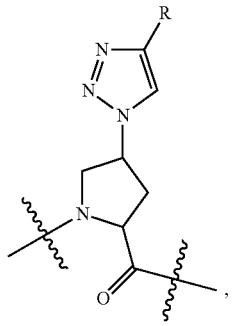

wherein in (IV) R is selected from the group consisting of naphthyl, p-methyl phenyl, p-ethyl phenyl, 2-phenylethyl and metallocene;

Xaa₇ is Trp;

Xaa₈ is selected from the group consisting of Ser, Thr, 2,4-diaminobutanoic acid, Orn and Lys;

Xaa₉ is selected from the group consisting of absent, 2,4-diaminobutanoic acid, Orn, Lys, Glu, Glu-Ala, Glu-Ala-Met, Glu-Ala-Met-Met, and 2-(2-(2-aminoethoxy)ethoxy) acetic acid;

P₁ is absent, or is a group that comprises at least one thiol group and is covalently linked through an amide bond to (i) the C-terminus of Xaa₉ if Xaa₉ is not absent or (ii) the C-terminus of Xaa₈ if Xaa₉ is absent;

the side chain amino group of one residue selected from the group consisting of 2,4-diaminobutanoic acid at Xaa₈, Orn at Xaa₈, Lys at Xaa₈, 2,4-diaminobutanoic acid at Xaa₉, Orn at Xaa₉, and Lys at Xaa₉ forms an amide bond with the side chain carboxylic acid group of one residue selected from the group consisting of Glu at Xaa₂, Asp at Xaa₂, Glu at Xaa₃, and Asp at Xaa₃ and the C-terminus of Xaa₈ is optionally amidated if Xaa₉ and P₁ are absent, or the C-terminus of Xaa₉ is optionally amidated if P₁ is absent.

In certain embodiments, P₁ is not absent. In other embodiments, P₁ comprises at least one cysteine residue. In yet other embodiments, P₁ comprises at least one natural or unnatural amino acid. In yet other embodiments, P₁ is a peptide consisting of at least two natural or unnatural amino acids. In yet other embodiments, P₁ is selected from the group consisting of:

βAla Gln βAla Cys-NH₂ (SEQ ID No:21);

βAla Gln βAla Cys (SEQ ID No:22);

$NH_2(CH_2CH_2O)_{0-10}CH_2C(=O)NHCH(CH_2SH)C(=O)OH$, $NH_2(CH_2CH_2O)_{0-10}CH_2C(=O)NHCH(CH_2SH)C(=O)NH_2$, $NH_2(CH_2)_{0-12}CH_2C(=O)NHCH(CH_2SH)C(=O)OH$, $NH_2(CH_2)_{0-12}CH_2C(=O)NHCH(CH_2SH)C(=O)NH_2$, and $NH_2CH_2CH_2OCH_2CH_2OC(=O)NHCH(CH_2SH)C(=O)NH_2$.

In certain embodiments, the compound is selected from the group consisting of:

AAR024 ((3S,6S,15S,18S,21S,25S,26aS)-3-((1H-indol-3-yl)methyl)-18-(2-amino-2-oxoethyl)-15-((2S,3S)-2-amino-3-methylpentanamido)-21-((S)-sec-butyl)-1,4,12,16,19,22-hexaoxo-25-(4-phenethyl-1H-1,2,3-triazol-1-yl)hexacosahydropyrrolo[2,1-f][1,4,7,10,13,19]hexaazacyclotetracosine-6-carboxamide), AAR026 (2,2'-((3S,6S,15S,18S,21S,24S,28S,29aS)-3-((1H-indol-3-yl)methyl)-15-amino-24-((S)-sec-butyl)-6-carbamoyl-1,4,12,16,19,22,25-heptaoxo-28-(4-phenethyl-1H-1,2,3-triazol-1-yl)octacosahydro-1H-pyrrolo[2,1-f][1,4,7,10,13,16,22]heptaazacycloheptacosine-18,21-diyl)diacetamide), AAR029 ((3S,6S,14S,17S,20S,24S,25aS)-3-((1H-indol-3-yl)methyl)-14-amino-17-(2-amino-2-oxoethyl)-20-((S)-sec-butyl)-1,4,12,15,18,21-hexaoxo-24-(4-phenethyl-1H-1,2,3-triazol-1-yl)tetracosahydro-1H-pyrrolo[2,1-f][1,4,7,10,13,18]hexaazacyclotricosine-6-carboxamide), AAR030 ((3S,6S,13S,16S,19S,23S,24aS)-3-((1H-indol-3-yl)methyl)-13-amino-16-(2-amino-2-oxoethyl)-19-((S)-sec-butyl)-1,4,10,14,17,20-hexaoxo-23-(4-phenethyl-1H-1,2,3-triazol-1-yl)tetracosahydropyrrolo[1,2-g][1,4,7,10,13,17]hexaazacyclodocosine-6-carboxamide), AAR031 ((3S,6S,13S,16S,19S,23S,24aS)-3-((1H-indol-3-yl)methyl)-13-amino-16-(2-amino-2-oxoethyl)-19-((S)-sec-butyl)-1,4,11,14,17,20-hexaoxo-23-(4-phenethyl-1H-1,2,3-triazol-1-yl)tetracosahydropyrrolo[2,1-f][1,4,7,10,13,18]hexaazacyclodocosine-6-carboxamide), AAR032 ((3S,6S,15S,18S,22S,23aS)-3-((1H-indol-3-yl)methyl)-12-amino-15-(2-amino-2-oxoethyl)-18-((S)-sec-butyl)-1,4,10,13,16,19-hexaoxo-22-(4-phenethyl-1H-1,2,3-triazol-1-yl)docosahydro-1H-pyrrolo[1,2-g][1,4,7,10,13,17]hexaazacyclohenicosine-6-carboxamide), AAR024B ((3S,6S,15S,18S,21S,25S,26aS)-3-((1H-indol-3-yl)methyl)-18-(2-amino-2-oxoethyl)-15-((2S,3S)-2-amino-3-methylpentanamido)-21-((S)-sec-butyl)-25-(4-ferrocenyl-1H-1,2,3-triazol-1-yl)-1,4,12,16,19,22-hexaoxohexacosahydropyrrolo[2,1-f][1,4,7,10,13,19]hexaazacyclotetracosine-6-carboxamide), AAR029B ((3S,6S,14S,17S,20S,24S,25aS)-3-((1H-indol-3-yl)methyl)-14-amino-17-(2-amino-2-oxoethyl)-20-((S)-sec-butyl)-24-(4-ferrocenyl-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide), AAR029b-Chg ((3S,6S,14S,17S,20S,24S,25aS)-3-((1H-indol-3-yl)methyl)-14-amino-17-(2-amino-2-oxoethyl)-20-cyclohexyl-24-(4-ferrocenyl-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide), AAR029E ((3S,6S,14S,17S,20S,24S,25aS)-14-amino-17-(2-amino-2-oxoethyl)-3-(benzo[b]thiophen-3-ylmethyl)-20-(sec-butyl)-24-(4ferrocenyl-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide), AAR036 ((3S,6S,14S,17S,20S,24S,25aS)-3-((1H-indol-3-yl)methyl)-14-amino-17-(2-amino-2-oxoethyl)-20-butyl-24-(4-ferrocenyl-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide), AAR029F ((3S,6S,14S,17S,20S,24S,25aS)-3-((1H-indol-3-yl)methyl)-24-(4-((1R,3S,5S,7S)-adamantan-2-yl)-1H-1,2,3-triazol-1-yl)-14-amino-17-(2-amino-2-oxoethyl)-20-(sec-butyl)-1,4,12,15,18,21-hexaoxotetracosahydro-1H-pyrrolo[2,1-f][1,4,7,10,13,18]hexaazacyclotricosine-6-carboxamide), AAR029H ((3S,6S,14S,17S,20S,24S,25aS)-3-((1H-indol-3-yl)methyl)-14-amino-17-(2-amino-2-oxoethyl)-20-((S)-sec-butyl)-24-(4-(4-ethylphenyl)-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide), AAR040 ((3S,6S,12S,15S,19S,20aS)-3-((1H-indol-3-yl)methyl)-12-amino-15-((S)-sec-butyl)-19-(4-ferrocenyl-1H-1,2,3-triazol-1-yl)-1,4,10,13,16-pentaoxoicosahydropyrrolo[1,2-d][1,4,7,10,14]pentaazacyclooctadecine-6-carboxamide) and AAR042 ((3S,6S,14S,17S,20S,24S,25aS)-3-((1H-indol-3-yl)methyl)-14-amino-17-(2-amino-2-oxoethyl)-20-cyclopropyl-24-(4-ferrocenyl-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide).

In other embodiments, the compound is selected from the group consisting of AAR024, AAR026 and AAR029.

In certain embodiments, $P_1$ is not absent and (I) is complexed through the at least one thiol group with at least one gold nanoparticle. In other embodiments, the at least one nanoparticle has an average diameter of about 20 nm.

In certain embodiments, the pharmaceutical composition further comprises at least one pharmaceutically acceptable carrier and a compound of formula I. In other embodiments, $P_1$ in (I) is not absent and (I) is complexed through the at least one thiol group with at least one gold nanoparticle.

In certain embodiments, the pharmaceutical composition further comprises at least one additional compound useful for treating viral infections. In other embodiments, the at least one additional compound is selected from the group consisting of antiviral combination drugs, entry and fusion inhibitors, integrase inhibitors, non-nucleoside reverse transcriptase inhibitors, nucleoside reverse transcriptase inhibitors, protease inhibitors, and any combinations thereof.

In certain embodiments, the peptide is encapsulated in a hydrogel and/or liposome. In other embodiments, the hydrogel and/or liposome is pH-responsive. In yet other embodiments, the hydrogel comprises a polymerized mixture of methacrylic acid and PEG-monomethyl ether monomethacrylate.

In certain embodiments, the method comprises administering to the mammal a therapeutically effective amount of at least one compound of the invention. In other embodiments, the mammal is further administered at least one additional compound useful for treating viral infections. In yet other embodiments, the mammal is human. In yet other embodiments, the virus comprises HIV-1. In yet other embodiments, the virus is HIV-1.

In certain embodiments, the method comprises contacting the nanoparticle with at least one compound of the invention to generate a reaction system; and isolating the derivatized gold nanoparticle from the reaction system.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2b comprises a schematic illustration of certain cyclic peptides of the invention (AAR031 or SEQ ID No:8; AAR032 or SEQ ID No:9; AAR024B or SEQ ID No:10; AAR029B or SEQ ID No:11). Each occurrence of X is independently a modified proline.

FIG. 2c comprises a schematic illustration of certain cyclic peptides of the invention (AAR029b-Chg or SEQ ID No:12; AAR029E or SEQ ID No:13; AAR036 or SEQ ID No:14; AAR029F or SEQ ID No:15). Each occurrence of X is independently a modified proline.

FIG. 2d comprises a schematic illustration of certain cyclic peptides of the invention (AAR029H or SEQ ID No:16; AAR040 or SEQ ID No:18; AAR042 or SEQ ID No:19), as well as a comparative cyclic peptide (AAR029J or SEQ ID No:18; also known as (3S,6S,14S,17S,20S,24S,25aS)-14-amino-17-(2-aminoethyl)-3-(benzo[b]thiophen-3-yl methyl)-20-cyclohexyl-24-(4-(4-ethylphenyl)-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide). Each occurrence of X is independently a modified proline.

FIG. 4a illustrates cyclic peptides of the invention and corresponding acyclic compounds (AAR024 or SEQ ID No:4; AAR024A or SEQ ID No:20).

FIGS. 4b-4c comprise a set of graphs illustrating the inhibition of binding of gp120 to CD4 or 17b by compounds illustrated in FIG. 4a.

FIG. 5b comprises a set of graphs illustrating the inhibition of binding of gp120 to CD4 or 17b by the compound illustrated in FIG. 5a.

FIG. 6b comprises a set of graphs illustrating the inhibition of binding of gp120 to CD4 or 17b by the compound illustrated in FIG. 6a.

FIG. 10 comprises a table listing the inhibition of binding of gp120 to CD4 and 17b by cyclic peptides of the invention, as well as HIV-1 infection inhibition against Bal.01 and JR-FL isolates.

FIGS. 16a-16b comprise depictions of computer-generated models for binding of AAR024 to gp120.

FIGS. 17a-17c comprise a set of graphs illustrating the infection inhibition against Bal.01 (FIG. 17a) and JR-FL (FIG. 17b) as well as the cytotoxicity (FIG. 17c) exhibited by AAR024b, AAR029, AAR029b and a non-cyclic peptide (UM15).

DETAILED DESCRIPTION OF THE INVENTION

Figure 1:
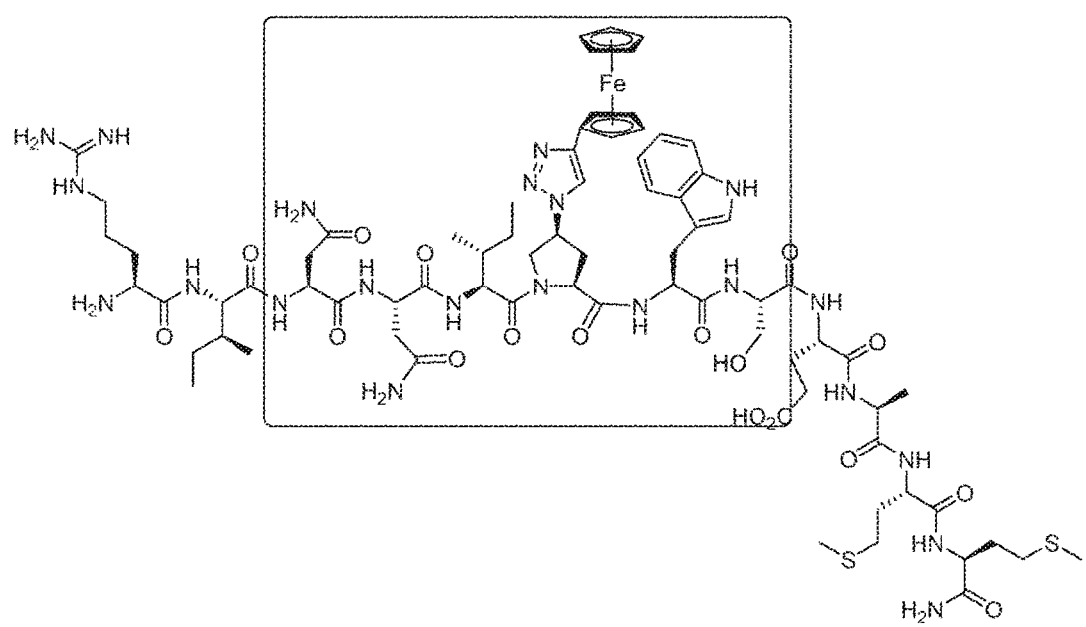
FIG. 1 comprises a schematic illustration of HNG156 (Arg Ile Asn Asn Ile X Trp Ser Glu Ala Met Met-NH$_2$; SEQ ID No:1), wherein X is a modified proline.

The present invention relates in one aspect to the unexpected discovery of novel gp120-targeting cyclic peptide antagonists that inhibit both CD4 and co-receptor binding sites. The invention also relates in another aspect to novel compositions comprising gold nanoparticles conjugated to the cyclic peptides of the invention, wherein the cyclic peptides comprise a thiol group.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, peptide chemistry, and organic chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration and the like, the term "about" is meant to encompass variations of ±20%, more preferably ±10%, more preferably ±5%, even more preferably ±1%, and still more preferably ±0.1% from the specified value, as such variations are appropriate to perform the disclosed methods.

As used herein, the term "antiviral agent" means a composition of matter that, when delivered to a cell, is capable of preventing replication of a virus in the cell, preventing infection of the cell by a virus, or reversing a physiological effect of infection of the cell by a virus. Antiviral agents are well known and described in the literature. By way of example, AZT (zidovudine, RETROVIR®, Glaxosmithkline, Middlesex, UK) is an antiviral agent that is thought to prevent replication of HIV in human cells.

"Applicator," as the term is used herein, is used to identify any device including, but not limited to, a hypodermic syringe, a pipette, and the like, for administering the compounds and compositions used in the practice of the invention.

As used herein, the term "βAla" or "bAla" refers to beta-alanine or 3-aminopropionic acid.

As used herein with respect to the compounds of the invention, "biologically active" means that the compounds elicit a biological response in a mammal that can be monitored and characterized in comparison with an untreated mammal. One possible biological response within the invention relates to the ability of the compound to avoid, reduce or treat HIV-1 infection in a mammal. In this particular case, the compound is administered to the mammal by an administration route selected from the group consisting of nasal, inhalational, topical, oral, buccal, rectal, pleural, peritoneal, vaginal, intramuscular, subcutaneous, transdermal, epidural, intratracheal, otic, intraocular, intrathecal and intravenous. The mammal and the HIV-1 viral load level in its body are monitored as a function of time, and the observation of a measurable and dose-dependent change in HIV-1 infection rate or viral load in the body is evidence that the compound displays biological activity. This preferred biological response does not limit or restrict the disclosures or embodiments of the invention in any way.

As used herein, the term "CM5" refers to carboxymethyl dextran.

As used herein, the term "container" includes any receptacle for holding the compounds and/or compositions of the invention. For example, in certain embodiments, the container is the packaging that contains the compounds and/or compositions of the invention. In other embodiments, the container is not the packaging that contains the compounds and/or compositions of the invention, i.e., the container is a receptacle, such as a box or vial that contains the compounds and/or compositions of the invention or unpackaged compounds and/or compositions of the invention and the instructions for use of the compounds and/or compositions of the invention. Moreover, packaging techniques are well known in the art. It should be understood that the instructions for use of the compounds and/or compositions of the invention may be contained on the packaging containing the compounds and/or compositions of the invention, and as such the instructions form an increased functional relationship to the packaged product. However, it should be understood that the instructions can contain information pertaining to the compound's ability to perform its intended function, e.g., treating, ameliorating, or preventing HIV-1 infection in a subject.

As used herein, the term "Dab" or "Dbu" refers to 2-diaminobutyric acid.

As used herein, the term "DCM" refers to dichloromethane.

As used herein, the term "Dde" refers to the protective group 1-(4,4-Dimethyl-2,6-dioxocyclohex-1-ylidene)ethyl.

As used herein, the term "DIC" refers to N,N'-diisopropylcarbodiimide.

As used herein, the term "DIPEA" refers to N,N-diisopropyl-ethylamine.

As used herein, the term "Dmab" refers to the protective group 4-(N-[1(4,4-Dimethyl-2,6-dioxocyclohexylidene)-3-methylbutyl] amino)benzyl ester.

As used herein, the term "DMF" refers to N,N-dimethylformamide.

As used herein, the term "EDC" refers to 1-ethyl-3-(3-dimethylaminopropyl) carbodiimide.

As used herein, the term "ESI-MS" refers to Electro-spray ionization mass spectrometry.

As used herein, the term "Fmoc" refers to 9-Fluorenylmethoxycarbonyl.

As used herein, the term "gp120 binder" refers to a small molecule, peptide or antibody that binds to the envelope protein gp120 of HIV-1.

As used herein, the term "HBTU" refers to O-benzotriazole-N,N,N',N'-tetramethyl-uronium-hexafluoro-phosphate.

As used herein, the term "HEK" refers to Human embryonic kidney.

As used herein, the term "HOBt" refers to 1-hydroxybenzotriazole.

As used herein, the term "HPLC" refers to High performance liquid chromatography.

As used herein, the term "IXW" refers to Ile-ferrocenyl-triazolePro-Trp.

As used herein, the term "medical intervention" means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

As used herein, "natural amino acids" are represented by the full name thereof, by the three-letter code, as well as the one-letter code corresponding thereto, as indicated in the following table. The structure of amino acids and their abbreviations can also be found in the chemical literature, such as in Stryer, 1988, "Biochemistry", 3$^{rd}$ Ed., W. H. Freeman and Co., New York.

| Full Name | Three-Letter Code | One-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "NHS" refers to N-hydroxysuccinimide.

As used herein, the term "Nle" refers to norleucine or (2S)-2-aminohexanoic acid.

As used herein, the term "non-natural amino acid" corresponds to an amino acid that is not the L-isomer of one of the natural alpha-amino acids listed herein. Non-natural amino acids include, but are not limited to, the D-isomer of a natural amino acid, $H_2N(CH_2CH_2O)_nCH_2CH_2COOH$ (wherein MW varies from ~1000 Da to 10000 Da), $H_2N(CH_2)_nCOOH$ (wherein n is an integer that varies from 3 to 8), arginosuccinic acid, citrulline, cysteine sulfinic acid, 3,4-dihydroxy-phenylalanine, homocysteine, homoserine, ornithine, hydroxylysine, 4-hydroxy-proline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexyl-alanine, N-methyl-norleucine, 3,4-dehydroproline, N,N-dimethylaminoglycine, N-methylaminoglycine, 4-aminopiperidine-4-carboxylic acid, 6-aminocaproic acid (also known as Acp or 6-aminohexanoic acid), 6-aminocapramide (also known as AcpNH$_2$ or 6-aminohexanamide), beta-alanine (also known as bAla or βAla), bAlaNH$_2$ (or βAlaNH$_2$, and also known as 3-aminopropanamide), trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid. Preferentially, the non-natural amino acid is selected from the group consisting of Acp, AcpNH$_2$, bAla and bAlaNH$_2$.

As used herein, the term "NP" refers to nanoparticle.

As used herein, the term "Orn" refers to ornithine or 2,5-diaminopentanoic acid. In certain embodiments, Orn corresponds to (+)-(S)-2,5-diaminopentanoic acid.

As used herein, the term "Oxyma" refers to ethyl cyano (hydroxyimino)acetate.

As used herein, the term "PBS" refers to phosphate buffered saline.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic has a N-terminus and a C-terminus. The N-terminus has an amino group, which may be free (i.e., as a NH$_2$ group) or appropriately protected (e.g., with a BOC or a Fmoc group). The C-terminus has a carboxylic group, which may be free (i.e., as a COOH group) or appropriately protected (e.g., as a benzyl or a methyl ester). A cyclic peptide does not necessarily have free N- or C-termini, since they are covalently bonded through an amide bond to form the cyclic structure.

As used herein, a "pharmaceutically acceptable carrier" means a pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; gar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, a "prophylactic" or "preventive" treatment is a treatment administered to a subject who does not exhibit signs of a disease or disorder or exhibits only early signs of the disease or disorder for the purpose of decreasing the risk of developing pathology associated with the disease or disorder.

As used herein, the term "PT" refers to peptide triazole.

As used herein, the term "SDS-page" refers to sodium dodecyl sulfate-polyacrylamide gel electrophoresis.

As used herein, the term "SPR" refers to surface plasmon resonance.

As used herein, a "subject" or a "mammal" includes a human or a non-human mammal. Non-human mammals include, for example, livestock and pets, such as ovine, bovine, porcine, canine, feline and murine mammals. Preferably, the subject or mammal is human.

As used herein, the term "tBu" refers to tert-butyl.

As used herein, the term "TFA" refers to Trifluoroacetic acid.

As used herein, a "therapeutic" treatment is a treatment administered to a subject who exhibits signs of pathology of a disease or disorder for the purpose of diminishing or eliminating those signs.

As used herein, the language "therapeutically effective amount" or "effective amount" refers to a non-toxic but sufficient amount of the composition used in the practice of the invention that is effective to treat, prevent or ameliorate HIV-1 infection in the body of a mammal. The desired treatment may be prophylactic and/or therapeutic. That result may be reduction and/or alleviation of the signs, symptoms, or causes of a disease or disorder, or any other desired alteration of a biological system. An appropriate therapeutic amount in any individual case may be determined by one of ordinary skill in the art using routine experimentation.

As used herein, the term "treating" means ameliorating the effects of, or delaying, halting or reversing the progress of a disease or disorder. The word encompasses reducing the severity of a symptom of a disease or disorder and/or the frequency of a symptom of a disease or disorder.

As used herein, the term "Trt" refers to triphenylmethyl.

As used herein, the term "viral envelope protein binder" refers to a small molecule, peptide or antibody that binds to at least one envelope protein of a virus.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 5 2.7, 3, 4, 5, 5.1, 5.3, 5.5, and 6. This applies regardless of the breadth of the range.

Description

The invention relates to a novel class of gp120-targeting cyclic peptide antagonists that inhibit both CD4 and co-receptor binding sites. The invention further relates to novel compositions comprising gold nanoparticles conjugated to the cyclic peptides of the invention, wherein the cyclic peptides comprise a thiol group.

Figure 12:
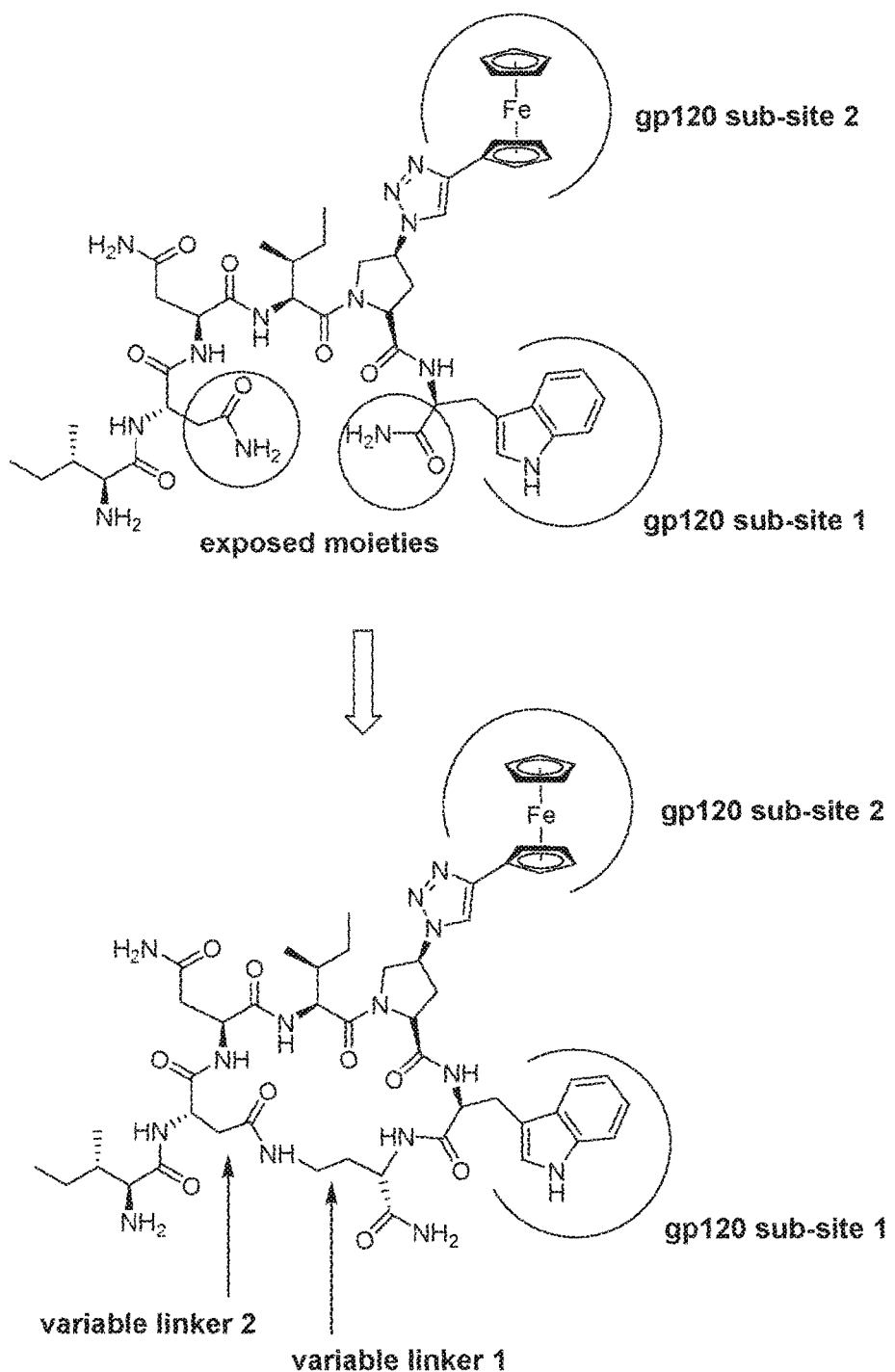
FIG. 12 comprises a diagram of two six-residue peptides illustrating a side chain to side chain cyclization.

As demonstrated herein, a linear peptide with demonstrated antiviral activity (FIG. 12) had its conformation constrained by connecting the C terminus of the peptide with an exposed Asn-2 side chain. Lys was first selected as a possible C terminus extension, as the four carbons in its side chain provide a flexible linker required to reach the Asn-2 side chain at the N terminus. Moreover, the amine group of the Lys side chain can be utilized for a covalent bond through amide formation. At the N terminus, residue Asn-2 was initially mutated to Glu (and also to Asp), providing a carboxylic acid functionality for amide formation.

For the synthesis of cyclic PT, the N terminal Asn-2 residue or the He-1 (FIG. 14) of the previously synthesized linear PTs were replaced with a Glu residue, in which the (COOH) side chain was protected by ODmab. Lys (Dde protected side chain $NH_2$) was also added at the C terminal next to the Trp residue. The orthogonal on-resin deprotection of both $_{Glu}COOH$ and $_{Lys}NH_2$ with 2% hydrazine in DMF afforded the free COOH and $NH_2$. On-resin side chain to side chain cyclization was successful using microwave synthesizer coupling conditions. On-resin click reaction followed by cleavage/global deprotection and HPLC purification (to >95% purity) yielded the cyclic PTs. Peptide purity was confirmed using analytical $C_{18}$ RP-HPLC column with a gradient of (20-95% ACN)/$H_2O$/0.1% TFA over 42 min run time, with a flow rate of 2 mL min$^{-1}$ and UV absorbance at 280 nm. AAR024 and AAR026 not only retained the dual receptor site inhibitory signature of linear PTs but also displayed enhanced potency compared to the linear analogues. AAR024 was found to be >40-fold more active than the linear AAR024A. Similarly, minimized hexapeptide AAR029 was >200-fold more active than AAR029A.

Figure 14:
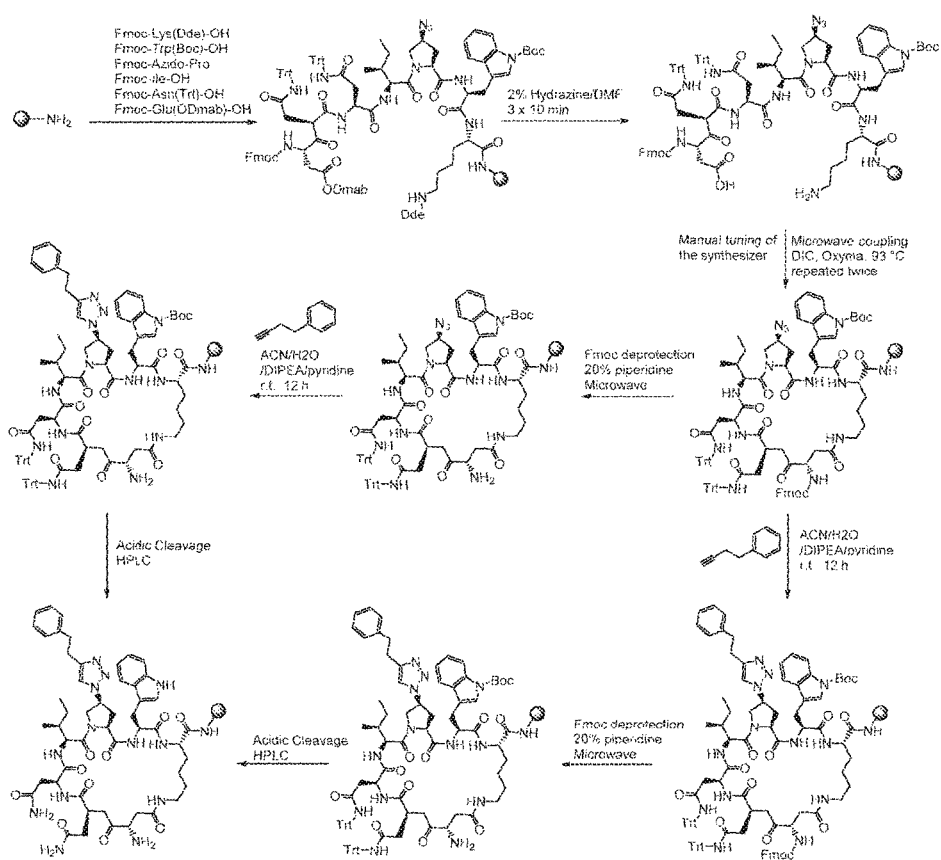
FIG. 14 comprises a synthetic scheme depicting the synthesis of AAR026.

The cyclic heptapeptide AAR024 was further optimized via a series of stepwise modifications (FIG. 14). SPR competition binding assays were used to assess the structural elements required for cyclic hexapeptide binding to gp120. The N terminal Ile was trimmed to obtain a cyclic hexapeptide AAR028, which was found to be inactive at the concentration range used ($IC_{50}$>40 µM). Without wishing to be limited by any theory, this may take place due to the loss of contacts with the protein upon deletion of the N terminal Ile. In an attempt to restore the lost contact, the length of the two linkers was changed (Linker 1 and Linker 2 in FIG. 12). Shortening Linker 1 using only two carbon spacers also resulted in inactive macrocycle AAR030. However, incorporating a shorter Linker 2, by using Asp instead of Glu during the peptide synthesis, resulted in almost 2-fold enhanced activity in macrocycle AAR029 vs AAR029b. This enhancement might be related to the improved positioning of the macrocycle relative to its binding site on gp 120. Further optimization of AAR029 was sought by stepwise shortening of Linker 1. Incorporating a three-carbon linker, using Orn-(Dde), resulted in decreased but not lost activity [AAR031, micro molar $IC_{50}$ value]. However, further shortening with a two-carbon linker, using Dab(ivDde), resulted in regaining of activity with almost 10-fold improvement [AAR032 vs AAR031]. These results reflect the sensitivity of target binding to changes in Linker 1 length.

Further, it was found that ferrocenyl cPTs, AAR024b and AAR029b (FIG. 14) showed enhanced dual receptor site antagonizing activities compared to their nonferrocene analogues. Without wishing to be limited by any theory, the bulky ferrocene may stack within the inner domain hydrophobic cavity, therefore enhancing inhibitor binding affinity.

Figure 13:
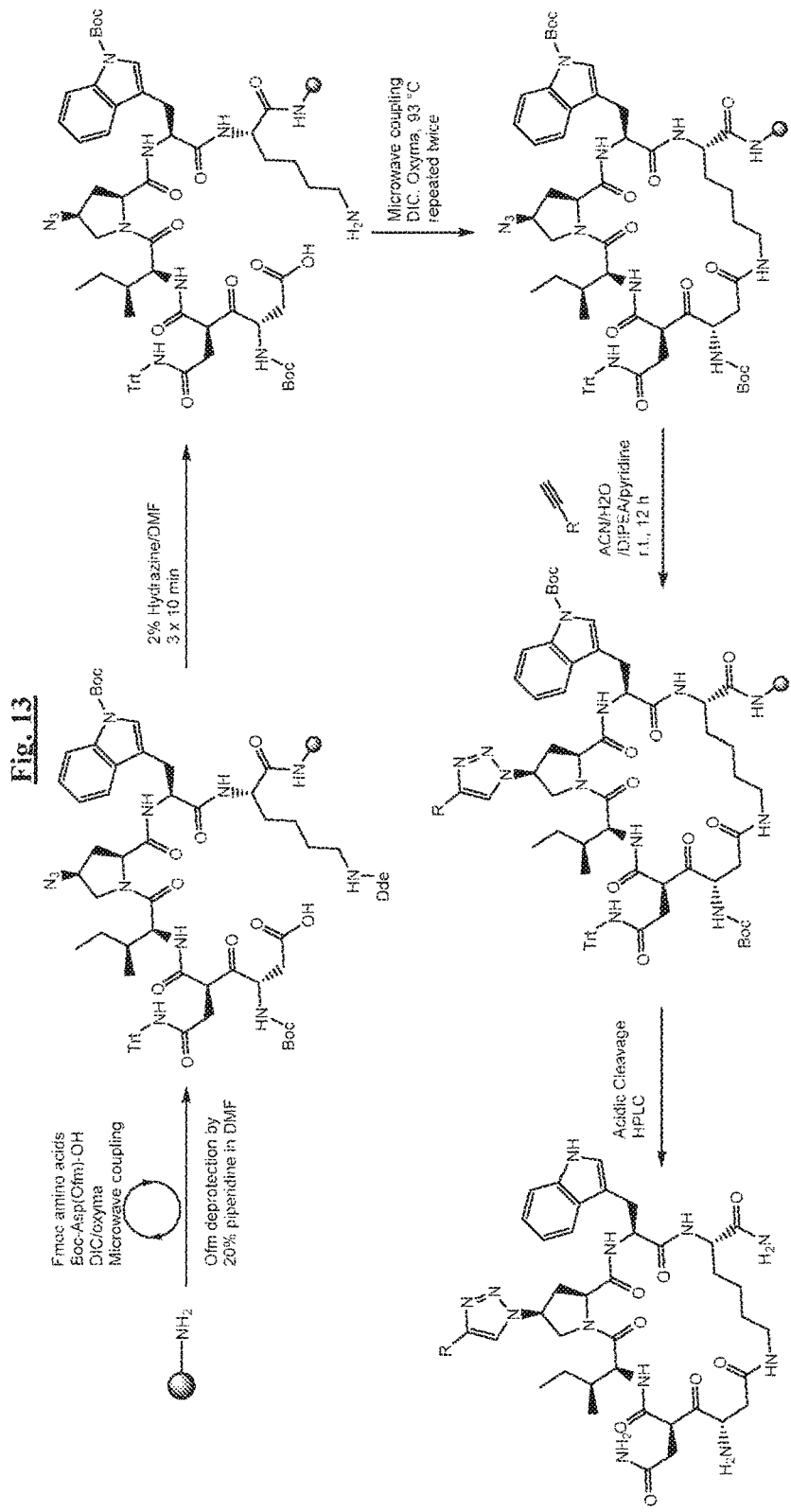
FIG. 13 comprises a synthetic scheme depicting the synthesis of AAR029 and AAR029b.

On the basis of the increased activities of cyclic hexapeptides AAR029 and AAR029b, these compounds were further refined through a synthetic route (FIG. 13) using Boc-Asp(Ofm)-OH at the N terminal. After peptide assembly using microwave synthesis, the Asp carboxylic group was deprotected by 20% piperidine in DMF during the final microwave deprotection step. The peptide-bound resin was then subjected to selective deprotection conditions (2% hydrazine in DMF, 3×40 mL×10 min) to deprotect the Lys NH$_2$ group. Cyclization was achieved using two microwave coupling steps. Click reaction with the alkyne followed by acidic deprotection/cleavage yielded the crude peptides. This modified method (FIG. 13) is cheaper and affords improved yields by at least 3-fold compared to the initially described methods, hence representing a simple route to access the highly active class of macro cyclic HIV-1 inhibitors.

Figure 11:
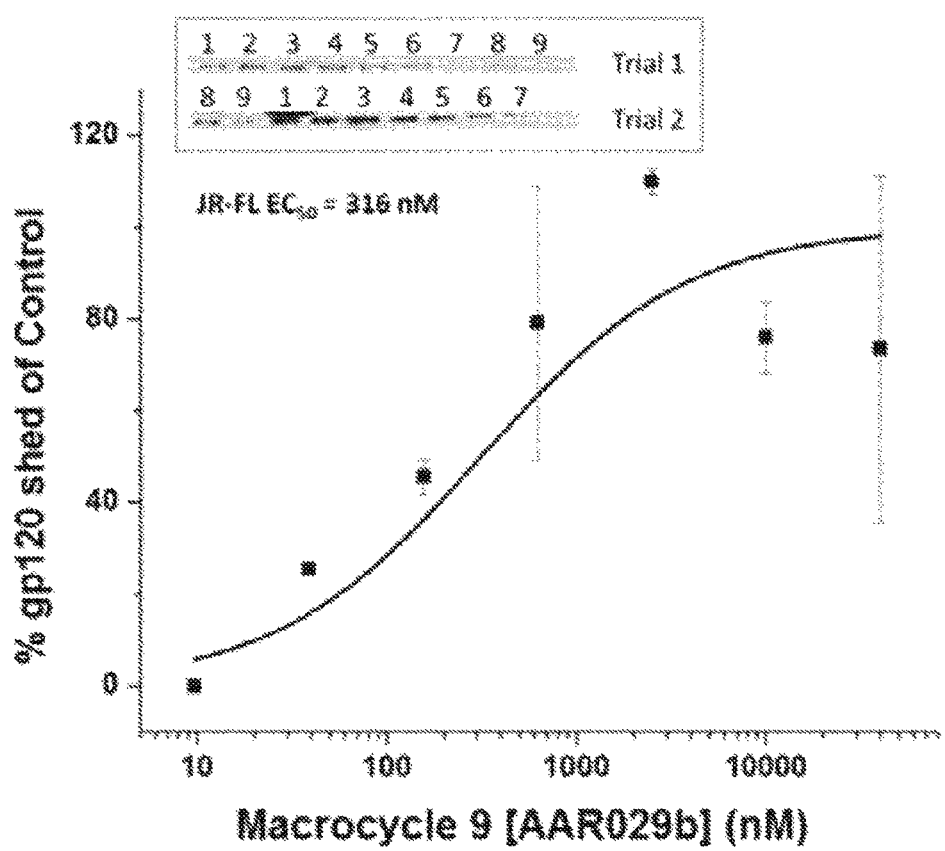
FIG. 11 comprises a graph illustrating a dose-dependent gp120 shedding of JR-FL pseudotyped HIV-1 virus upon treatment with AAR029b.
Figure 17A:
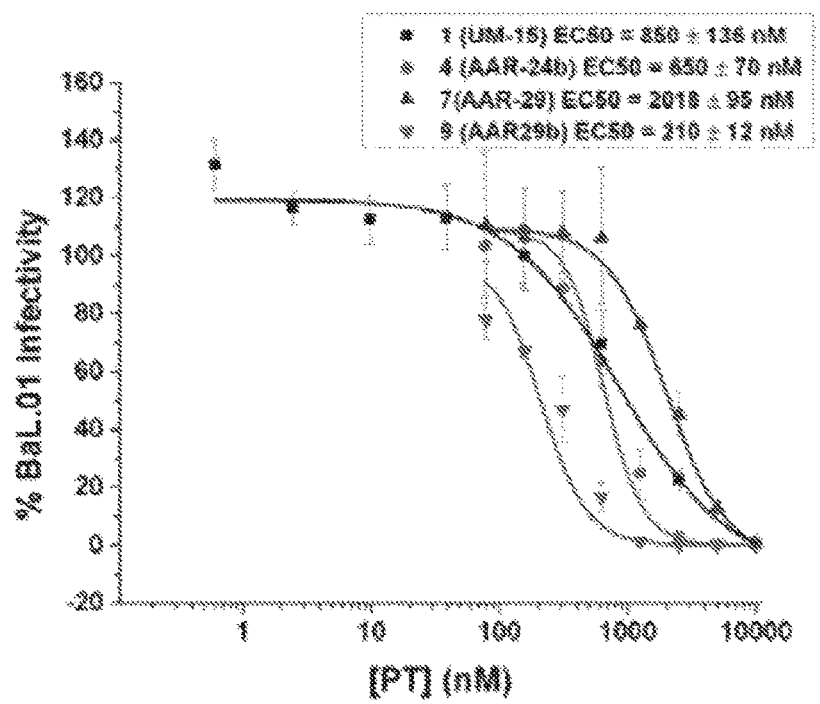
Figure 17B:
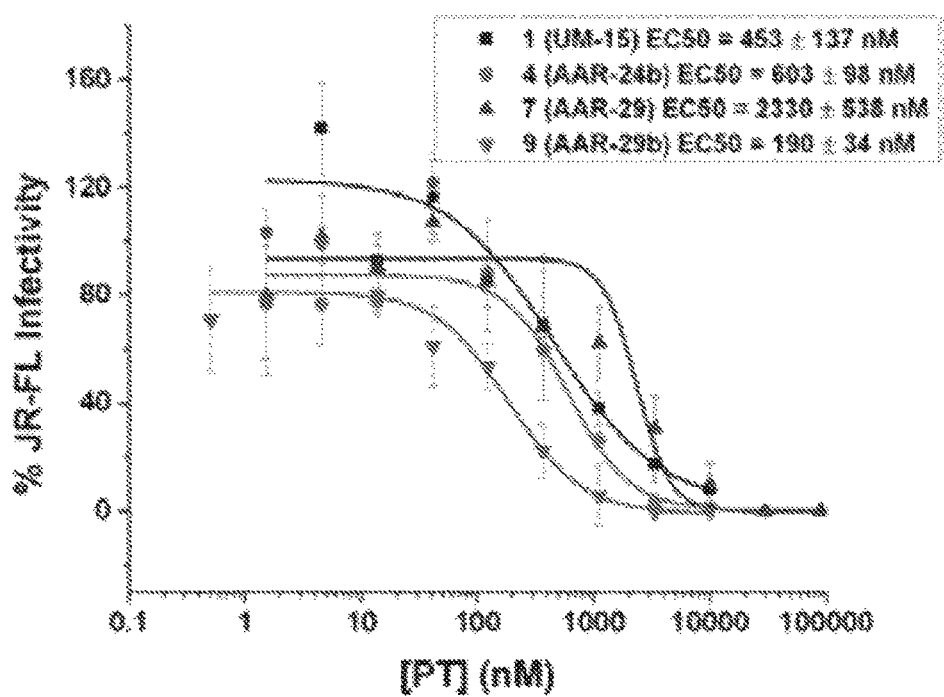

The molecular-level inhibitory activities of the cPTs against HIV-1 gp120 glycoproteins indicate that they may be used as HIV-1 infection inhibitors. The most active cPT derivatives were evaluated (FIG. 10) against a laboratory adapted strain of HIV-1, Bal.01, and a more resistant strain, JR-FL. The metallocene containing cPT AAR029b was able to inhibit the two strains at submicromolar concentrations, demonstrating improved potency compared to the parent linear peptide. Macrocycle AAR029b was also found to trigger gp 120 shedding, leaving a naked noninfectious virion, with an EC$_{50}$ value of 316 nM for the JR-FL strain (FIG. 11), in agreement with its infection inhibition IC$_{50}$ value (FIG. 10). The functionality of macrocycle AAR029b makes it the most potent hexapeptide triazole (linear or cyclic) identified. The nonferrocenyl cPT AAR029 was less potent than AAR029b, yet still remained among the most potent hexapeptides tested. Without wishing to be limited by any theory, the ability of the cPTs to inhibit both viral strains tested, including the more difficult-to-inhibit tier 2 JR-FL subtype, suggests that cPTs likely retain the breadth of function already observed for linear PTs. Using WST-1 assay, no significant cell cytotoxicity was observed (FIG. 17c), even at the highest concentrations used for the infection inhibition analysis.

Figure 15:
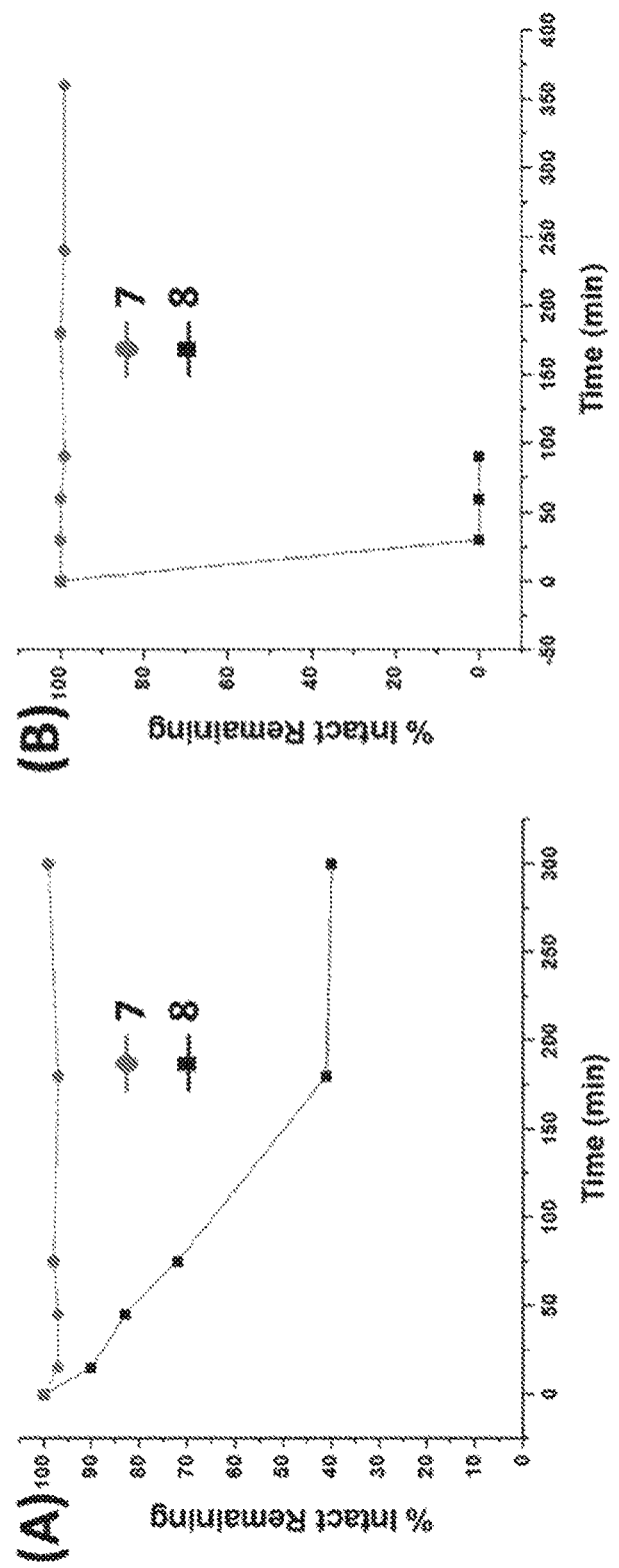
FIG. 15 comprises charts depicting digestion of AAR029 (labelled as 7) and AAR029A (labelled as 8) by trypsin (panel A) and chymotrypsin (panel B).

In certain embodiments, cyclizing PTs eliminates proteolytic susceptibility, which may be a major obstacle in developing certain peptides into marketed therapeutics despite their high potencies and selectivities. The in vitro stability of the cPT AAR029 was compared to that of its linear analogue AAR029A against two specific proteases, trypsin and chymotrypsin. The designed cyclic peptides have a trypsin-sensitive Lys amide group incorporated for cyclization and also have chymotrypsin-sensitive Trp and Ile residues within their sequences. The two peptides were incubated separately with each of the two enzymes at 37° C. and HPLC and ESI-MS were used to monitor the digestion reactions. The results showed striking differences (FIG. 15). The macrocycle AAR029 was completely resistant to both trypsin and chymotrypsin during the 5 h incubations used. In contrast, almost 60% of the corresponding linear peptide AAR029A (FIG. 15) was cleaved after 5 h at the C terminal amide as detected by ESI-MS. The linear peptide AAR029A was even more unstable with chymotrypsin treatment (FIG. 15), wherein 100% of the peptide was hydrolyzed after only a 30 min incubation time compared to almost unchanged cPT AAR029. Because of the difference between the linear and the cyclic peptides, the intactness of the macrocycle AAR029 was reassessed after 20 h and also 40 h of chymotrypsin digestion. It was found that the cyclic peptide remained intact even after 40 h incubation as monitored by HPLC and ESI-MS. Overall, these experiments demonstrated the in vitro stability of the cyclized peptide vs the linear analogue and the consequent ability to greatly reduce the proteolytic susceptibility by macrocycle formation.

To rationalize the retention of PT functions by cPTs, molecular modeling was used to investigate the possible interactions between cPT and envelope HIV-1 gp120. Among the gp 120 crystal structures available, the recently reported trimeric SOSIP structure (pdb: 4NCO) was chosen, as it represents the gp120 in a non-CD4-bound Env protein in a trimeric form that has been surmised to be close to the structure in the native viral spike. Flexible docking was used, in which some protein side chains at the binding site along with the peptide were allowed to move during the simulation. Flexible docking can reveal a more plausible binding mode than rigid-docking alone, allowing rearrangements of the protein scaffold in order to better accommodate the docked ligand. This docking approach was assessed to be suitable for the highly flexible nature of HIV-1 envelope protein, which can adopt multiple conformations. The peptide Pro-4 backbone carbonyl accepts a H-bond (1.93 Å) from the β$_{20/21}$ loop $_{gp120}$Trp-427 backbone NH. Peptide Ile-3 carbonyl also forms a 1.73 Å H-bond with gp$_{120}$His105 side chain imidazole NH. The π-π stacking plays a role in complex stabilization, where the peptide phenyl-ethyl stacked with gp$_{120}$Trl12 and the peptide triazole ring stacked with gp$_{120}$His105.

In certain embodiments of this invention, AuNPs (20 nm) can be synthesized using a one-step aqueous method leading to particles with a narrow size distribution (±4 nm) as characterized using UV-Vis spectroscopy, dynamic light scattering (DLS) and transmission electron microscopy (TEM). In other embodiments, multivalent peptide-AuNP significantly improve the inhibition potency of the cyclic peptide alone. In yet other embodiments, the conjugate increases viral envelop shedding compared to peptide alone. In yet other embodiments, nanoparticle conjugation increases the potency of cyclic peptides of the invention in both inhibiting the virus-cell infection and inactivating the virus itself. The cyclic peptides of the invention, as well as their complexes with gold nanoparticles, may be used as microbicidal and therapeutic agents.

Compounds

The invention includes cyclic compounds of formula (I), or a salt, solvate, enantiomer or diastereoisomer thereof:

Xaa$_1$-Xaa$_2$-Xaa$_3$-Xaa$_4$-Xaa$_5$-Xaa$_6$-Xaa$_7$-Xaa$_8$-Xaa$_9$-P$_1$  (I)

wherein Xaa$_1$-Xaa$_2$-Xaa$_3$-Xaa$_4$-Xaa$_5$-Xaa$_6$-Xaa$_7$-Xaa$_8$-Xaa$_9$ is SEQ ID No:2, and
wherein in (I):
Xaa$_1$ is selected from the group consisting of absent, Glu and Arg;
Xaa$_2$ is selected from the group consisting of absent, Gly, Phe, Lys, Asp, Glu, Ile, Arg and Cit;
Xaa$_3$ is selected from the group consisting of absent, Asn, Asp, Ile, Glu and 2-cyclohexylglycine;
Xaa$_4$ is selected from the group consisting of Asn and Asp;
Xaa$_5$ is a modified glycine of formula (III)

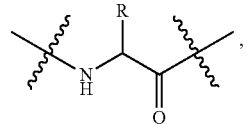

wherein in (III) R is selected from the group consisting of C$_1$-C$_6$ alkyl and C$_3$-C$_6$ cycloalkyl;

Xaa$_6$ is the modified proline of formula (IV)

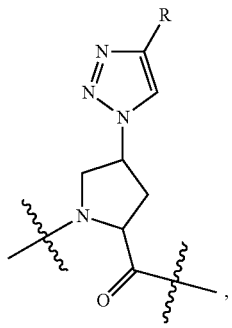

wherein in (IV) R is selected from the group consisting of naphthyl, p-methyl phenyl, p-ethyl phenyl, 2-phenylethyl, 1-adamantyl, 2-adamantyl and metallocene;

Xaa$_7$ is selected from the group consisting of Trp and 3-(3-benzothienyl)-L-alanine;

Xaa$_8$ is selected from the group consisting of Ser, Thr, 2,4-diaminobutanoic acid, Orn and Lys;

Xaa$_9$ is selected from the group consisting of absent, 2,4-diaminobutanoic acid, Orn, Lys, Glu, Glu-Ala, Glu-Ala-Met, Glu-Ala-Met-Met, and 2-(2-(2-aminoethoxy)ethoxy)acetic acid;

P$_1$ is absent, or is a group that comprises at least one thiol group and is covalently linked through an amide bond to (i) the C-terminus of Xaa$_9$ if Xaa$_9$ is not absent, or (ii) the C-terminus of Xaa$_8$ if Xaa$_9$ is absent;

the side chain amino group of one residue selected from the group consisting of 2,4-diaminobutanoic acid at Xaa$_8$, Orn at Xaa$_8$, Lys at Xaa$_8$, 2,4-diaminobutanoic acid at Xaa$_9$, Orn at Xaa$_9$, and Lys at Xaa$_9$ forms an amide bond with the side chain carboxylic acid group of one residue selected from the group consisting of Glu at Xaa$_2$, Asp at Xaa$_2$, Glu at Xaa$_3$, Asp at Xaa$_3$ and Asp at Xaa$_4$; and the C-terminus of Xaa$_8$ is optionally amidated if Xaa$_9$ and P$_1$ are absent, or the C-terminus of Xaa$_9$ is optionally amidated if P$_1$ is absent.

In certain embodiments, the cyclic compound is selected from the group consisting of:

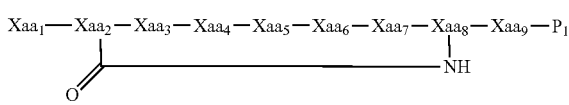
(Ia)

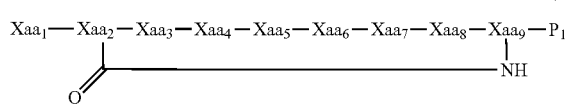
(Ib)

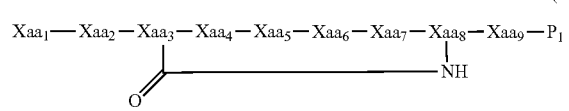
(Ic)

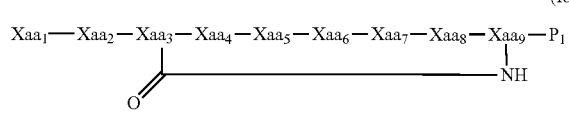
(Id)

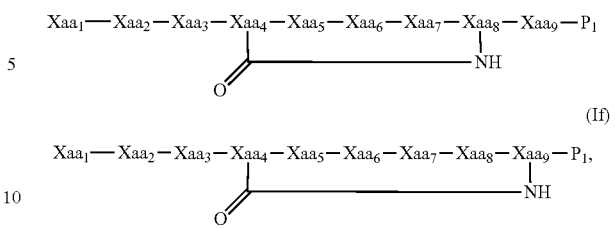

(Ie)

(If)

wherein in (Ia)-(If):

'NH' is derived from the side chain amino group of a residue selected from the group consisting of 2,4-diaminobutanoic acid at Xaa$_8$, Orn at Xaa$_8$, Lys at Xaa$_8$, 2,4-diaminobutanoic acid at Xaa$_9$, Orn at Xaa$_9$, and Lys at Xaa$_9$, and 'C=O' is derived from the side chain carboxylic acid group of a residue selected from the group consisting of Glu at Xaa$_2$, Asp at Xaa$_2$, Glu at Xaa$_3$, Asp at Xaa$_3$, and Asp at Xaa$_4$.

In certain embodiments, the C-terminus of Xaa$_8$ is not amidated if Xaa$_9$ and P$_1$ are absent. In other embodiments, the C-terminus of Xaa$_9$ is not amidated if P$_1$ is absent.

In certain embodiments, the C-terminus of Xaa$_8$ is amidated if Xaa$_9$ and P$_1$ are absent. In other embodiments, the C-terminus of Xaa$_9$ is amidated if P$_1$ is absent.

In certain embodiments, Xaa$_5$ is selected from the group consisting of Ile, Leu, Nle, cyclopropylglycine, cyclobutylglycine, cyclopentylglycine and cyclohexylglycine.

In certain embodiments, the cyclic compound is the cyclic compound of formula (II):

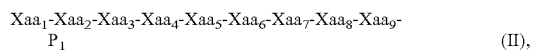
(II), wherein Xaa$_1$-Xaa$_2$-Xaa$_3$-Xaa$_4$-Xaa$_5$-Xaa$_6$-Xaa$_7$-Xaa$_8$-Xaa$_9$ is SEQ ID No:3, wherein in (II):

Xaa$_1$ is selected from the group consisting of absent, Glu and Arg;

Xaa$_2$ is selected from the group consisting of absent, Gly, Phe, Lys, Asp, Glu, Ile, Arg and Cit;

Xaa$_3$ is selected from the group consisting of Asn, Asp, and Glu;

Xaa$_4$ is Asn;

Xaa$_5$ is Ile;

Xaa$_6$ is the modified proline of formula (IV)

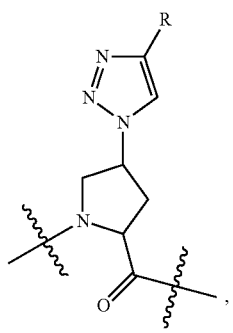

wherein in (IV) R is selected from the group consisting of naphthyl, p-methyl phenyl, p-ethyl phenyl, 2-phenylethyl and metallocene;

Xaa₇ is Trp;

Xaa₈ is selected from the group consisting of Ser, Thr, 2,4-diaminobutanoic acid, Orn and Lys;

Xaa₉ is selected from the group consisting of absent, 2,4-diaminobutanoic acid, Orn, Lys, Glu, Glu-Ala, Glu-Ala-Met, Glu-Ala-Met-Met, and 2-(2-(2-aminoethoxy)ethoxy) acetic acid;

P₁ is absent, or is a group that comprises at least one thiol group and is covalently linked through an amide bond to (i) the C-terminus of Xaa₉ if Xaa₉ is not absent or (ii) the C-terminus of Xaa₈ if Xaa₉ is absent;

the side chain amino group of one residue selected from the group consisting of 2,4-diaminobutanoic acid at Xaa₈, Orn at Xaa₈, Lys at Xaa₈, 2,4-diaminobutanoic acid at Xaa₉, Orn at Xaa₉, and Lys at Xaa₉ forms an amide bond with the side chain carboxylic acid group of one residue selected from the group consisting of Glu at Xaa₂, Asp at Xaa₂, Glu at Xaa₃, and Asp at Xaa₃ and the C-terminus of Xaa₈ is optionally amidated if Xaa₉ and P₁ are absent, or the C-terminus of Xaa₉ is optionally amidated if P₁ is absent.

In certain embodiments, P₁ is not absent. In other embodiments, P₁ comprises at least one cysteine residue. In yet other embodiments, P₁ comprises at least one natural or unnatural amino acid. In yet other embodiments, P₁ is a peptide consisting of at least two natural or unnatural amino acids. In yet other embodiments, P₁ is selected from the group consisting of: βAla Gln βAla Cys-NH₂, βAla Gln βAla Cys, NH₂(CH₂CH₂O)₀₋₁₀CH₂C(=O)NHCH(CH₂SH)C(=O)OH, NH₂(CH₂CH₂O)₀₋₁₀CH₂C(=O)NHCH(CH₂SH)C(=O)NH₂, NH₂(CH₂)₀₋₁₂CH₂C(=O)NHCH(CH₂SH)C(=O)OH, NH₂(CH₂)₀₋₁₂CH₂C(=O)NHCH(CH₂SH)C(=O)NH₂, and NH₂CH₂CH₂OCH₂CH₂OC(=O)NHCH(CH₂SH)C(=O)NH₂.

In certain embodiments, the compound is selected from the group consisting of:

AAR024 ((3S,6S,15S,18S,21S,25S,26aS)-3-((1H-indol-3-yl)methyl)-18-(2-amino-2-oxoethyl)-15-((2S,3S)-2-amino-3-methylpentanamido)-21-((S)-sec-butyl)-1,4,12,16,19,22-hexaoxo-25-(4-phenethyl-1H-1,2,3-triazol-1-yl)hexacosahydropyrrolo[2,1-f][1,4,7,10,13,19]hexaazacyclotetracosine-6-carboxamide), AAR026 (2,2'-((3S,6S,15S,18S,21S,24S,28S,29aS)-3-((1H-indol-3-yl)methyl)-15-amino-24-((S)-sec-butyl)-6-carbamoyl-1,4,12,16,19,22,25-heptaoxo-28-(4-phenethyl-1H-1,2,3-triazol-1-yl)octacosahydro-1H-pyrrolo[2,1-f][1,4,7,10,13,16,22]heptaazacycloheptacosine-18,21-diyl)diacetamide), AAR029 ((3S,6S,14S,17S,20S,24S,25aS)-3-((1H-indol-3-yl)methyl)-14-amino-17-(2-amino-2-oxoethyl)-20-((S)-sec-butyl)-1,4,12,15,18,21-hexaoxo-24-(4-phenethyl-1H-1,2,3-triazol-1-yl)tetracosahydro-1H-pyrrolo[2,1-f][1,4,7,10,13,18]hexaazacyclotricosine-6-carboxamide), AAR030 ((3S,6S,13S,16S,19S,23S,24aS)-3-((1H-indol-3-yl)methyl)-13-amino-16-(2-amino-2-oxoethyl)-19-((S)-sec-butyl)-1,4,10,14,17,20-hexaoxo-23-(4-phenethyl-1H-1,2,3-triazol-1-yl)tetracosahydropyrrolo[1,2-g][1,4,7,10,13,17]hexaazacyclodocosine-6-carboxamide), AAR031 ((3S,6S,13S,16S,19S,23S,24aS)-3-((1H-indol-3-yl)methyl)-13-amino-16-(2-amino-2-oxoethyl)-19-((S)-sec-butyl)-1,4,11,14,17,20-hexaoxo-23-(4-phenethyl-1H-1,2,3-triazol-1-yl)tetracosahydropyrrolo[2,1-f][1,4,7,10,13,18]hexaazacyclodocosine-6-carboxamide), AAR032 ((3S,6S,15S,18S,22S,23aS)-3-((1H-indol-3-yl)methyl)-12-amino-15-(2-amino-2-oxoethyl)-18-((S)-sec-butyl)-1,4,10,13,16,19-hexaoxo-22-(4-phenethyl-1H-1,2,3-triazol-1-yl)docosahydro-1H-pyrrolo[1,2-g][1,4,7,10,13,17]hexaazacyclohenicosine-6-carboxamide), AAR024B ((3S,6S,15S,18S,21S,25S,26aS)-3-((1H-indol-3-yl)methyl)-18-(2-amino-2-oxoethyl)-15-((2S,3S)-2-amino-3-methylpentanamido)-21-((S)-sec-butyl)-25-(4-ferrocenyl-1H-1,2,3-triazol-1-yl)-1,4,12,16,19,22-hexaoxohexacosahydropyrrolo[2,1-f][1,4,7,10,13,19]hexaazacyclotetracosine-6-carboxamide), AAR029B ((3S,6S,14S,17S,20S,24S,25aS)-3-((1H-indol-3-yl)methyl)-14-amino-17-(2-amino-2-oxoethyl)-20-((S)-sec-butyl)-24-(4-ferrocenyl-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide), AAR029b-Chg ((3S,6S,14S,17S,20S,24S,25aS)-3-((1H-indol-3-yl)methyl)-14-amino-17-(2-amino-2-oxoethyl)-20-cyclohexyl-24-(4-ferrocenyl-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide), AAR029E ((3S,6S,14S,17S,20S,24S,25aS)-14-amino-17-(2-amino-2-oxoethyl)-3-(benzo[b]thiophen-3-ylmethyl)-20-(sec-butyl)-24-(4ferocenyl-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide), AAR036 ((3S,6S,14S,17S,20S,24S,25aS)-3-((1H-indol-3-yl)methyl)-14-amino-17-(2-amino-2-oxoethyl)-20-butyl-24-(4-ferrocenyl-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide), AAR029F ((3S,6S,14S,17S,20S,24S,25aS)-3-((1H-indol-3-yl)methyl)-24-(4-((1R,3S,5S,7S)-adamantan-2-yl)-1H-1,2,3-triazol-1-yl)-14-amino-17-(2-amino-2-oxoethyl)-20-(sec-butyl)-1,4,12,15,18,21-hexaoxotetracosahydro-1H-pyrrolo[2,1-f][1,4,7,10,13,18]hexaazacyclotricosine-6-carboxamide), AAR029H ((3S,6S,14S,17S,20S,24S,25aS)-3-((1H-indol-3-yl)methyl)-14-amino-17-(2-amino-2-oxoethyl)-20-((S)-sec-butyl)-24-(4-(4-ethylphenyl)-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide), AAR040 ((3S,6S,12S,15S,19S,20aS)-3-((1H-indol-3-yl)methyl)-12-amino-15-((S)-sec-butyl)-19-(4-ferrocenyl-1H-1,2,3-triazol-1-yl)-1,4,10,13,16-pentaoxoicosahydropyrrolo[1,2-d][1,4,7,10,14]pentaazacyclooctadecine-6-carboxamide) and AAR042 ((3S,6S,14S,17S,20S,24S,25aS)-3-((1H-indol-3-yl)methyl)-14-amino-17-(2-amino-2-oxoethyl)-20-cyclopropyl-24-(4-ferrocenyl-1H-1,2,3-triazol-1-yl)-1,4,12,15,18,21-hexaoxotetracosahydro-1H-pyrrolo[2,1-f][1,4,7,10,13,18]hexaazacyclotricosine-6-carboxamide).

The invention further includes a cyclic peptide of the invention, or a salt or solvate thereof, wherein P₁ is not absent. In certain embodiments, the cyclic peptide is complexed through the at least one thiol group with at least one gold nanoparticle.

In certain embodiments, the at least one nanoparticle has an average diameter of about 20 nm. In other embodiments, the cyclic peptide of the invention complexed to the at least one gold nanoparticle is in a pharmaceutical composition. In yet other embodiments, the composition further comprises at least one pharmaceutically acceptable carrier. In yet other embodiments, the composition further comprises at least one additional compound useful for treating viral infections. In yet other embodiments, the at least one additional compound is selected from the group consisting of antiviral combination drugs, entry and fusion inhibitors, integrase inhibitors, non-nucleoside reverse transcriptase inhibitors, nucleoside reverse transcriptase inhibitors, protease inhibitors, and combinations thereof. In yet other embodiments, the peptide is encapsulated in a hydrogel and/or liposome. In yet other embodiments, the hydrogel and/or liposome is pH-responsive. In yet other embodiments, the hydrogel comprises a polymerized mixture of methacrylic acid and PEG-monomethyl ether monomethacrylate.

In certain embodiments, at least one compound of the invention is a component of a pharmaceutical composition further including at least one pharmaceutically acceptable carrier.

The compounds of the invention may possess one or more stereocenters, and each stereocenter may exist independently in either the (R)- or (S)-configuration. In certain embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, compounds described herein are prepared as prodrugs. A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$ a N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

Salts

The compositions described herein may form salts with acids or bases, and such salts are included in the present invention. In certain embodiments, the salts are pharmaceutically acceptable salts. The term "salts" embraces addition salts of free acids or free bases that are compositions of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compositions of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compositions of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding composition by reacting, for example, the appropriate acid or base with the composition.

Methods

The invention includes a method of treating, reducing or preventing HIV-1 infection in a mammal in need thereof. The method comprises administering to the mammal a therapeutically effective amount of a compound or composition of the invention.

The invention further includes a method of reducing the risk of HIV-1 infection in a mammal at risk of HIV-1 exposure. The method comprises administering to the mammal a therapeutically effective amount of a compound or composition of the invention.

The method further includes a method of preparing a derivatized gold nanoparticle, wherein the gold nanoparticle is complexed with a cyclic peptide of the invention, wherein the cyclic peptide comprises at least one thiol group. The method comprises contacting a solution of the cyclic peptide with the nanoparticle, to generate a reaction system. The method further comprises stirring the reaction system for an amount of time, whereby the derivatized gold nanoparticle is formed. The method further comprises isolating the derivatized gold nanoparticle from the reaction system.

The invention also includes a method of promoting virolysis of a virus. The method comprises contacting the virus with a therapeutically effective amount of a compound or composition of the invention. In certain embodiments, the virus is in a mammal, for example a human.

The invention further includes a method of reducing the rate of or preventing entry of a virus into a cell of a mammal. The method comprises administering to the mammal a therapeutically effective amount of a compound or composition of the invention.

In certain embodiments, the virus comprises HIV-1. In other embodiments, the virus is HIV-1.

In certain embodiments, the mammal is further administered at least one additional compound useful for treating viral infections. In other embodiments, the at least one additional compound is selected from the group consisting of antiviral combination drugs, entry and fusion inhibitors, integrase inhibitors, non-nucleoside reverse transcriptase inhibitors, nucleoside reverse transcriptase inhibitors, protease inhibitors, and combinations thereof. In yet other embodiments, the at least one additional compound and the peptide are co-formulated.

In certain embodiments, the peptide is encapsulated in a hydrogel and/or liposome. In other embodiments, the hydrogel and/or liposome is pH-responsive. In yet other embodiments, the hydrogel comprises a polymerized mixture of methacrylic acid and PEG-monomethyl ether monomethacrylate.

In certain embodiments, the composition is administered to a mammal by a route selected from the group consisting of nasal, inhalational, topical, oral, buccal, rectal, pleural, peritoneal, vaginal, intramuscular, subcutaneous, transdermal, epidural, intratracheal, otic, intraocular, intrathecal and intravenous. In yet other embodiments, the mammal is human.

Combination Therapies

The compositions of the invention are useful in the methods of the invention in combination with one or more additional compounds useful for treating viral infections, such as but not limited to HIV infections. These additional compounds may comprise compounds or compositions identified herein, or compounds (e.g., commercially available compounds) known to treat, prevent, or reduce the symptoms of viral infections.

In non-limiting examples, the compositions of the invention may be used in combination with one or more of the following anti-HIV drugs:

HIV Combination Drugs: efavirenz, emtricitabine or tenofovir disoproxil fumarate (ATRIPLa®/BMS, Gilead); lamivudine or zidovudine (COMBIVIR®/GSK); abacavir or lamivudine (EPZICOM®/GSK); abacavir, lamivudine or zidovudine (TRIZIVIR®/GSK); emtricitabine, tenofovir disoproxil fumarate (TRUVADA®/Gilead).

Entry and Fusion Inhibitors: maraviroc (CELSENTRI®, SELZENTRY®/Pfizer); pentafuside or enfuvirtide (FUZEON®/Roche, Trimeris).

Integrase Inhibitors: raltegravir or MK-0518 (ISENTRESS®/Merck).

Non-Nucleoside Reverse Transcriptase Inhibitors: delavirdine mesylate or delavirdine (RESCRIPTOR®/Pfizer); nevirapine (VIRAMUNE®/Boehringer Ingelheim); stocrin or efavirenz (SUSTIVA®/BMS); etravirine (INTELENCE®/Tibotec).

Nucleoside Reverse Transcriptase Inhibitors: lamivudine or 3TC (EPIVIR®/GSK); FTC, emtricitabina or coviracil (EMTRIVA®/Gilead); abacavir (ZIAGEN®/GSK); zidovudina, ZDV, azidothymidine or AZT (RETROVIR®/GSK); ddI, dideoxyinosine or didanosine (VIDEX®/BMS); abacavir sulfate plus lamivudine (EPZICOM®/GSK); stavudine, d4T, or estavudina (ZERIT®/BMS); tenofovir, PMPA prodrug, or tenofovir disoproxil fumarate (VIREAD®/Gilead).

Protease Inhibitors: amprenavir (AGENERASE®/GSK, Vertex); atazanavir (REYATAZ®/BMS); tipranavir (APTIVUS®/Boehringer Ingelheim); darunavir (PREZIST®/Tibotec); fosamprenavir (TELZIR®, LEXIVA®/GSK, Vertex); indinavir sulfate (CRIXIVAN®/Merck); saquinavir mesylate (INVIRASE®/Roche); lopinavir or ritonavir (KALETRA®/Abbott); nelfinavir mesylate (VIRACEPT®/Pfizer); ritonavir (NORVIR®/Abbott).

A synergistic effect may be calculated, for example, using suitable methods such as, for example, the Sigmoid-$E_{max}$ equation (Holford & Scheiner, 19981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

Routes of administration of any of the compounds and/or compositions of the invention include oral, nasal, rectal, intravaginal, parenteral (e.g., IM, IV and SC), buccal, sublingual or topical. The regimen of administration may affect what constitutes an effective amount. The therapeutic formulations may be administered to the subject either prior to or after the onset of a viral infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to treat a viral infection in the subject. An effective amount of the therapeutic compound necessary to achieve a therapeutic effect may vary according to factors such as the state of the disease or disorder in the subject; the age, sex, and weight of the subject; and the ability of the therapeutic compound to treat a viral infection in the subject. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound useful within the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

In particular, the selected dosage level depends upon a variety of factors, including the activity of the particular compound employed, the time of administration, the rate of excretion of the compound, the duration of the treatment, other drugs, compounds or materials used in combination with the compound, the age, sex, weight, condition, general health and prior medical history of the subject being treated, and like factors well, known in the medical arts.

A medical doctor, e.g., physician or veterinarian, having ordinary skill in the art may readily determine and prescribe the effective amount of the pharmaceutical composition required. For example, the physician or veterinarian may start doses of the compounds useful within the invention employed in the pharmaceutical composition at levels lower than that required in order to achieve the desired therapeutic effect and gradually increase the dosage until the desired effect is achieved.

In certain embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on the unique characteristics of the therapeutic compound and the particular therapeutic effect to be achieved, and the limitations inherent in the art of compounding/formulating such a therapeutic compound for the treatment of an HIV-1 infection in a subject.

In certain embodiments, the compositions of the invention are formulated using one or more pharmaceutically acceptable excipients or carriers. In certain embodiments, the pharmaceutical compositions of the invention comprise a therapeutically effective amount of a compound useful within the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the subject in dosages that range from one to five times per day or more. In other embodiments, the compositions of the invention are administered to the subject in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any subject are determined by the attending physical taking all other factors about the subject into account.

Compounds useful within the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In certain embodiments, the dose of a compound useful within the invention is from about 1 mg and about 2,500 mg. In other embodiments, a dose of a compound useful within the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in certain embodiments, a dose of a second compound (i.e., an HIV-1 antiviral) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments therebetween.

In certain embodiments, the present invention is directed to a packaged pharmaceutical composition comprising a container holding a therapeutically effective amount of a compound useful within the invention, alone or in combination with a second pharmaceutical agent; and instructions for using the compound to treat, prevent, or reduce one or more symptoms of an HIV-1 infection in a subject.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multilayer tablet comprising a layer providing for the delayed release of one or more compounds useful within the invention, and a further layer providing for the immediate release of a medication for HIV-1 infection. Using a wax/pH-sensitive polymer mix, a gastric insoluble composition may be obtained in which the active ingredient is entrapped, ensuring its delayed release.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents. For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration:

For oral administration, the compositions of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration:

For parenteral administration, the compositions of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms:

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 2003/0147952, 2003/0104062, 2003/0104053, 2003/0044466, 2003/0039688, and 2002/0051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing:

The therapeutically effective amount or dose of a compound of the present invention will depend on the age, sex and weight of the subject, the current medical condition of the subject and the nature of the infection by an HIV-1 being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days.

The compounds for use in the method of the invention may be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 and so forth, as well as individual numbers within that range, for example, 1, 2, 2.7, 3, 4, 5, 5.1, 5.3, 5.5, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

All chemical reagents, unless specified, were purchased from commercial sources or prepared according to published procedures. A CEM microwave synthesizer (Liberty Blue) was used for solid phase peptide synthesis. All Fmoc-, Boc-protected amino acids, N,N'-diisopropylcarbodiimide (DIC), ethyl (hydroxyimino) cyanoacetate (OxymaPure) and rink amide resin (100-200 mesh size, 0.53 meq/g substitution) were purchased from Chem-Impex International, INC. CuI catalyst for the click reaction, and hydrazine, were purchased from Sigma Aldrich. HPLC purifications were performed using a Waters® HPLC system with reverse phase $C_{18}$ semi-prep/prep columns. Purity checks of PTs were carried out by analytical $C_{18}$ RP-HPLC, using a BeckmanCoulter® HPLC system. HPLC grade ACN, Millipore-MilliQ water and 0.1% TFA were used as solvents for the HPLC purification. Mass validation was performed in-house (using Thermo Scientific LTQ XL Ion Trap LC/MS) and at the Wistar Proteomics Facility (using MALDI-TOF Mass Spectrometry). All data were collected on an ABI/PerSeptive (Framingham, Mass.) Voyager DE-PRO MALDI-TOF instrument in positive-ion mode; samples were spotted onto a 96 well plate coated using alpha-cyano-4-cinnamic acid matrix (Sigma) at 10 mg/mL. External calibration was performed on all samples.

General Methods for Gold Nanoparticle (AuNP) Synthesis and Characterization:

The citrate reduction method developed by Frens et al., 1973, Nature 241:2 is modified in order to synthesize size-controlled stable monodispersed AuNPs.

In one embodiment, 300 µl of 1% $HAuCl_4$ is added to 30 ml of 18 µm filtered water and heated to 150° C. in an Erlenmeyer flask for 1 hour. Subsequently 700 µl, 600 µl, 500 µl, 450 µl, or 400 µl of 1% citric acid are added into the flask in order to obtain 10 nm, 20 nm, 25 nm, 30 nm or 40 nm respectively. The solution is stirred vigorously for 15 min and gradually a color change is observed from light yellow to deep purple to wine red.

In another embodiment, for 20 nm AuNPs, 1% $HAuCl_4$ (300 µl) is added to 18 µm filtered water (total volume, 30 ml) and heated to 100° C. in an Erlenmeyer flask for 1 hour, followed by addition of 1% citric acid (600 µl).

The solution is then cooled to room temperature, and BSPP (15 mg) is added into the synthesized particles (in a non-limiting embodiment, for stabilization) and stirred overnight at room temperature. The produced particles are further washed with phosphate buffer at pH 7 and concentrated using the Millipore 100,000 kDa filter. The particle size is obtained using dynamic light scattering (DLS) in the Zetasizer NS90 (Malvern Instruments), and the particle concentration is calculated using the absorbance reading at 450 nm ($A_{450}$) and at the surface plasmon resonance absorbance Aspr. This method is adopted from Haiss et al., 2007, Anal Chem 79:4215-4221. The 20 nm AuNP particle morphology is characterized using transmission electron microscopy (TEM). Sample is prepared by adding a drop of the AuNP solution onto a carbon grid film and allowed to evaporate. TEM bright field images are taken on a JEM 2100 operated at 200 kV.

General AuNP Conjugation and Validation of Stability:

The peptide-nanoparticle conjugation is conducted by adding a predetermined stabilizing concentration of the cyclic peptide to the synthesized AuNP and incubating under vigorous stirring at room temperature for 30 minutes. The thiol group present in the carboxyl terminus is used for covalent linkage to the Au. The hemolytic bond energy of a thiol group to a gold surface is approximately 40 kcal·$mol^{-1}$, and the reaction that takes place is an oxidative addition of the thiol bond to the gold surface.

In one embodiment, the peptide of the invention in phosphate buffer is added dropwise into a stabilized AuNP solution, at a molar ratio of 1:1000 of peptide:AuNP. This ratio is predetermined by conducting a nanoparticle flocculation/aggregation assay. The reaction lasts for 30 minutes under vigorous stirring at room temperature in a parafilm sealed glass vial. The conjugated particles are spun down for 15 minutes at 14,000 rpm, and the pellet is resuspended in phosphate buffer. Conjugation efficiency is calculated by an absorbance difference method using the UV-spectrophotometer.

The conjugate is purified by several washes in phosphate buffer (pH 7.2) using ultracentrifugation and further filtration on a 0.2 µm filter. The conjugation efficiency is calculated using amino acid analysis of the conjugate.

A stability study is conducted comparing AuNP-citrate stabilized, AuNP-BSPP stabilized, as well as unstabilized AuNP-peptide conjugates. All particles were incubated for 1 hour in deionized water, PBS, NaCl (17 mM), and HOS.T4.R5 cell growth media. The tests are designed to test the aggregation of the various AuNP-peptide conjugates under physiologic conditions. As a control, phosphate buffer at pH 7.0 is used, and Aspr of the AuNP is measured using a UV-Vis spectrophotometer. The shift of the absorbance values suggests aggregation of the AuNP particles.

To further validate in-vitro stability, a cytotoxicity test was conducted. Modified human osteosarcoma cells (HOS.T4.R5) are seeded at 10,000 cells per well in a 96 well plate. After 24 hours, they are exposed to AuNPs, AuNP-peptide conjugates and Ted-Pella 20 nm particles (positive control), suspended in phosphate buffer at pH 7.0, at an initial concentration of 50 nM determined using UV V is spectrometer. Toxicity is tested 48 hours post-addition using the tetrazolium salt premix reagent, WST-1 from Takara Bio Inc., following the manufacturer's protocol. The formazan product is measured using a microplate reader at 460 nm (Molecular Devices).

Example 1: Cyclic Peptides

Figure 2A:
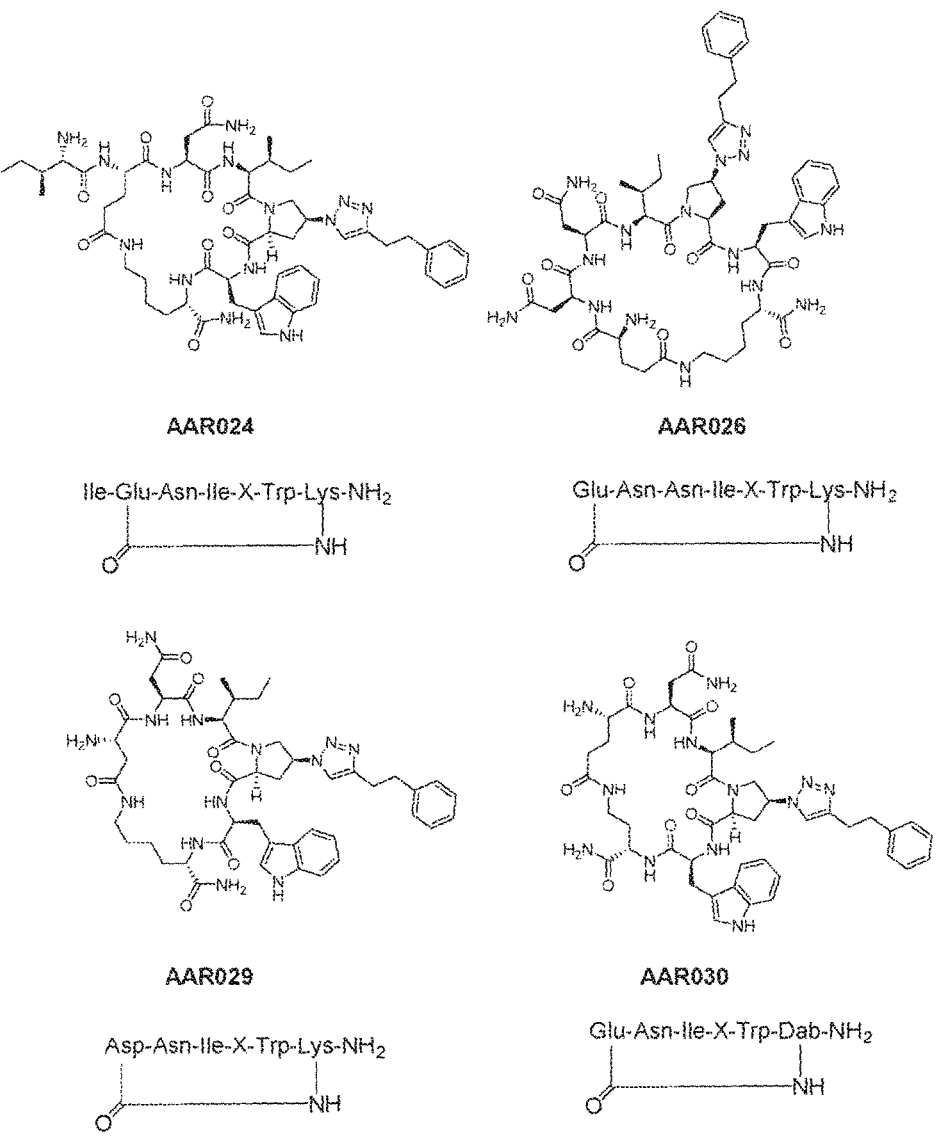
FIG. 2a comprises a schematic illustration of certain cyclic peptides of the invention (AAR024 or SEQ ID No:4; AAR026 or SEQ ID No:5; AAR029 or SEQ ID No:6; AAR030 or SEQ ID No:7). Each occurrence of X is independently a modified proline.

Cyclic peptides of the invention were prepared using intramolecular cyclization involving side chain groups of Lys and Glu residues (FIG. 2). Lys and Glu side chain groups (amino and carboxylic acid, respectively) were protected with protecting groups (Dde and Dmab, respectively) that can be removed under the same condition by mild reagents (2% hydrazine in dimethylformamide). These protecting groups were also orthogonal to other groups such as the Fmoc, Boc and Trt groups usually utilized in Fmoc-based peptide synthesis.

Figure 3:
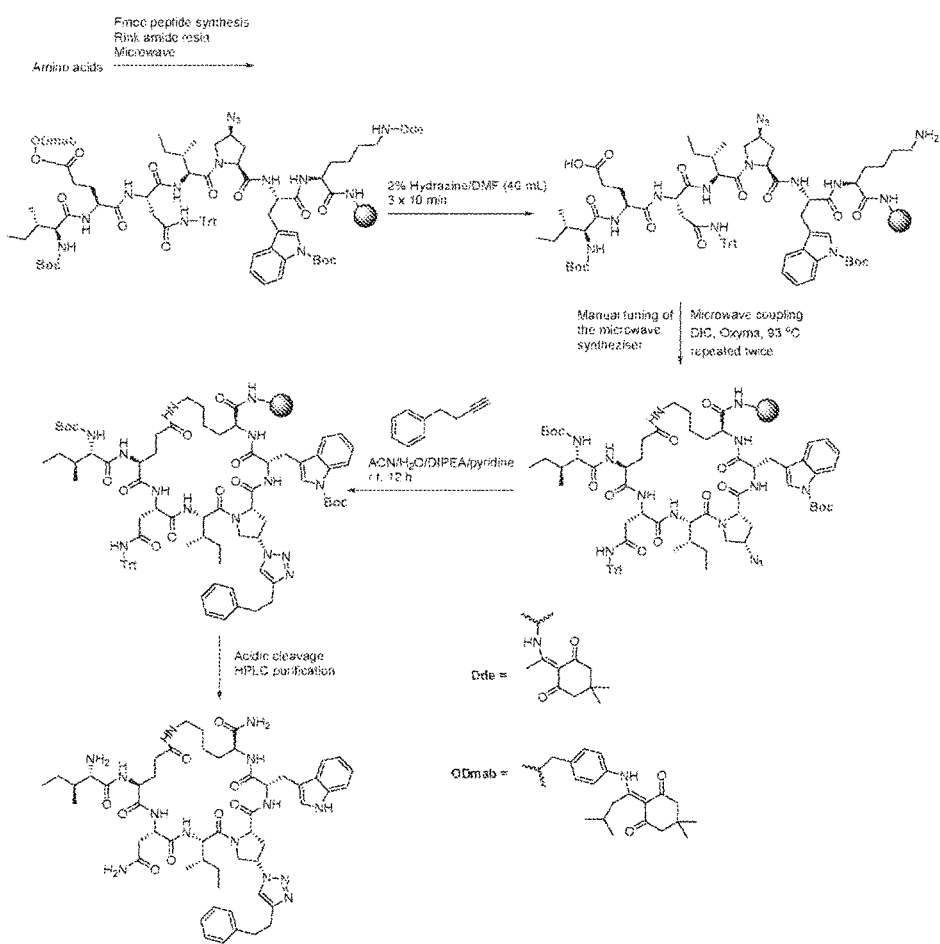
FIG. 3 comprises a schematic illustration of a non-limiting synthetic route to cyclic peptides of the invention.
Figure 5A:
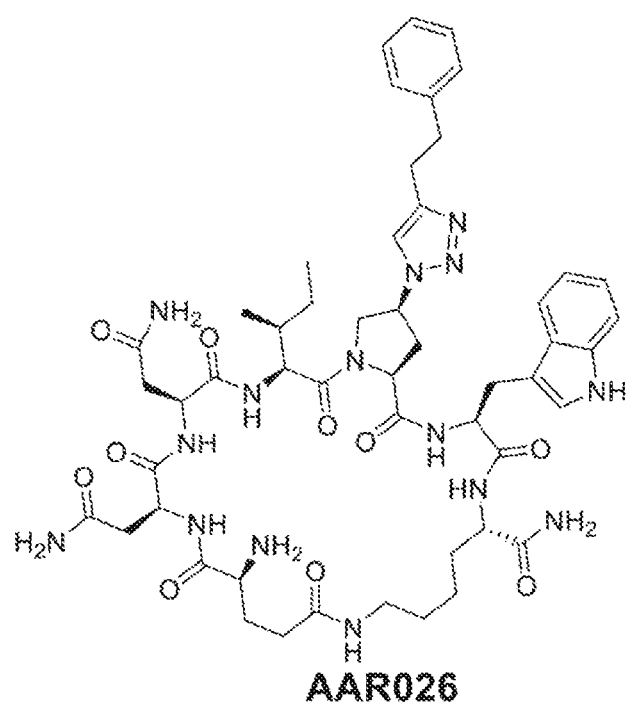
FIG. 5a illustrates a cyclic peptide of the invention.
Figure 6A:
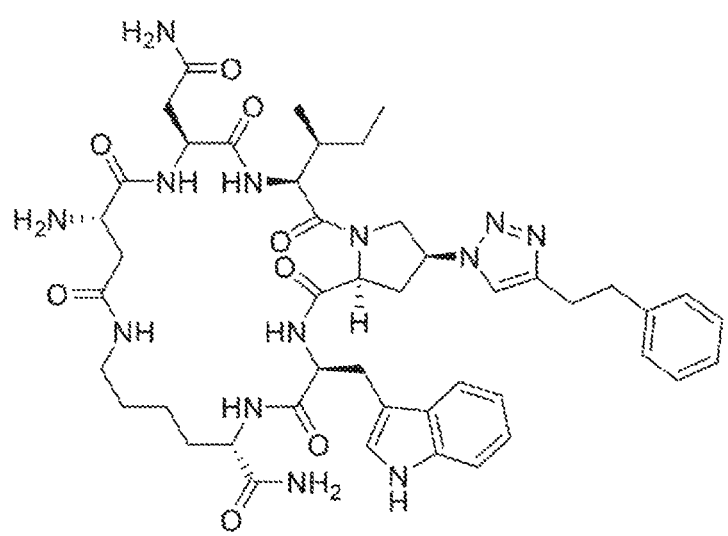
FIG. 6a illustrates a cyclic peptide of the invention.

FIG. 3 illustrates the synthesis of AAR024 in a non-limiting manner.

In certain embodiments, peptide sequence assembly was performed with a microwave peptide synthesizer on a 0.25 mM scale, utilizing N-Fmoc-protected amino acids (Lys, Trp, AzidoPro, Ile and Glu) and one N Boc-protected Ile residue, and using DIC/Oxyma (0.5 M solutions in DMF) for the coupling activation. A solution of 20% piperidine in DMF with 0.1M HOBt was used for deprotecting the Fmoc groups in the microwave Fmoc deprotection step. The side chains of Lys and Glu were protected by N-(1-(4,4-dimethyl-2,6-dioxocyclohexylidene)ethyl) and 4-[N-(1-(4,4-dimethyl-2,6-dioxocyclohexylidene)-3-methylbutyl)amino] benzyl ester, respectively. After peptide assembly, the side chains of Lys and Glu were selectively deprotected on-resin using a solution of 2% hydrazine in DMF (3×50 mL, 10 min each) and the resin was then washed with DMF (3×50 mL). The peptide-bound resin was then loaded in the reaction vessel of the microwave synthesizer and 4 mL of 0.5 M DIC in DMF and 2 mL 0.5 M Oxyma in DMF (for 0.25 mM synthesis scale) were added. A microwave coupling cycle was then performed twice using the standard coupling method of the synthesizer system. The peptide-bound resin was then removed and added to a peptide reaction vessel, a mixture of ACN/water/DIPEA/pyridine (4.25/4.25/1.06/0.53 v/v for 0.5 g of resin) was added, two equivalents of 4-phenyl-1-butyne for AAR024 or ethynylferrocene for AAR024b and a catalytic amount of CuI (2 mol %) were added. The vessel was placed on a shaker for 12 h at room temperature. The resin was then washed serially with 5% HCl (3×50 mL), DMF (3×25 mL) and DCM (4×25 mL). Cleavage and global deprotection were then carried out using a cleavage cocktail of TFA/ethanedithiol/$H_2O$/thioanisole (4.75/0.1/0.1/0.05 v/v for 0.5 g of resin) for 2 h at r.t. Cleaved peptide solutions were concentrated under a gentle $N_2$ stream, added to pre-cooled diethyl ether to precipitate the solid peptide pellets and centrifuged. Diethyl ether washing cycle was repeated until the ether layer was no longer colored. Crude peptide pellets were dried by a gentle $N_2$ stream, dissolved and purified (to >95% purity) using semi-prep/prep $C_{18}$ (or semi-prep $C_4$) RP-HPLC columns (ACN/$H_2O$/0.1% TFA) equipped with a Waters® HPLC pump 2545 module and 2489 UV/Visible detector, and finally lyophilized to yield solid peptides. Peptides were validated using Thermo Scientific LTQ XL Ion Trap LC/MS and matrix-assisted laser desorption ionization time-of-flight mass spectrometry (MALDI-TOF MS).

The synthesis for AAR026 was similar to that for AAR024, with a few modifications. After microwave cyclization, the N-terminal Fmoc group was removed by a microwave deprotection method followed by click reaction. Alternatively, the click reaction could also be performed while the N-Fmoc group was still intact, which then was removed by a microwave deprotection cycle.

Peptide AAR028 was synthesized similarly to AAR024 & AAR026 without assembling the N terminal Ile in the first synthesis step. The starting sequence for AAR028 was (Glu1-Asn2-Ile3-X4-Trp5-Lys6) where X is the azido-proline residue. Peptide AAR030 was synthesized starting from the linear sequence (Glu1-Asn2-Ile3-X4-Trp5-Dab6).

Peptides AAR031 and AAR032 were synthesized using the refined procedures described in FIG. 3. Fmoc-L-Ornithine(Dde)-OH and Fmoc-L-Dab(ivDde)-OH were used for AAR031 and AAR032, respectively. The ivDde (4,4-dimethyl-2,6-dioxocyclohex-1-ylidene)-3-methylbutyl) protecting group was deprotected using 2% hydrazine in DMF.

FIGS. 2a, 2b, 2c and 2d illustrate a library of cyclic peptides (AAR024, AAR024A, AAR024b, AAR026, AAR028, AAR029, AAR029b, AAR029b-Chg, AAR029E, AAR029, AAR029H, AAR029J, AAR030, AAR031, AAR032, AAR036, AAR039, AAR040, AAR042) synthesized using methods summarized in this example.

Example 2: Inhibition of HIV-1 gp120 Proteins 2.1. Reagents

*Escherichia coli* strain XL-10 gold and Stbl2 cells were products of Novagen Inc. (Madison, Wis.). Thermostable DNA polymerase (pfu Ultra™) was obtained from Stratagene Inc (La Jolla, Calif.). Custom-oligonucleotide primers were supplied by Integrated DNA technologies (IDT). DNA plasmids encoding BaL.01 gp160 and NL4-3 R-E-Luc+ were obtained from the NIH AIDS Reagent Program, Division of AIDS, NIAID. All other reagents used were of the highest analytical grade available.

2.2. Expression and Purification of Wild-Type gp120YU-2

The DNA for gp120YU-2 in pcDNA3.1 vector for transient transfection was purified using a Qiagen MaxiPrep kit (Qiagen) and transfected into HEK 293F cells according to manufacturer's protocol (Invitrogen). Five days after transfection was initiated, cells were harvested and spun down, and the supernatant was filtered through 0.2 µm filters. Purification was performed over a 17b antibody-coupled column prepared using an NHS-activated Sepharose, HiTrap HP column (GE Healthcare). Gp120 was eluted from the column using 0.1M Glycine buffer pH 2.4. The pH of the eluted protein was rapidly neutralized by addition of 1M Tris pH 8.0. Identity of the eluted fractions was confirmed by SDS-PAGE and Western blotting using antibody D7324 (Aalto Bioreagents). Eluted protein was immediately buffer exchanged into PBS using spin-columns (Amicon Ultra Ultracell-30K, Millipore). Protein was filtered through 0.45 µm syringe filters (Millex-LH, Millipore) and separated by size exclusion on a HiLoad 26/60 Superdex 200 HR prepacked gel filtration column (GE). Purity of eluted fractions and monomeric state of gp120 were identified by SDS-PAGE/Western blotting with mAb D7324. Monomeric fractions were pooled, concentrated, frozen and stored at −80° C.

2.3. Four Domain Soluble CD4 Production

Hexa histidine-tagged 4-domain soluble CD4 (CD4) was produced by transient transfection into 293F cells using standard protocols (Gibco). The pcDNA3.1 vector carrying CD4 was a gift from Dr. Navid Madani. CD4 was separated from the expression medium by Nickel affinity purification on HiTrap columns (GE) using an Akta FPLC System (GE). CD4 was further purified by size-exclusion on a Superdex 200 column (GE). Protein size and functionality were verified by SDS-PAGE and anti-gp120 ELISA, respectively. 17b IgG was purchased from Strategic Diagnostics Inc (Newark, Del.).

2.4. Surface Plasmon Resonance (SPR) Assays

SPR experiments were performed on a Biacore 3000 optical biosensor (GE Healthcare). All experiments were carried out at 25° C. using standard PBS buffer pH=7.4 with 0.005% surfactant Tween. A CM5 sensor chip was derivatized by standard 1-ethyl-3-(3-dimethylaminopropyl) carbodiimide (EDC)/N-hydroxysuccinimide (NHS) chemistry, and coupling was done through ligand amine groups. Antibody 2B6R (α-human IL5R) was immobilized for negative control surfaces. For competition experiments, soluble four domain CD4 and 17b antibody were immobilized on the surface through standard EDC/NHS chemistry. For kinetic analyses, typically 2000-3000 RUs of protein reagents were immobilized on SPR chips, and analytes were passed over the surface at 50-100 µL/min. Surface regeneration was achieved by a 5 µL injection of 10 mM HCl solution at 100 µL/min. Analysis of peptide-mediated inhibition of gp120 binding to sCD4 and mAb 17b was achieved by injecting a fixed concentration of HIV-1YU-2 gp120 (250 nM), with increasing peptide concentrations, over sCD4 (2000 RU) and mAb 17b (1000 RU) surfaces for 5 minute association and 5 minute dissociation at a flow rate of 50 µl min-1 in PBS. Regeneration of the surface was achieved by a single 10 second pulse of 1.3 M NaCl/35 mM NaOH and single 5-second pulse of 10 mM glycine, pH 1.5, for sCD4 and mAb 17b, respectively. All analyses were performed in triplicate.

The evaluation method for SPR inhibition data included a calculation of the inhibitor concentration at 50% of the maximal response ($IC_{50}$). The inhibition curve was converted into a calibration curve by the use of a fitting function. The fitting was done using the 4-parameter Equation (1) from BIAevaluation software, $$\text{Response} = R_{high} - \frac{(R_{high} - R_{low})}{1 + \left(\frac{\text{Conc}}{A_1}\right)^{A_2}} \quad (1)$$

where $R_{high}$ is the response value at high inhibitor concentrations and $R_{low}$ is response at low inhibitor concentrations. Conc. is the concentration of inhibitor, and $A_1$ and $A_2$ are fitting parameters. At the $IC_{50}$ the following is true:

$$\text{Response} = R_{high} - \frac{(R_{high} - R_{low})}{2} \quad (2)$$

Under this condition, $A_1$=Conc and is therefore taken as the desired $IC_{50}$ parameter.

The cyclic peptides of the invention were tested against HIV-1 gp120 by SPR competition assays as described elsewhere herein. A mixture of the cyclic peptide/gp120 solutions was passed over SPR chip immobilized with CD4 and 17b separately. The competition assay evaluated the ability of each peptide to inhibit the binding between gp120 and both soluble CD4 and 17b antibody, a surrogate for co-receptor. AAR024, AAR024b, AAR026, AAR029, AAR029b, AAR029E, AAR029F, AAR031, AAR032, AAR036, AAR039, AAR040 and AAR042 were found to be dual inhibitors of both CD4 and 17b binding to gp120.

Example 3: Gp120 Shedding Analysis with AAR029b

Figure 7:
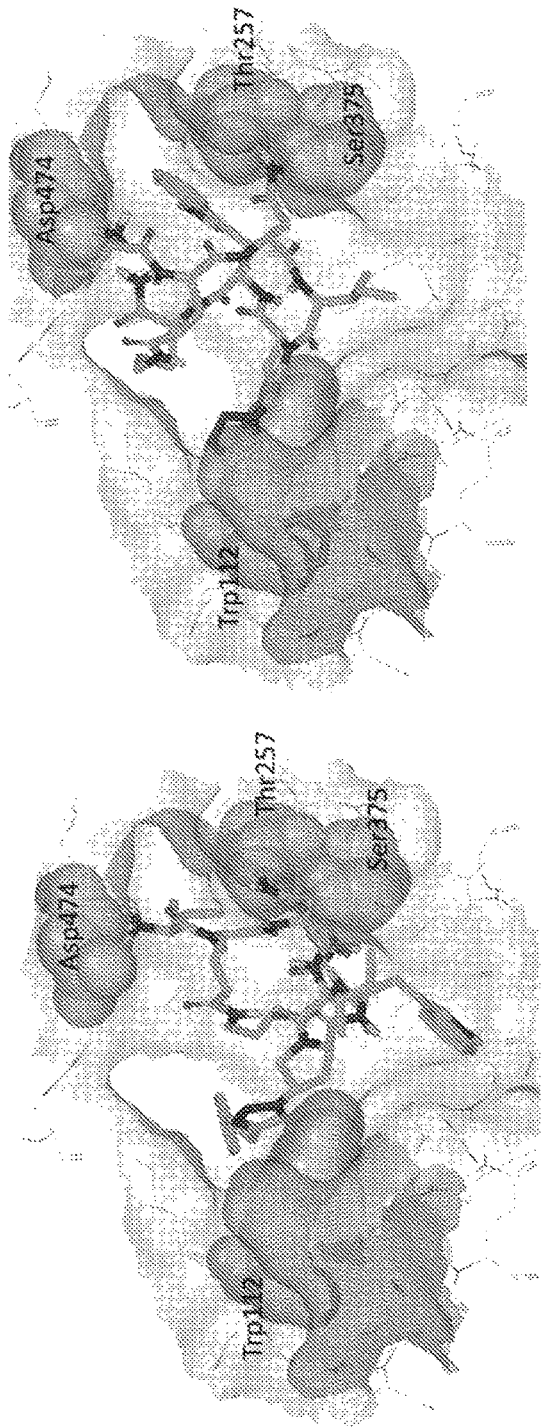
FIG. 7 comprises an illustration of a computer-generated model for binding of AAR024 to gp120.
Figure 8:
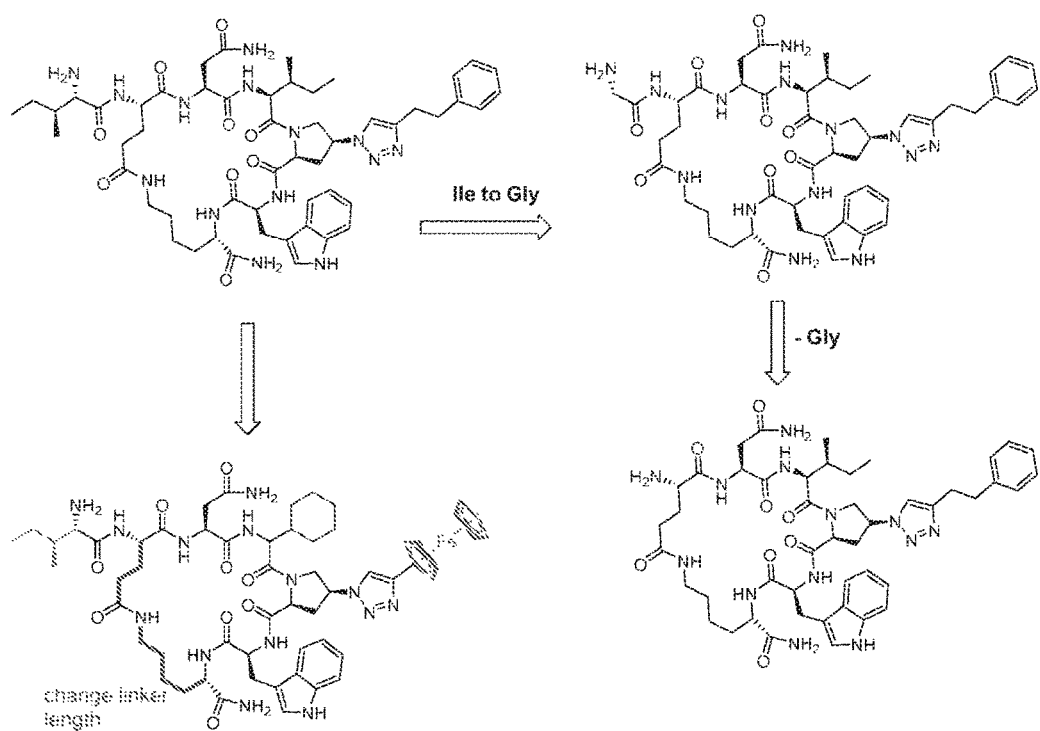
FIG. 8 illustrates cyclic peptides of the invention.
Figure 9:
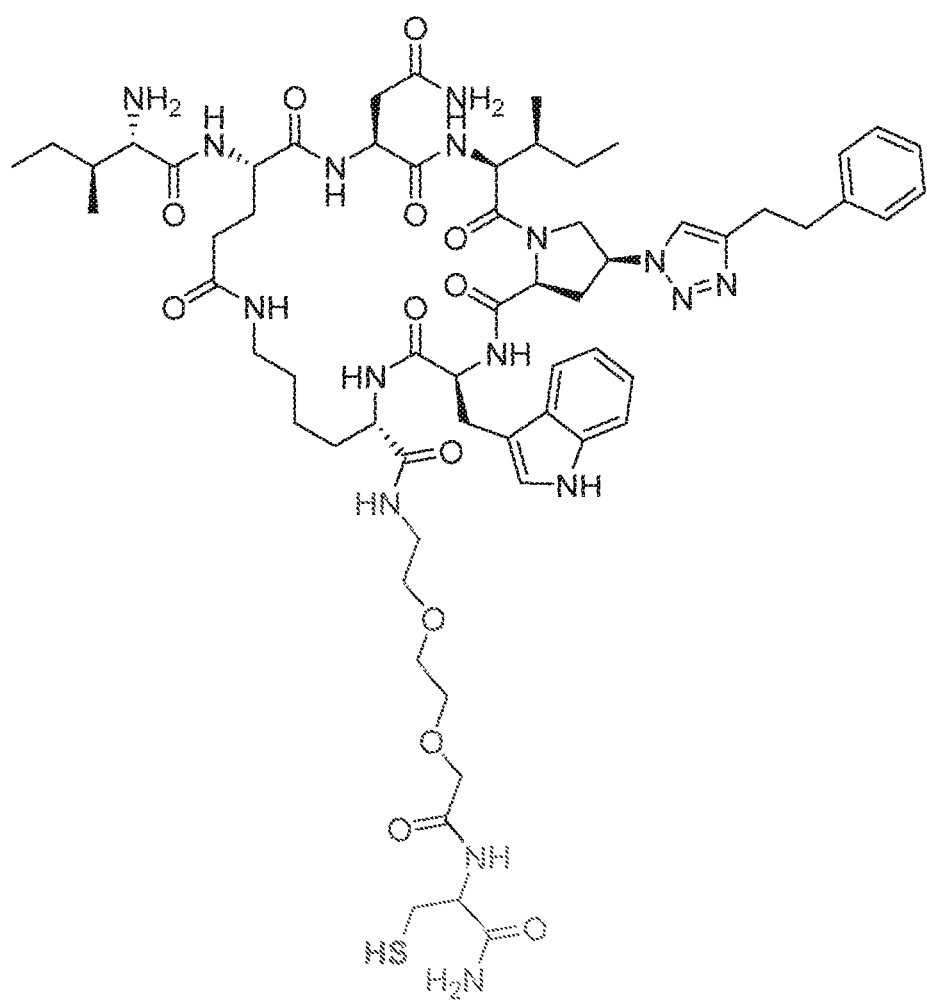
FIG. 9 illustrates a cyclic peptide of the invention comprising a free thiol group.

AAR029b was serially diluted in 1.5 ml tubes and mixed with JR-FL pseudotyped virus (1:1, v/v). Samples were mixed thoroughly with inversions before being incubated for 30 minutes at 37° C. Two controls were introduced where the pseudovirus was mixed with PBS. One sample was spun like the rest while the other was not (left at 4° C. during the spin) to establish the window (0%→100% respectively) for this assay. This was followed by a 2-hour spin at 4° C. in a table top centrifuge (Eppendorf) at 21,130×g. After the spin, supernatants were carefully separated from the pellet and mixed with Laemmli buffer (1:1, v/v) and boiled at 85° C. for 5 minutes. Samples were run on a 10% SDS-PAGE gel and then transferred to a 0.45 um PVDF membrane (Immobilon-P, EMD-Millipore), blocked with 5% milk solubilized in PBS containing 0.1% Tween-20 and then stained with sheep anti-gp120 (D7324, Aalto) followed by donkey anti-sheep HRP (Invitrogen) antibodies. Luminol substrate (Advansta) was added and the protein bands exposed on chemiluminescence film (Blue Ultra, Genemate) and developed (M35-A X-OMAT Processor, Kodak). The developed film was then scanned and the corresponding image analyzed with Image J (NIH) densitometry. The measured densities were normalized based on the controls to provide values from 0-100% and, the data were fit using Origin 9.0 sigmoidal fitting (Logistic) to determine the shedding $EC_{50}$ values (FIG. 11).

Example 4: Inhibition of HIV-1 Infection Against Bal.01 and JR-FL

HEK 293T cells ($3\times10^6$) were co-transfected with 4 μg of BaL.01 gp160 plasmid and 8 μg of NL4-3 R-E-Luc+ core DNA using Polyethyleneimine (PEI) as a transfection vehicle. JR-FL pseudoviruses were produced similarly using JR-FL gp160 DNA with the same core DNA and Fugene 6 (Roche) as a transfection vehicle. After 72 hours, the supernatant containing virus was collected and filtered using a 0.45 μm syringe filter (Corning) before being purified via gradient centrifugation using a 6%-20% Iodixanol gradient (Optiprep, Sigma Aldrich) spun on an Sw41 Ti rotor (Beckman Coulter) at 110,000×g for 2 hours at 4° C. The bottom 5 mls were collected and diluted in serum free medium before being aliquoted and frozen at −80° C. All batches of virus were titrated for infectivity and p24 content immediately after production.

HOS.T4.R5 cells were seeded the day before at 7000 cells/well, 100 μl/well in 96 well plates. Virus stocks were diluted in growth media such that the final dilution gave $1\times10^6$ luminescence counts. Peptides to be tested were solubilized in 1×PBS and serially diluted in 1.5 ml tubes. Virus was added to these peptide containing tubes 1:1 (v/v), and the tubes were mixed by repeated inversions. The positive control (100%) contained virus treated with PBS while the negative control (0%) contained no virus. The samples were incubated at 37° C. for 30 minutes before addition to the cells. Medium was removed from the plates and virus-containing medium was added. The plates were incubated for 24 hours at 37° C. before the medium was changed. 48 hours after the virus was added to the plate, the medium was removed and the cells were lysed (Passive Lysis Buffer, Promega). Lysed cells were then mixed with Luciferin salt (Anaspec) in 0.1 M potassium phosphate buffer containing 0.1 M magnesium sulfate and the luminescence measured using a Wallac 1450 Microbeta Luminescence reader. Infectivity values obtained were normalized to the controls before being fit using the Logistic sigmoidal fit (Origin 9.0) to determine the antiviral $IC_{50}$ potencies. Compounds AAR024b, AAR029, AAR029b, AAR029b-Chg and AAR029E were all found to have inhibiting activity against Bal.01 and AAR024b, AAR029 and AAR029b were found to have inhibiting activity against JR-FL.

Example 5: Comparison of Cyclic and Acyclic Peptides

Cyclic peptides of the invention, and the corresponding acyclic peptides, were evaluated (FIGS. 4*a*-4*c*, 5*a*-5*b*, and 6*a*-6*b*).

AAR024 peptide inhibited CD4 and 17b binding to gp120 with $IC_{50}$ values of 138 nM and 269 nM, respectively. The acyclic analogue of this peptide, denoted AAR024A, was found to be >50 fold less active than AAR024 (FIGS. 4*a*-4*c*).

AAR026 peptide was found to inhibit CD4 and 17b binding to gp120 with $IC_{50}$ values of 540 nM and 384 nM, respectively (FIGS. 5*a*-5*b*)

AAR029 peptide was found to inhibit CD4 and 17b binding to gp120 with $IC_{50}$ values of 85 nM and 96 nM, respectively (FIGS. 6*a*-6*b*).

Example 6: Binding Model of AAR024 with HIV-1 gp120

The binding of AAR024 with the gp120 protein was modeled computationally. Two low energy binding modes were predicted (FIG. 7), wherein both of them may be used to explain the dual inhibitory functions against gp120. The two models show that AAR024 occupies the CD4 site (as inferred by sCD4 competition) and, as inferred by 17b competition, sterically hinders the formation of the bridging sheet, an action required for co-receptor binding. These possible binding modes of the cyclic peptide may be tested using SPR competition experiments with gp120 mutants such as S375W, S375H and T257R. AAR024 was found inactive against S375W and S375H mutants of gp120, and therefore behaving like acyclic (linear) peptide triazoles in binding to gp120.

Example 7: In Vitro Proteolytic Stability Studies

Trypsin (from bovine pancreas, TPCK-treated, essentially salt-free, lyophilized powder, ≥10,000 BAEE units/mg protein) was purchased from Sigma-Aldrich. Chymotrypsin (bovine pancreas, ≥50 units BTEE/mg) was purchased from Chem-Impex International, Inc. A reverse-phase $C_{18}$ analytical column (Phenomenex) was used for the analysis of digestion mixtures using $ACN/H_2O/0.1\%$ TFA solvent system and absorption at 280 nm. ESI-MS analysis of chromatographic peaks obtained from the digestion mixtures was performed on Thermo Scientific LTQ XL Ion Trap LC/MS.

Cyclic peptide AAR029 and its linear analogue AAR029A were used for comparing the proteolytic stability. Each peptide was dissolved in 0.1 M $NH_4HCO_3$ aqueous buffer (pH 8.2) to a final concentration of 1 mg/mL. Fresh solutions of trypsin and chymotrypsin were prepared, by dissolving 1 mg of the enzyme in 50 mL of 0.1 M $NH_4HCO_3$ (pH 8.2). For each peptide, 150 μl peptide solution were mixed with 150 μl of enzyme solution in 1200 μl (final volume) of 0.1 M $NH_4HCO_3$ (pH 8.2), and the mixture was placed in a glass 5 mL vial and stirred at 37° C. (water bath). For RP-HPLC analysis, 150 μl aliquots of the incubated peptide/enzyme mixture were taken at given time intervals and mixed with 150 μl of 40% acetonitrile in $H_2O$ containing 2% TFA. Peptide samples without the proteolytic enzymes were used as controls at 0 h and at the end of the experiment. ESI-MS analyses were performed on the digestion mixture at each time point as well as the isolated HPLC peaks. After short time periods, AAR029A was broken down in the presence of trypsin and chymotrypsin while AAR029 remained stable beyond 40 hours.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A cyclic compound of formula (I), or a salt, solvate, enantiomer, or diastereoisomer thereof:

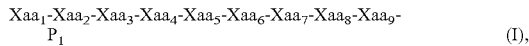

(I), wherein in (I):
   $Xaa_1$ is selected from the group consisting of absent, Glu, and Arg;
   $Xaa_2$ is selected from the group consisting of absent, Phe, Asp, Glu, and Ile;
   $Xaa_3$ is selected from the group consisting of absent, Asn, Asp, and Glu;
   $Xaa_4$ is selected from the group consisting of Asn and Asp;
   $Xaa_5$ is a modified glycine of formula (III)

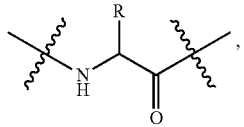

wherein in (III) R is selected from the group consisting of $C_1$-$C_6$ alkyl and $C_3$-$C_6$ cycloalkyl;
   $Xaa_6$ is the modified proline of formula (IV)

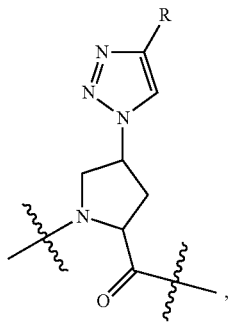

wherein in (IV) R is selected from the group consisting of naphthyl, p-methyl phenyl, p-ethyl phenyl, 2-phenylethyl, 1-adamantyl, 2-adamantyl, and metallocene;
   $Xaa_7$ is selected from the group consisting of Trp and 3-(3-benzothienyl)-L-alanine;
   $Xaa_8$ is selected from the group consisting of 2,4-diaminobutanoic acid, Orn, and Lys;
   $Xaa_9$ is selected from the group consisting of absent, 2,4-diaminobutanoic acid, Orn, Lys, Glu, and 2-(2-(2-aminoethoxy)ethoxy)acetic acid;
   $P_1$ is absent, or is a group that comprises at least one thiol group and is covalently linked through an amide bond to (i) the C-terminus of $Xaa_9$ if $Xaa_9$ is not absent, or (ii) the C-terminus of $Xaa_8$ if $Xaa_9$ is absent;
   the side chain amino group of one residue selected from the group consisting of 2,4-diaminobutanoic acid at $Xaa_8$, Orn at $Xaa_8$, Lys at $Xaa_8$, 2,4-diaminobutanoic acid at $Xaa_9$, Orn at $Xaa_9$, and Lys at $Xaa_9$ forms an amide bond with the side chain carboxylic acid group of one residue selected from the group consisting of Glu at $Xaa_2$, Asp at $Xaa_2$, Glu at $Xaa_3$, Asp at $Xaa_3$ and Asp at $Xaa_4$; and
   the C-terminus of $Xaa_8$ is optionally amidated if $Xaa_9$ and $P_1$ are absent, or the C-terminus of $Xaa_9$ is optionally amidated if $P_1$ is absent.

2. The cyclic compound of claim 1, which is selected from the group consisting of:

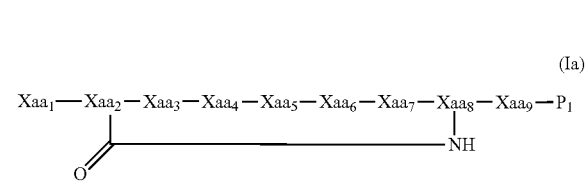

(Ia)

-continued (Ib)
Xaa$_1$—Xaa$_2$—Xaa$_3$—Xaa$_4$—Xaa$_5$—Xaa$_6$—Xaa$_7$—Xaa$_8$—Xaa$_9$—P$_1$ (Ic)
Xaa$_1$—Xaa$_2$—Xaa$_3$—Xaa$_4$—Xaa$_5$—Xaa$_6$—Xaa$_7$—Xaa$_8$—Xaa$_9$—P$_1$ (Id)
Xaa$_1$—Xaa$_2$—Xaa$_3$—Xaa$_4$—Xaa$_5$—Xaa$_6$—Xaa$_7$—Xaa$_8$—Xaa$_9$—P$_1$ (Ie)
Xaa$_1$—Xaa$_2$—Xaa$_3$—Xaa$_4$—Xaa$_5$—Xaa$_6$—Xaa$_7$—Xaa$_8$—Xaa$_9$—P$_1$ (If)
Xaa$_1$—Xaa$_2$—Xaa$_3$—Xaa$_4$—Xaa$_5$—Xaa$_6$—Xaa$_7$—Xaa$_8$—Xaa$_9$—P$_1$

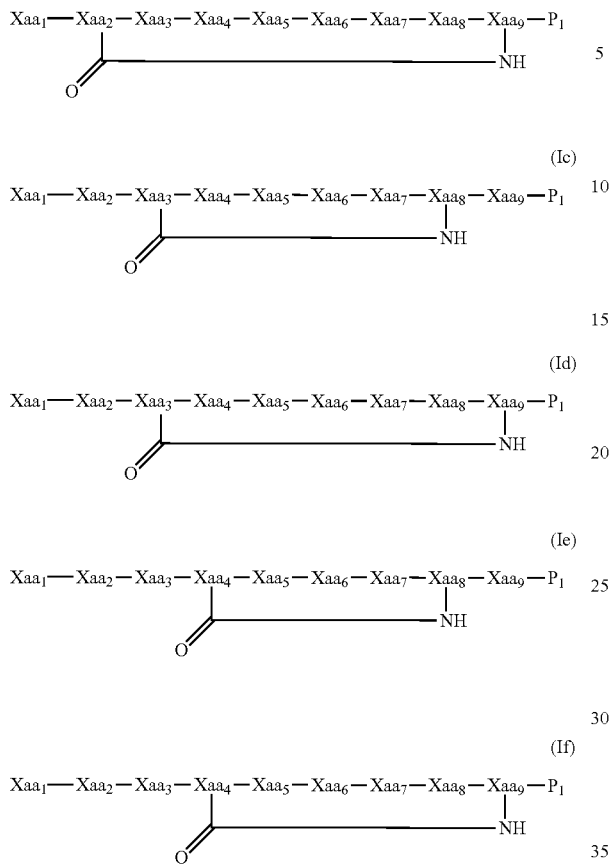

wherein in (Ia)-(If)

'NH' is derived from the side chain amino group of a residue selected from the group consisting of 2,4-diaminobutanoic acid at Xaa$_8$, Orn at Xaa$_8$, and Lys at Xaa$_8$, 2,4-diaminobutanoic acid at Xaa$_9$, Orn at Xaa$_9$, and Lys at Xaa$_9$, and 'C=O' is derived from the side chain carboxylic acid group of a residue selected from the group consisting of Glu at Xaa$_2$, Asp at Xaa$_2$, Glu at Xaa$_3$, Asp at Xaa$_3$, and Asp at Xaa$_4$.

3. The cyclic compound of claim 1, which is the cyclic compound of formula (II):

Xaa$_1$-Xaa$_2$-Xaa$_3$-Xaa$_4$-Xaa$_5$-Xaa$_6$-Xaa$_7$-Xaa$_8$-Xaa$_9$-P$_1$     (II), wherein in (II):

Xaa$_1$ is selected from the group consisting of absent, Glu, and Arg;

Xaa$_2$ is selected from the group consisting of absent, Phe, Asp, Glu, and Ile;

Xaa$_3$ is selected from the group consisting of Asn, Asp, and Glu;

Xaa$_4$ is Asn;

Xaa$_5$ is Ile;

Xaa$_6$ is the modified proline of formula (IV)

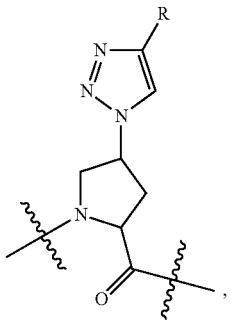

wherein in (IV) R is selected from the group consisting of naphthyl, p-methyl phenyl, p-ethyl phenyl, 2-phenylethyl, and metallocene;

Xaa$_7$ is Trp;

Xaa$_8$ is selected from the group consisting of 2,4-diaminobutanoic acid, Orn, and Lys;

Xaa$_9$ is selected from the group consisting of absent, 2,4-diaminobutanoic acid, Orn, Lys, Glu, and 2-(2-(2-aminoethoxy)ethoxy)acetic acid;

P$_1$ is absent, or is a group that comprises at least one thiol group and is covalently linked through an amide bond to (i) the C-terminus of Xaa$_9$ if Xaa$_9$ is not absent or (ii) the C-terminus of Xaa$_8$ if Xaa$_9$ is absent;

the side chain amino group of one residue selected from the group consisting of 2,4-diaminobutanoic acid at Xaa$_8$, Orn at Xaa$_8$, Lys at Xaa$_8$, 2,4-diaminobutanoic acid at Xaa$_9$, Orn at Xaa$_9$, and Lys at Xaa$_9$ forms an amide bond with the side chain carboxylic acid group of one residue selected from the group consisting of Glu at Xaa$_2$, Asp at Xaa$_2$, Glu at Xaa$_3$, and Asp at Xaa$_3$; and the C-terminus of Xaa$_8$ is optionally amidated if Xaa$_9$ and P$_1$ are absent, or the C-terminus of Xaa$_9$ is optionally amidated if P$_1$ is absent.

4. The cyclic compound of claim 1, wherein Xaa$_5$ is selected from the group consisting of Ile, Leu, norleucine (Nle), cyclopropylglycine, cyclobutylglycine, cyclopentylglycine, and cyclohexylglycine.

5. The cyclic compound of claim 1, wherein P$_1$ is not absent.

6. The cyclic compound of claim 5, wherein P$_1$ is selected from the group consisting of:

βAla Gln βAla Cys-NH$_2$, βAla Gln βAla Cys,

NH$_2$(CH$_2$CH$_2$O)$_{0-10}$CH$_2$C(=O)NHCH(CH$_2$SH)C(=O)OH,

NH$_2$(CH$_2$CH$_2$O)$_{0-10}$CH$_2$C(=O)NHCH(CH$_2$SH)C(=O)NH$_2$,

NH$_2$(CH$_2$)$_{0-12}$CH$_2$C(=O)NHCH(CH$_2$SH)C(=O)OH,

NH$_2$(CH$_2$)$_{0-12}$CH$_2$C(=O)NHCH(CH$_2$SH)C(=O)NH$_2$, and

NH$_2$CH$_2$CH$_2$OCH$_2$CH$_2$OC(=O)NHCH(CH$_2$SH)C(=O)NH$_2$.

7. A cyclic compound, or a salt, solvate, enantiomer or diastereoisomer thereof, which is selected from the group consisting of:

AAR024
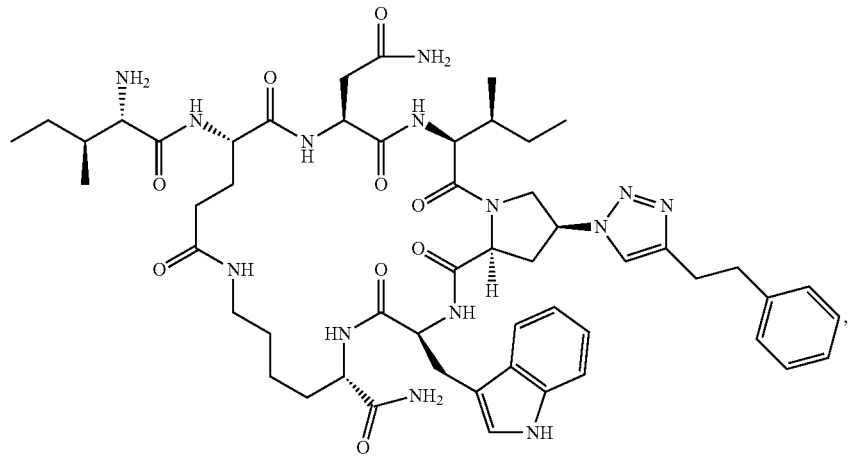
AAR026
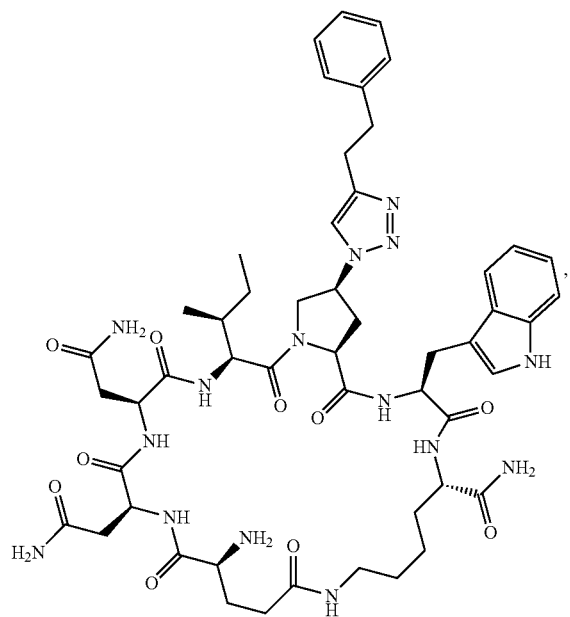
AAR029
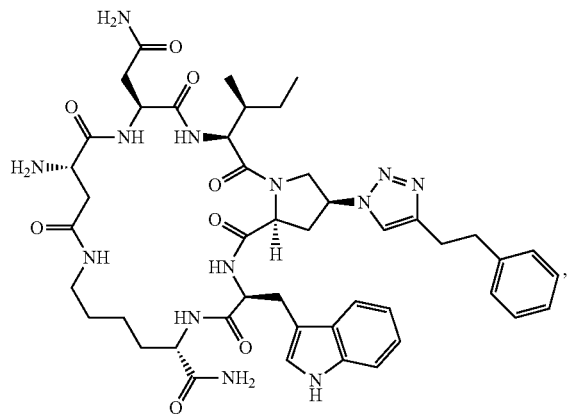
AAR030
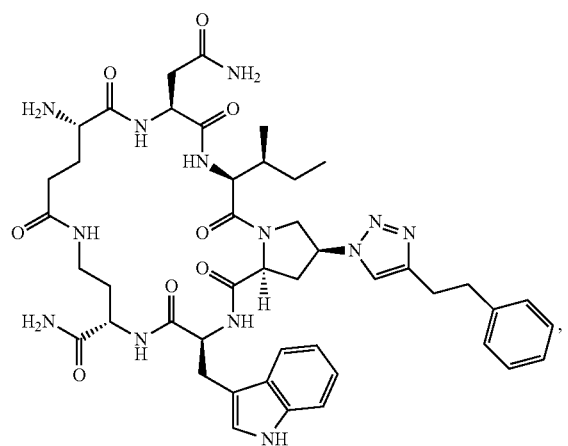
AAR031
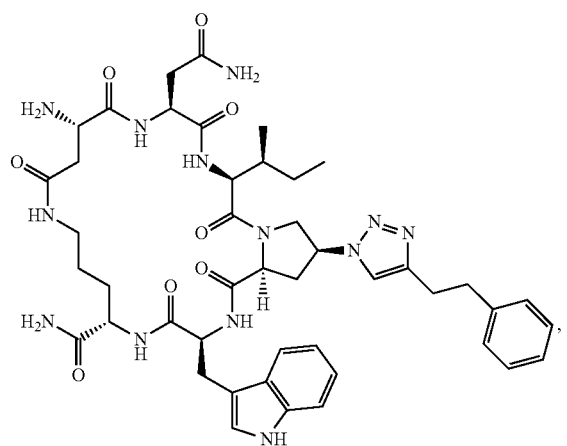

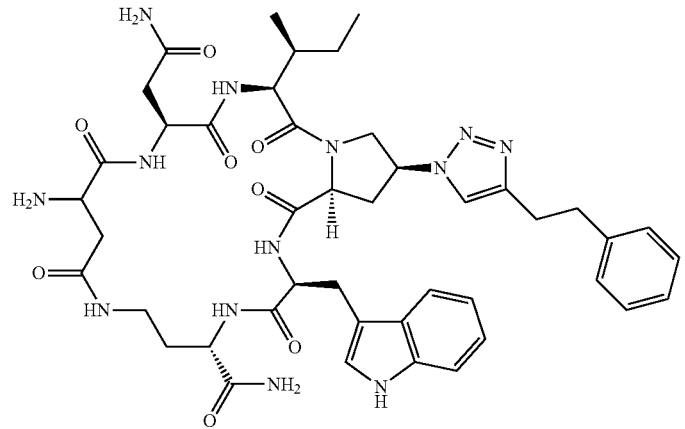
AAR032
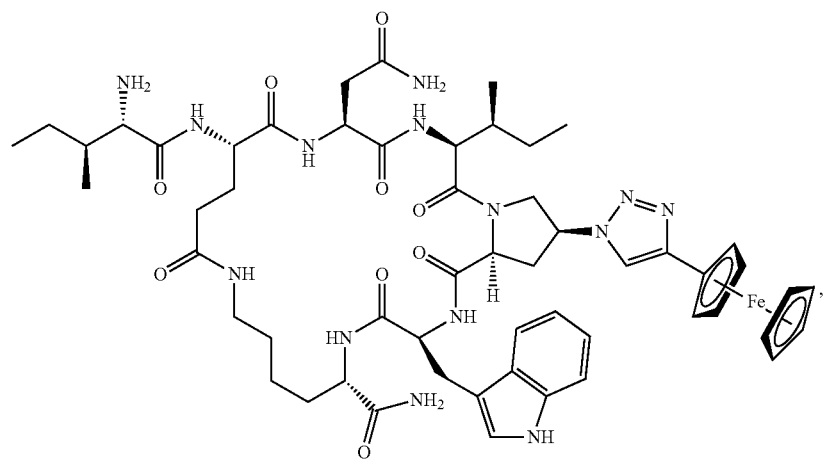
AAR024B
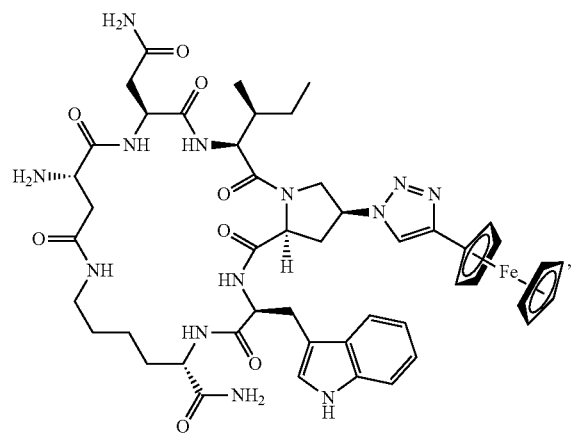
AAR029B
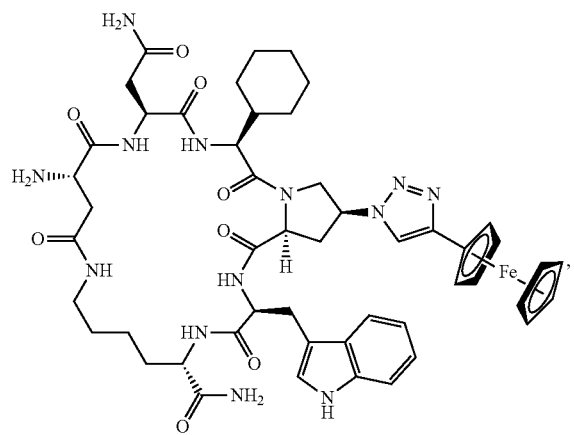
AAR029b-Chg

-continued

AAR029E
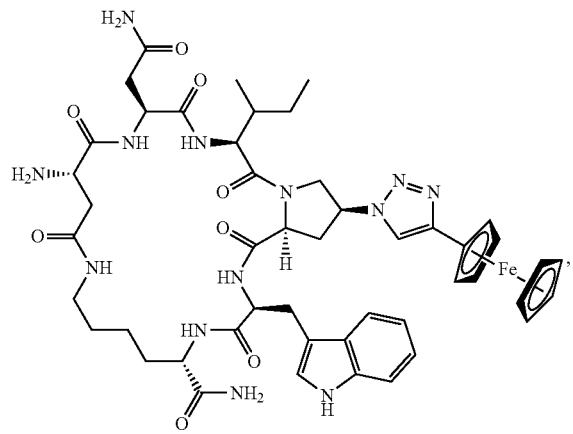

AAR036
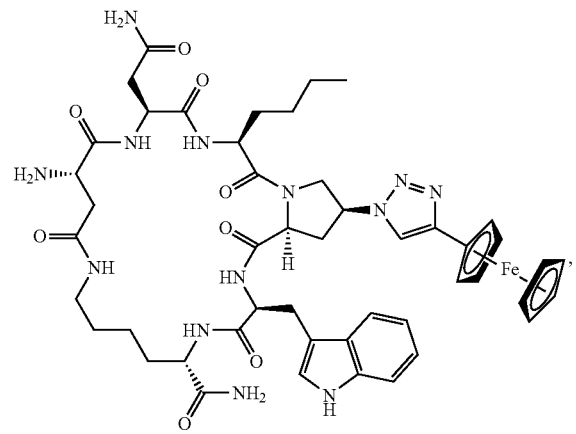

AAR029F
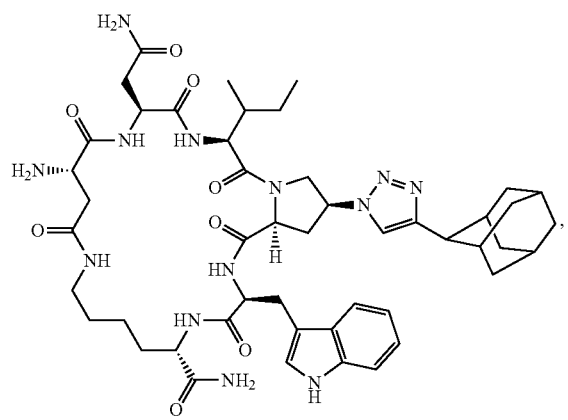

AAR029H
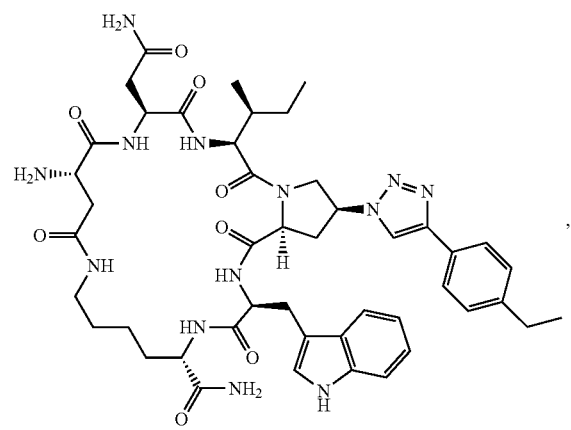

AAR040
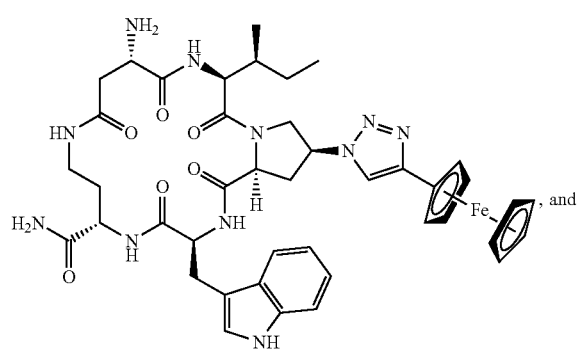

AAR042
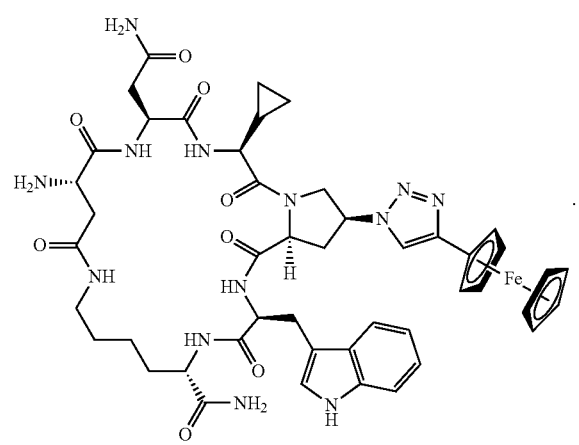

8. The cyclic compound of claim 1, wherein $P_1$ is not absent and wherein (I) is complexed through the at least one thiol group with at least one gold nanoparticle.

9. A pharmaceutical composition comprising at least one pharmaceutically acceptable carrier and at least one cyclic compound of claim 1.

10. A method of reducing the risk of HIV-1 infection in a mammal at risk of HIV-1 exposure, the method comprising administering to the mammal a therapeutically effective amount of at least one cyclic compound of claim 1.

11. The method of claim 10, wherein the compound is selected from the group consisting of AAR024, AAR026, AAR029, AAR030, AAR031, AAR032, AAR024B, AAR029B, AAR029b-Chg, AAR029E, AAR036, AAR029F, AAR029H, AAR040 and AAR042.

12. The method of claim 10, wherein $P_1$ is not absent, wherein optionally (I) is complexed through the at least one thiol group with at least one gold nanoparticle.

* * * * *

SEQUENCE LISTING

```
<160> NUMBER OF SEQ ID NOS: 22

<210> SEQ ID NO 1
<211> LENGTH: 12
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (6)..(6)
<223> OTHER INFORMATION: (4S)-4-(4-ferrocenyl-1H-1,2,3-triazol-1-yl)
      pyrrolidine-2-carboxylic acid
<220> FEATURE:
<221> NAME/KEY: MOD_RES
<222> LOCATION: (12)..(12)
<223> OTHER INFORMATION: AMIDATION

<400> SEQUENCE: 1

Arg Ile Asn Asn Ile Xaa Trp Ser Glu Ala Met Met
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Chemically Synthesized, Cyclic peptide wherein
      side chain amino group of a residue selected from Xaa8 or Xaa9
      forms amide bond with side chain carboxylic acid group of a
      residue selected from Xaa2, Xaa3 or Xaa4
<220> FEATURE:
<221> NAME/KEY: MOD_RES
<222> LOCATION: (1)..(1)
<223> OTHER INFORMATION: is selected from the group consisting of
      absent, Glu and Arg
<220> FEATURE:
<221> NAME/KEY: MOD_RES
<222> LOCATION: (2)..(2)
<223> OTHER INFORMATION: is selected from the group consisting of
```

```
      absent, Gly, Phe, Lys, Asp, Glu, Ile, Arg and Cit
<220> FEATURE:
<221> NAME/KEY: MOD_RES
<222> LOCATION: (3)..(3)
<223> OTHER INFORMATION: is selected from the group consisting of
      absent, Asn, Asp, Ile,Glu and 2-cyclohexylglycine
<220> FEATURE:
<221> NAME/KEY: MOD_RES
<222> LOCATION: (4)..(4)
<223> OTHER INFORMATION: is selected from the group consisting of Asn
      and Asp
<220> FEATURE:
<221> NAME/KEY: MOD_RES
<222> LOCATION: (5)..(5)
<223> OTHER INFORMATION: is a modified glycine of formula (III)
<220> FEATURE:
<221> NAME/KEY: MOD_RES
<222> LOCATION: (6)..(6)
<223> OTHER INFORMATION: is the modified proline of formula (IV)
<220> FEATURE:
<221> NAME/KEY: MOD_RES
<222> LOCATION: (7)..(7)
<223> OTHER INFORMATION: is selected from the group consisting of Trp
      and 3-(3-benzothienyl)-L-alanine
<220> FEATURE:
<221> NAME/KEY: MOD_RES
<222> LOCATION: (8)..(8)
<223> OTHER INFORMATION: is selected from the group consisting of Ser,
      Thr, 2,4-diaminobutanoic acid, Orn and Lys
<220> FEATURE:
<221> NAME/KEY: MOD_RES
<222> LOCATION: (9)..(9)
<223> OTHER INFORMATION: is selected from the group consisting of
      absent, 2,4-diaminobutanoic acid, Orn, Lys, Glu, Glu-Ala, Glu-Ala-
      Met, Glu-Ala-Met-Met, and 2-(2-(2-aminoethoxy)ethoxy)acetic acid

<400> SEQUENCE: 2

Xaa Xaa Xaa Xaa Xaa Xaa Xaa Xaa Xaa
1               5

<210> SEQ ID NO 3
<211> LENGTH: 9
<212> TYPE: PRT
<213> ORGANISM: Artificial Sequence
<220> FEATURE:
<223> OTHER INFORMATION: Chemically Synthesized, Cyclic peptide wherein
      side chain amino group of a residue selected from Xaa8 or Xaa9
      forms amide bond with side chain carboxylic acid group of a
      residue selected from Xaa2 or Xaa3
<220> FEATURE:
<221> NAME/KEY: MOD_RES
<222> LOCATION: (1)..(1)
<223> OTHER INFORMATION: is selected from the group consisting of
      absent, Glu and Arg
<220> FEATURE:
<221> NAME/KEY: MOD_RES
<222> LOCATION: (2)..(2)
<223> OTHER INFORMATION: is selected from the group consisting of
      absent, Gly, Phe, Lys, Asp, Glu, Ile, Arg and Cit
<220> FEATURE:
<221> NAME/KEY: MOD_RES
<222> LOCATION: (3)..(3)
<223> OTHER INFORMATION: is selected from the group consisting of Asn,
      Asp, and Glu
<220> FEATURE:
<221> NAME/KEY: MOD_RES
<222> LOCATION: (4)..(4)
<223> OTHER INFORMATION: is Asn
<220> FEATURE:
<221> NAME/KEY: MOD_RES
<222> LOCATION: (5)..(5)
<223> OTHER INFORMATION: is Ile
<220> FEATURE:
<221> NAME/KEY: MOD_RES
<222> LOCATION: (6)..(6)
<223> OTHER INFORMATION: is the modified proline of formula (IV)
<220> FEATURE:
```

```
<221> NAME/KEY: MOD_RES
<222> LOCATION: (7)..(7)
<223> OTHER INFORMATION: is Trp
<220> FEATURE:
<221> NAME/KEY: MOD_RES
<222> LOCATION: (8)..(8)
<223> OTHER INFORMATION: is selected from the group consisting of Ser,
      Thr, 2,4-diaminobutanoic acid, Orn and Lys
<220> FEATURE:
<221> NAME/KEY: MOD_RES
<222> LOCATION: (9)..(9)
<223> OTHER INFORMATION: is selected from the group consisting of
      absent, 2,4-diaminobutanoic acid, Orn, Lys, Glu, Glu-Ala, Glu-Ala-
      Met, Glu-Ala-Met-Met, and 2-(2-(2-aminoethoxy)ethoxy)acetic acid

<400> SEQUENCE: 3

Xaa Xaa Xaa Xaa Xaa Xaa Xaa Xaa Xaa
1               5

<210> SEQ ID NO 4
<211> LENGTH: 7
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms an amide bond with the side
      chain carboxylic acid group of Glu
<220> FEATURE:
<221> NAME/KEY: MOD_RES
<222> LOCATION: (5)..(5)
<223> OTHER INFORMATION: (2S,4S)-4-(4-phenethyl-1H-1,2,3-triazol-1-yl)
      pyrrolidine-2-carboxylic acid
<220> FEATURE:
<221> NAME/KEY: MOD_RES
<222> LOCATION: (7)..(7)
<223> OTHER INFORMATION: AMIDATION, amidated Lys

<400> SEQUENCE: 4

Ile Glu Asn Ile Xaa Trp Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms amide bond with side chain
      carboxylic acid group of Glu
<220> FEATURE:
<221> NAME/KEY: MOD_RES
<222> LOCATION: (5)..(5)
<223> OTHER INFORMATION: (2S,4S)-4-(4-phenethyl-1H-1,2,3-triazol-1-yl)
      pyrrolidine-2-carboxylic acid
<220> FEATURE:
<221> NAME/KEY: MOD_RES
<222> LOCATION: (7)..(7)
<223> OTHER INFORMATION: AMIDATION, amidated Lys

<400> SEQUENCE: 5

Glu Asn Asn Ile Xaa Trp Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms amide bond with side chain
      carboxylic acid group of Asp
<220> FEATURE:
<221> NAME/KEY: MOD_RES
```

```
<222> LOCATION: (4)..(4)
<223> OTHER INFORMATION: (2S,4S)-4-(4-phenethyl-1H-1,2,3-triazol-1-yl)
      pyrrolidine-2-carboxylic acid
<220> FEATURE:
<221> NAME/KEY: MOD_RES
<222> LOCATION: (6)..(6)
<223> OTHER INFORMATION: AMIDATION, Dbu

<400> SEQUENCE: 6

Asp Asn Ile Xaa Trp Lys
1               5

<210> SEQ ID NO 7
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Dbu forms amide bond with side chain
      carboxylic acid group of Glu
<220> FEATURE:
<221> NAME/KEY: MOD_RES
<222> LOCATION: (4)..(4)
<223> OTHER INFORMATION: (2S,4S)-4-(4-phenethyl-1H-1,2,3-triazol-1-yl)
      pyrrolidine-2-carboxylic acid
<220> FEATURE:
<221> NAME/KEY: MOD_RES
<222> LOCATION: (6)..(6)
<223> OTHER INFORMATION: AMIDATION, Dbu

<400> SEQUENCE: 7

Glu Asn Ile Xaa Trp Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Orn forms amide bond with side chain
      carboxylic acid group of Asp
<220> FEATURE:
<221> NAME/KEY: MOD_RES
<222> LOCATION: (4)..(4)
<223> OTHER INFORMATION: (2S,4S)-4-(4-phenethyl-1H-1,2,3-triazol-1-yl)
      pyrrolidine-2-carboxylic acid
<220> FEATURE:
<221> NAME/KEY: MOD_RES
<222> LOCATION: (6)..(6)
<223> OTHER INFORMATION: AMIDATION, amidated Orn

<400> SEQUENCE: 8

Asp Asn Ile Xaa Trp Xaa
1               5

<210> SEQ ID NO 9
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Dbu forms amide bond with side chain
      carboxylic acid group of Asp
<220> FEATURE:
<221> NAME/KEY: MOD_RES
<222> LOCATION: (4)..(4)
<223> OTHER INFORMATION: (2S,4S)-4-(4-phenethyl-1H-1,2,3-triazol-1-yl)
      pyrrolidine-2-carboxylic acid
<220> FEATURE:
<221> NAME/KEY: MOD_RES
<222> LOCATION: (6)..(6)
<223> OTHER INFORMATION: AMIDATION, Dbu
```

```
<400> SEQUENCE: 9

Asp Asn Ile Xaa Trp Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms amide bond with side chain
      carboxylic acid group of Glu
<220> FEATURE:
<221> NAME/KEY: MOD_RES
<222> LOCATION: (5)..(5)
<223> OTHER INFORMATION: (2S,4S)-4-(4-ferrocenyl-1H-1,2,3-triazol-1-yl)
      pyrrolidine-2-carboxylic acid
<220> FEATURE:
<221> NAME/KEY: MOD_RES
<222> LOCATION: (7)..(7)
<223> OTHER INFORMATION: AMIDATION, amidated Lys

<400> SEQUENCE: 10

Ile Glu Asn Ile Xaa Trp Lys
1               5

<210> SEQ ID NO 11
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms amide bond with side chain
      carboxylic acid group of Asp
<220> FEATURE:
<221> NAME/KEY: MOD_RES
<222> LOCATION: (4)..(4)
<223> OTHER INFORMATION: (2S,4S)-4-(4-ferrocenyl-1H-1,2,3-triazol-1-yl)
      pyrrolidine-2-carboxylic acid
<220> FEATURE:
<221> NAME/KEY: MOD_RES
<222> LOCATION: (6)..(6)
<223> OTHER INFORMATION: AMIDATION, amidated Lys

<400> SEQUENCE: 11

Asp Asn Ile Xaa Trp Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms amide bond with side chain
      carboxylic acid group of Asp
<220> FEATURE:
<221> NAME/KEY: MOD_RES
<222> LOCATION: (3)..(3)
<223> OTHER INFORMATION: (S)-2-amino-2-cyclohexylacetic acid (Cyclohexyl
      glycine)
<220> FEATURE:
<221> NAME/KEY: MOD_RES
<222> LOCATION: (4)..(4)
<223> OTHER INFORMATION: (2S,4S)-4-(4-ferrocenyl-1H-1,2,3-triazol-1-yl)
      pyrrolidine-2-carboxylic acid
<220> FEATURE:
<221> NAME/KEY: MOD_RES
<222> LOCATION: (6)..(6)
<223> OTHER INFORMATION: AMIDATION, amidated Lys

<400> SEQUENCE: 12
```

```
Asp Asn Xaa Xaa Trp Lys
1               5
```

<210> SEQ ID NO 13
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms amide bond with side chain
      carboxylic acid group of Asp
<220> FEATURE:
<221> NAME/KEY: MOD_RES
<222> LOCATION: (4)..(4)
<223> OTHER INFORMATION: (2S,4S)-4-(4-ferrocenyl-1H-1,2,3-triazol-1-yl)
      pyrrolidine-2-carboxylic acid
<220> FEATURE:
<221> NAME/KEY: MOD_RES
<222> LOCATION: (5)..(5)
<223> OTHER INFORMATION: (S)-2-amino-3-(benzo[b]thiophen-3-yl)propanoic
      acid (Benzotheinyl Alanine)
<220> FEATURE:
<221> NAME/KEY: MOD_RES
<222> LOCATION: (6)..(6)
<223> OTHER INFORMATION: AMIDATION, amidated Lys

<400> SEQUENCE: 13

```
Asp Asn Ile Xaa Xaa Lys
1               5
```

<210> SEQ ID NO 14
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms amide bond with side chain
      carboxylic acid group of Asp
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: (2S,4S)-4-(4-ferrocenyl-1H-1,2,3-triazol-1-yl)
      pyrrolidine-2-carboxylic acid
<220> FEATURE:
<221> NAME/KEY: MOD_RES
<222> LOCATION: (6)..(6)
<223> OTHER INFORMATION: AMIDATION, amidated Lys

<400> SEQUENCE: 14

```
Asp Asn Xaa Xaa Trp Lys
1               5
```

<210> SEQ ID NO 15
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms amide bond with side chain
      carboxylic acid group of Asp
<220> FEATURE:
<221> NAME/KEY: MOD_RES
<222> LOCATION: (4)..(4)
<223> OTHER INFORMATION: (2S,4S)-4-(4-(adamantan-2-yl)-1H-1,2,3-triazol-
      1-yl)-pyrrolidine-2-carboxylic acid
<220> FEATURE:
<221> NAME/KEY: MOD_RES
<222> LOCATION: (6)..(6)
<223> OTHER INFORMATION: AMIDATION, amidated Lys

```
<400> SEQUENCE: 15

Asp Asn Ile Xaa Trp Lys
1               5

<210> SEQ ID NO 16
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms amide bond with side chain
      carboxylic acid group of Asp
<220> FEATURE:
<221> NAME/KEY: MOD_RES
<222> LOCATION: (4)..(4)
<223> OTHER INFORMATION: (2S,4S)-4-(4-(4-ethylphenyl)-1H-1,2,3-triazol-
      1-yl)-pyrrolidine-2-carboxylic acid
<220> FEATURE:
<221> NAME/KEY: MOD_RES
<222> LOCATION: (6)..(6)
<223> OTHER INFORMATION: AMIDATION, amidated Lys

<400> SEQUENCE: 16

Asp Asn Ile Xaa Trp Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms amide bond with side chain
      carboxylic acid group of Asp
<220> FEATURE:
<221> NAME/KEY: MOD_RES
<222> LOCATION: (2)..(2)
<223> OTHER INFORMATION: 2,4-diaminobutanoic acid
<220> FEATURE:
<221> NAME/KEY: MOD_RES
<222> LOCATION: (3)..(3)
<223> OTHER INFORMATION: (S)-2-amino-2-cyclohexylacetic acid (Cyclohexyl
      Glycine)
<220> FEATURE:
<221> NAME/KEY: MOD_RES
<222> LOCATION: (4)..(4)
<223> OTHER INFORMATION: (2S,4S)-4-(4-(4-ethylphenyl)-1H-1,2,3-triazol-
      1-yl)-pyrrolidine-2-carboxylic acid
<220> FEATURE:
<221> NAME/KEY: MOD_RES
<222> LOCATION: (5)..(5)
<223> OTHER INFORMATION: (S)-2-amino-3-(benzo[b]thiophen-3-yl)propanoic
      acid (Benzothienyl Alanine)
<220> FEATURE:
<221> NAME/KEY: MOD_RES
<222> LOCATION: (6)..(6)
<223> OTHER INFORMATION: AMIDATION, amidated Lys

<400> SEQUENCE: 17

Asp Xaa Xaa Xaa Xaa Lys
1               5

<210> SEQ ID NO 18
<211> LENGTH: 5
<212> TYPE: PRT
<213> ORGANISM: Artificial Sequence
<220> FEATURE:
<223> OTHER INFORMATION: Chemically Synthesized, Cyclic peptide wherein
      side chain amino group of Dbu forms amide bond with side chain
      carboxylic acid group of Asp
<220> FEATURE:
<221> NAME/KEY: MOD_RES
```

```
<222> LOCATION: (3)..(3)
<223> OTHER INFORMATION: (2S,4S)-4-(4-ferrocenyl-1H-1,2,3-triazol-1-yl)
      pyrrolidine-2-carboxylic acid
<220> FEATURE:
<221> NAME/KEY: MOD_RES
<222> LOCATION: (5)..(5)
<223> OTHER INFORMATION: AMIDATION, Dbu

<400> SEQUENCE: 18

Asp Ile Xaa Trp Xaa
1               5

<210> SEQ ID NO 19
<211> LENGTH: 6
<212> TYPE: PRT
<213> ORGANISM: Artificial Sequence
<220> FEATURE:
<223> OTHER INFORMATION: Chemically Synthesized, Cyclic peptide wherein
      side chain amino group of Lys forms amide bond with side chain
      carboxylic acid group of Asp
<220> FEATURE:
<221> NAME/KEY: MOD_RES
<222> LOCATION: (3)..(3)
<223> OTHER INFORMATION: (S)-2-amino-2-cyclopropylacetic acid
      (Cyclopropyl Glycine)
<220> FEATURE:
<221> NAME/KEY: MOD_RES
<222> LOCATION: (4)..(4)
<223> OTHER INFORMATION: (2S,4S)-4-(4-ferrocenyl-1H-1,2,3-triazol-1-yl)
      pyrrolidine-2-carboxylic acid
<220> FEATURE:
<221> NAME/KEY: MOD_RES
<222> LOCATION: (6)..(6)
<223> OTHER INFORMATION: AMIDATION, amidated Lys

<400> SEQUENCE: 19

Asp Asn Xaa Xaa Trp Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (5)..(5)
<223> OTHER INFORMATION: (2S,4S)-4-(4-phenethyl-1H-1,2,3-triazol-1-yl)
      pyrrolidine-2-carboxylic acid
<220> FEATURE:
<221> NAME/KEY: MOD_RES
<222> LOCATION: (7)..(7)
<223> OTHER INFORMATION: AMIDATION, amidated Lys

<400> SEQUENCE: 20

Ile Glu Asn Ile Xaa Trp Lys
1               5

<210> SEQ ID NO 21
<211> LENGTH: 4
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (3)..(3)
<223> OTHER INFORMATION: bAla
```

```
<220> FEATURE:
<221> NAME/KEY: MOD_RES
<222> LOCATION: (4)..(4)
<223> OTHER INFORMATION: AMIDATION, amidated Cys

<400> SEQUENCE: 21

Xaa Gln Xaa Cys
 1

<210> SEQ ID NO 22
<211> LENGTH: 4
<212> TYPE: PRT
<213> ORGANISM: Artificial Sequence
<220> FEATURE:
<223> OTHER INFORMATION: Chemically Synthesized
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (3)..(3)
<223> OTHER INFORMATION: bAla

<400> SEQUENCE: 22

Xaa Gln Xaa Cys
 1
```